(12) United States Patent
Diedrichs et al.

(10) Patent No.: US 8,030,347 B2
(45) Date of Patent: Oct. 4, 2011

(54) CYLOPENTA[B]BENZOFURAN DERIVATIVES AND THE UTILIZATION THEREOF

(75) Inventors: Nicole Diedrichs, Velbert (DE); Thomas Fahrig, Bergisch Gladbach (DE); Irene Gerlach, Lörrach (DE); Jaques Ragot, Düsseldorf (DE); Joachim Schuhmacher, Wuppertal (DE); Kai Thede, Wuppertal (DE); Ervin Horváth, Leverkusen (DE)

(73) Assignee: Bayer HealthCare AG, Leverkusen (DE)

( * ) Notice: Subject to any disclaimer, the term of this patent is extended or adjusted under 35 U.S.C. 154(b) by 1032 days.

(21) Appl. No.: 11/596,907

(22) PCT Filed: May 14, 2005

(86) PCT No.: PCT/EP2005/005298
§ 371 (c)(1),
(2), (4) Date: Aug. 7, 2007

(87) PCT Pub. No.: WO2005/113529
PCT Pub. Date: Dec. 1, 2005

(65) Prior Publication Data
US 2009/0018113 A1    Jan. 15, 2009

(30) Foreign Application Priority Data

May 18, 2004    (DE) .......................... 10 2004 024 504

(51) Int. Cl.
*A61K 31/343* (2006.01)
*C07D 307/93* (2006.01)
(52) U.S. Cl. ....................................... 514/468; 549/458
(58) Field of Classification Search .................. 549/458; 514/468
See application file for complete search history.

(56) References Cited

U.S. PATENT DOCUMENTS

| 6,518,274 B1 | 2/2003 | Gehling et al. | 514/257 |
| 2003/0144334 A1 | 7/2003 | Guarnieri et al. | 514/397 |

FOREIGN PATENT DOCUMENTS

| WO | 0007579 | 2/2000 |
| WO | 0008007 | 2/2000 |

OTHER PUBLICATIONS

Diedrichs, et al., A Highly Efficient Synthesis of Rocaglaols by a Novel α-Arylation of Ketones, Eur. J. Org. Chem., 9: 1731-1735 (2005).
Karin, M et al; "AP-1 function and regulation"; Current Opinion in Cell Biology; 1997; pp. 240-246.
Shaulian, E. et al; "AP-1 as a regulator of cell life and death"; Nature Cell Biology, vol. 4, May 2002, pp. E131-E136.
Holtmann, H., et al; "Induction of Interleukin-8 Synthesis Integrates Effects on Transcription and mRNA Degradation from at Least Three Different Cytokine- or Stress-Activated Signal Transduction Pathways"; Molecular and Cellular Biology, Oct. 1999, pp. 6742-6753.
Chang, Y, et al; "Lymphotoxin β Receptor Induces Interleukin 8 Gene Expression via NF-kB and AP-1 Activation"; Experimental Cell Research, 278, (2002); pp. 166-174.
Houston, et al; "Prediction of Hepatic Clearance from Microsomes, Hepatocytes, and Liver Slices"; Drug Metabolism Reviews, 29 (4), 1997, pp. 891-922.
Silvestrini, et al; "In Vitro Cytotoxic Activity of Taxol® and Taxotere on Primary Cultures and Established Cell Lines of Human Ovarian Cancer"; Taxol ® and Taxotere in Ovarian Cancer Cells; Istituto Nazional per lo Studio e la Cura dei Tumori, Milan, Italy, published Aug. 2, 1993, AlphaMed Press; pp. 1066-5099.
Edelman, et al; "Promising new agents in the treatment of non-small cell lung cancer"; Cancer Chemother. Pharmacol., 1996, 37, pp. 385-393.
Eijkenboom et al; "Effects of subdural haematoma on sensorimotor functioning and spatial learning in rats"; Neuro Pharmacology, 39, 2000, pp. 817-834.
Bissery et al; "Docetaxel (Taxotere®): a review of preclinical and clinical experience. Part I: preclinical experience"; Anti-cancer Drugs 1995, vol. 6, pp. 339-368.

*Primary Examiner* — Bernard Dentz
(74) *Attorney, Agent, or Firm* — Norris McLaughlin & Marcus, P.A.

(57) ABSTRACT

The present application relates to a novel cyclopenta[b]benzofuran derivatives, processes for their preparation and their use for the manufacture of medicaments, in particular for the prophylaxis and/or therapy of acute or chronic disorders characterized by elevated cellular stress, by local or systemic inflammatory processes or by hyperproliferation.

15 Claims, No Drawings

CYLOPENTA[B]BENZOFURAN DERIVATIVES AND THE UTILIZATION THEREOF

The present application relates to novel cyclopenta[b]benzofuran derivatives, processes for their preparation and their use for the manufacture of medicaments, in particular for the prophylaxis and/or therapy of acute or chronic disorders characterized by elevated cellular stress, by local or systemic inflammatory processes or by hyperproliferation.

The compounds of the invention are derived from a class of natural products which are referred to as rocaglaols/rocaglamides and which can be extracted from various species of the *Aglaia* plant. Since the initial isolation of a dihydrocyclopentabenzofuranol derivative called rocaglamide (*J. Chem. Soc., Chem. Commun.* 1982, 1150; U.S. Pat. No. 4,539,414), several new, including synthetically prepared, derivatives and their biological effect have been described (cf., for example, *J. Chem. Soc., Chem. Commun.* 1991, 1137; *Phytochemistry* 32, 307 (1993); WO 96/04284; *Tetrahedron* 52, 6931 (1996); *Phytochemistry* 44, 1455 (1997); *Phytochemistry* 45, 1579 (1997); *Tetrahedron* 53, 17625 (1997); JP 11012279; WO 97/08161; WO 00/07579; WO 00/08007; DE 199 34 952-A1).

The effect of cyclopentabenzofuran derivatives as inhibitors of nuclear factor kappa B (NF-κB)-mediated signal transduction has been described previously [WO 00/08007; WO 00/07579; *J. Biol. Chem.* 277, 44791 (2002)]. NF-κB is a transcription factor which occupies a central role in inflammatory processes, but also in carcinogenesis. In its active, DNA-binding form, it is composed of dimeric combinations of various members of the NF-κB/Rel family of proteins [*Ann. Rev. Immunol.* 16, 225 (1998)]. Under basal, non-stimulated conditions, NF-κB is in the form of a cytoplasmic, inactive form through binding to an inhibitory protein (I-κB). Stimulation is followed by rapid phosphorylation of I-κB by I-κB kinases and, as a consequence, proteolytic degradation of I-κB. NF-κB is liberated in its active form thereby, and translocation thereof into the cell nucleus is made possible. In its property as transcription factor, NF-κB activates or modulates the expression of various genes, especially those whose products are responsible for inflammatory responses and for cell growth and differentiation [*J. Biol. Chem.* 274, 27339 (1999)].

It has now surprisingly been found that the compounds of the invention additionally inhibit the activity of a second transcription factor complex, of activator protein-1 (AP-1). AP-1 is a transcription factor composed of dimers of the Jun, Fos, Maf and ATF families of proteins and which is localized in the cell nucleus. The activity of AP-1 is induced by a number of very diverse stimuli, inter alia by cytokines, bacterial and viral infections and by various types of physical or chemical stress. Activating signals lead on the one hand to an increased production of the individual components of the transcription factor, and on the other hand, through stimulation of certain kinases such as, for example, Jun kinases, to phosphorylation of specific amino acids. Both processes lead to an enhanced interaction of AP-1 with its target genes and thus make their expression or modulation possible. These genes include not only those whose products are involved in inflammatory processes, but also those controlling cell division or acting as regulators of cell death or survival [*Curr. Opin. Cell Biol.* 9, 240 (1997); *Nature Cell Biol.* 4, E131 (2002)].

On the one hand, proinflammatory cytokines such as, for example, interleukin-1 (IL-1) or tumor necrosis factor (TNF), and oxidative stress are potent activators of NF-κB- and AP-1-mediated signal transduction. On the other hand, activation of NF-κB and/or AP-1 brings about new production of various cytokines (such as, for example, IL-1 and TNF), various chemokines (such as, for example, interleukin-8 (IL-8) and monocyte chemoattractant protein-1 (MCP-1)) and various enzymes (such as, for example, cyclooxygenase-2 or nitric oxide synthase-2 (NOS-2, iNOS)). The main function of the newly produced peptides/proteins or of the final products resulting from the activity of the newly produced enzymes is the recruitment and activation of inflammatory cells. NF-κB and AP-1 are thus central factors in the induction and maintenance of inflammatory processes.

The pathogenesis or pathophysiology of a large number of disorders is characterized by acute, exaggerated or chronic inflammatory responses which may be confined locally to a tissue or systemic in nature. These diseases are distinguished by locally or systemically elevated cytokine and/or chemokine levels and by an increased presence of various types of inflammatory cells such as, for example, macrophages, polymorphonuclear leukocytes, T lymphocytes or B cells. These disorders include chronic inflammatory and autoimmune diseases (such as, for example, Crohn's disease, ulcerative colitis, rheumatoid arthritis, psoriasis, multiple sclerosis, lupus, asthma, diabetes), cardiovascular disorders (such as, for example, coronary heart disease, myocardial infarction, atherosclerosis, restenosis, thromboses), fibrotic disorders of the liver and other organs, cerebrovascular disorders (such as, for example, stroke, craniocerebral trauma, spinal cord injuries) and chronic neurodegenerative disorders (such as, for example, Alzheimer's disease, Parkinson's disease, Huntington's chorea, amyotrophic lateral sclerosis, peripheral neuropathies and chronic pain). Dysregulated or exaggerated cytokine/chemokine production is likewise causally linked to the development or the sequelae of radiation damage, transplant rejection, sepsis and septic shock, and bacterial meningitis. Inhibition or modulation of the transcriptional activity of NF-κB and/or AP-1, as described for the compounds of the invention, might thus represent a promising novel therapeutic principle for the disorders listed above.

Besides their central function in inflammatory processes, NF-κB and AP-1 have substantial importance in the regulation of cell division, cell growth and cell differentiation. During the formation and growth of tumors there is activation of cellular signaling pathways which, under normal conditions, control cell growth, differentiation and other biological processes. A large number of tumor-inducing substances and factors (such as, for example, epidermal growth factor (EGF), phorbol ester, UV radiation) lead to activation of NF-κB and/or AP-1, and a number of the genes controlled by NF-κB and/or AP-1 belong to the oncogenes (such as, for example, c-myc, c-rel, melanoma growth stimulating activity (MGSA)). Through the inhibitory/modulating activity on the NF-κB- and/or AP-1-mediated signal transduction, the use of the compounds of the invention might thus represent a novel therapeutic principle for the treatment of hyperproliferative disorders such as solid tumors (such as, for example, breast cancer, lung cancer, tumors of the brain and of the nervous system, skin cancer, liver cancer, tumors of the reproductive organs, tumors of the digestive tract, bladder cancer, tumors of the urinary tract systems, tumors of various endocrine glands, tumors of the eye), lymphomas (such as, for example, Hodgkin's disease, lymphomas of the central nervous system), sarcomas (such as, for example, osteosarcomas, lymphosarcomas) and leukemias (such as, for example, acute myeloid leukemia, lymphoblastic leukemias, myelogenous leukemias).

NF-κB and AP-1 additionally play a substantial role in the replication of lymphotrophic viruses such as HIV, HTLV and Epstein-Barr virus. Activation of viral genes which are necessary for replication may be brought about by virus-mediated activation of NF-κB and/or AP-1 in the host cell. Besides the importance for the replication of lymphotrophic viruses, it is also suspected that there is a positive influence on gene expression in cytomegalovirus (CMV) and in adenoviruses by NF-κB/AP-1. Inhibitors/modulators of NF-κB and/or AP-1 activity might thus also exert antiviral effects.

The present invention relates to compounds of the general formula (I)

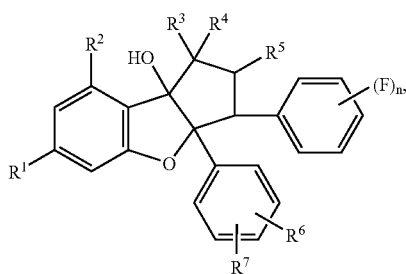

in which $R^1$ is hydrogen, benzyloxy, ethoxy, n-propoxy or a group of the formula $R^8$—C(=O)—NH—, where ethoxy may be substituted in position 2, and n-propoxy in position 2 or 3, by $(C_1-C_6)$-alkoxy, amino, mono- or di-$(C_1-C_6)$-alkylamino, $(C_3-C_8)$-cycloalkylamino, N-$(C_3-C_8)$-cycloalkyl-N-$(C_1-C_6)$-alkylamino or by a 4- to 7-membered heterocycle which is bonded via an N atom, where mono- and di-$(C_1-C_6)$-alkylamino in turn may be substituted by hydroxy, $(C_1-C_4)$-alkoxy, amino, mono- or di-$(C_1-C_4)$-alkylamino, and in which $R^8$ is 5- or 6-membered heteroaryl which may be substituted by $(C_1-C_4)$-alkyl or halogen, $R^2$ is hydrogen, ethoxy or n-propoxy, where ethoxy may be substituted in position 2, and n-propoxy in position 2 or 3, by $(C_1-C_6)$-alkoxy, amino, mono- or di-$(C_1-C_6)$-alkylamino, $(C_3-C_8)$-cycloalkylamino, N-$(C_3-C_8)$-cycloalkyl-N-$(C_1-C_6)$-alkylamino or by a 4- to 7-membered heterocycle which is bonded via an N atom, where mono- and di-$(C_1-C_6)$-alkylamino in turn may be substituted by hydroxy, $(C_1-C_4)$-alkoxy, amino, mono- or di-$(C_1-C_4)$-alkylamino, but where $R^1$ and $R^2$ are not simultaneously hydrogen, $R^3$ is hydroxy or amino and $R^4$ is hydrogen, or $R^3$ and $R^4$ together with the carbon atom to which they are bonded form a group of the formula >C=O or >C=N—OH, $R^5$ is mono- or di-$(C_1-C_6)$-alkylaminocarbonyl, n is the number 0, 1, 2 or 3, $R^6$ is located in the meta or para position relative to the point of linkage of the phenyl ring to the tricycle, and is halogen, $(C_1-C_6)$-alkyl, $(C_1-C_6)$-alkoxy, $(C_6-C_{10})$-aryl, 5- to 10-membered heteroaryl or a group of the formula —$NR^9R^{10}$, where aryl and heteroaryl in turn may each be substituted once to twice, identically or differently, by halogen, cyano, $(C_1-C_4)$-alkylsulfonyl or a group of the formula —$NR^9R^{10}$, and in which $R^9$ and $R^{10}$ are independently of one another hydrogen, $(C_1-C_6)$-alkyl, phenyl, benzyl or pyridylmethyl, or together with the nitrogen atom to which they are bonded form a 4- to 7-membered heterocycle, and $R^7$ is located in the meta or para position relative to the point of linkage of the phenyl ring to the tricycle, and is in the ortho position relative to $R^6$, and is hydrogen, halogen, $(C_1-C_6)$-alkyl, $(C_1-C_6)$-alkoxy or a group of the formula —$NR^{11}R^{12}$, in which $R^{11}$ and $R^{12}$ are independently of one another hydrogen, $(C_1-C_6)$-alkyl, phenyl, benzyl or pyridylmethyl, or together with the nitrogen atom to which they are bonded form a 4- to 7-membered heterocycle, or $R^6$ and $R^7$ together with the phenyl ring to which they are bonded form a group of the formula

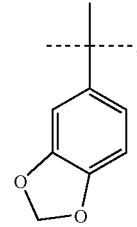

and their salts, solvates and solvates of the salts thereof.

The present invention further relates to compounds of the general formula (I) in which $R^1$ is hydrogen, benzyloxy, ethoxy, n-propoxy or a group of the formula $R^8$—C(=O)—NH—, where ethoxy may be substituted in position 2, and n-propoxy in position 2 or 3, by $(C_1-C_6)$-alkoxy, amino, mono- or di-$(C_1-C_6)$-alkylamino, $(C_3-C_8)$-cycloalkylamino, N-$(C_3-C_8)$-cycloalkyl-N-$(C_1-C_6)$-alkylamino or by a 4- to 7-membered heterocycle which is bonded via an N atom, where mono- and di-$(C_1-C_6)$-alkylamino in turn may be substituted by hydroxy, $(C_1-C_4)$-alkoxy, amino, mono- or di-$(C_1-C_4)$-alkylamino, and in which $R^8$ is 5- or 6-membered heteroaryl which may be substituted by $(C_1-C_4)$-alkyl or halogen, $R^2$ is hydrogen, ethoxy or n-propoxy, where ethoxy may be substituted in position 2, and n-propoxy in position 2 or 3, by $(C_1-C_6)$-alkoxy, amino, mono- or di-$(C_1-C_6)$-alkylamino, $(C_3-C_8)$-cycloalkylamino, N-$(C_3-C_8)$-cycloalkyl-N-$(C_1-C_6)$-alkylamino or by a 4- to 7-membered heterocycle which is bonded via an N atom, where mono- and di-$(C_1-C_6)$-alkylamino in turn may be substituted by hydroxy, $(C_1-C_4)$-alkoxy, amino, mono- or di-$(C_1-C_4)$-alkylamino, but where $R^1$ and $R^2$ are not simultaneously hydrogen, $R^3$ is hydroxy or amino and R⁴ is hydrogen, or R³ and R⁴ together with the carbon atom to which they are bonded form a group of the formula >C=O or >C=N—OH, R⁵ is hydrogen, n is the number 0, 1, 2 or 3, R⁶ is located in the meta or para position relative to the point of linkage of the phenyl ring to the tricycle, and is ($C_6$-$C_{10}$)-aryl, 5- to 10-membered heteroaryl or a group of the formula —NR⁹R¹⁰, where aryl and heteroaryl in turn may each be substituted once to twice, identically or differently, by halogen, cyano, ($C_1$-$C_4$)-alkylsulfonyl or a group of the formula —NR⁹R¹⁰, and in which R⁹ and R¹⁰ are independently of one another hydrogen, ($C_1$-$C_6$)-alkyl, phenyl, benzyl or pyridylmethyl, or together with the nitrogen atom to which they are bonded form a 4 to 7-membered heterocycle, and R⁷ is located in the meta or para position relative to the point of linkage of the phenyl ring to the tricycle, and in the ortho position relative to R⁶, and is hydrogen, halogen, ($C_1$-$C_6$)-alkyl, ($C_1$-$C_6$)-alkoxy or a group of the formula —NR¹¹R¹², in which R¹¹ and R¹² are independently of one another hydrogen, ($C_1$-$C_6$)-alkyl, phenyl, benzyl or pyridylmethyl, or together with the nitrogen atom to which they are bonded form a 4- to 7-membered heterocycle, or R⁶ and R⁷ together with the phenyl ring to which they are bonded form a group of the formula

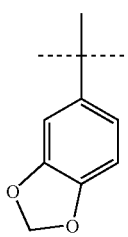

and their salts, solvates and solvates of the salts thereof.

The present invention further relates to compounds of the general formula (I) in which R¹ is hydrogen, benzyloxy, ethoxy, n-propoxy or a group of the formula R⁸—C(=O)—NH—, where ethoxy may be substituted in position 2, and n-propoxy in position 2 or 3, by ($C_1$-$C_6$)-alkoxy, amino, mono- or di-($C_1$-$C_6$)-alkylamino, ($C_3$-$C_8$)-cycloalkylamino, N-($C_3$-$C_8$)-cycloalkyl-N-($C_1$-$C_6$)-alkylamino or by a 4- to 7-membered heterocycle which is bonded via an N atom, where mono- and di-($C_1$-$C_6$)-alkylamino in turn may be substituted by hydroxy, ($C_1$-$C_4$)-alkoxy, amino, mono- or di-($C_1$-$C_4$)-alkylamino, and in which R⁸ is 5- or 6-membered heteroaryl which may be substituted by ($C_1$-$C_4$)-alkyl or halogen, R² is hydrogen, ethoxy or n-propoxy, where ethoxy may be substituted in position 2, and n-propoxy in position 2 or 3, by ($C_1$-$C_6$)-alkoxy, amino, mono- or di-($C_1$-$C_6$)-alkylamino, ($C_3$-$C_8$)-cycloalkylamino, N-($C_3$-$C_8$)-cycloalkyl-N-($C_1$-$C_6$)-alkylamino or by a 4 to 7-membered heterocycle which is bonded via an N atom, where mono- and di-($C_1$-$C_6$)-alkylamino in turn may be substituted by hydroxy, ($C_1$-$C_4$)-alkoxy, amino, mono- or di-($C_1$-$C_4$)-alkylamino, but where R¹ and R² are not simultaneously hydrogen, R³ is amino and R⁴ is hydrogen, or R³ and R⁴ together with the carbon atom to which they are bonded form a group of the formula >C=N—OH, R⁵ is hydrogen, n is the number 0, 1, 2 or 3, R⁶ is located in the meta or para position relative to the point of linkage of the phenyl ring to the tricycle, and is halogen, ($C_1$-$C_6$)-alkyl or ($C_1$-$C_6$)-alkoxy, and R⁷ is located in the meta or para position relative to the point of linkage of the phenyl ring to the tricycle, and in the ortho position relative to R⁶, and is hydrogen, halogen, ($C_1$-$C_6$)-alkyl, ($C_1$-$C_6$)-alkoxy or a group of the formula —NR¹¹R¹², in which R¹¹ and R¹² are independently of one another hydrogen, ($C_1$-$C_6$)-alkyl, phenyl, benzyl or pyridylmethyl, or together with the nitrogen atom to which they are bonded form a 4- to 7-membered heterocycle, or R⁶ and R⁷ together with the phenyl ring to which they are bonded form a group of the formula

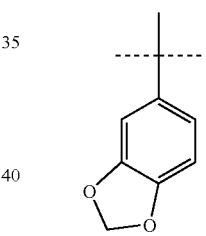

and the salts, solvates and solvates of the salts thereof.

The present invention further relates to compounds of the general formula (I) in which R¹ is hydrogen, benzyloxy, ethoxy, n-propoxy or a group of the formula R⁸—C(=O)—NH—, where ethoxy may be substituted in position 2, and n-propoxy in position 2 or 3, by ($C_1$-$C_6$)-alkoxy, amino, mono- or di-($C_1$-$C_6$)-alkylamino, ($C_3$-$C_8$)-cycloalkylamino, N-($C_3$-$C_8$)-cycloalkyl-N-($C_1$-$C_6$)-alkylamino or by a 4- to 7-membered heterocycle which is bonded via an N atom, where mono- and di-($C_1$-$C_6$)-alkylamino in turn may be substituted by hydroxy, ($C_1$-$C_4$)-alkoxy, amino, mono- or di-($C_1$-$C_4$)-alkylamino, and in which R⁸ is 5- or 6-membered heteroaryl which may be substituted by ($C_1$-$C_4$)-alkyl or halogen, R² is hydrogen, ethoxy or n-propoxy, where ethoxy may be substituted in position 2, and n-propoxy in position 2 or 3, by ($C_1$-$C_6$)-alkoxy, amino, mono- or di-($C_1$-$C_6$)-alkylamino, ($C_3$-$C_8$)-cycloalkylamino, N-($C_3$-$C_8$)-cycloalkyl-N-($C_1$-$C_6$)-alkylamino or by a 4- to 7-membered heterocycle which is bonded via an N atom, where mono- and di-$(C_1-C_6)$-alkylamino in turn may be substituted by hydroxy, $(C_1-C_4)$-alkoxy, amino, mono- or di-$(C_1-C_4)$-alkylamino, but where $R^1$ and $R^2$ are not simultaneously hydrogen, $R^3$ is hydroxy, and $R^4$ is hydrogen, or $R^3$ and $R^4$ together with the carbon atom to which they are bonded form a group of the formula >C=O, $R^5$ is hydrogen, n is the number 0, 1, 2 or 3, $R^6$ is located in the meta or para position relative to the point of linkage of the phenyl ring to the tricycle, and is halogen, $(C_1-C_6)$-alkyl or $(C_1-C_6)$-alkoxy, and $R^7$ is located in the meta or para position relative to the point of linkage of the phenyl ring to the tricycle, and in the ortho position relative to $R^6$, and is hydrogen, halogen, $(C_1-C_6)$-alkyl, $(C_1-C_6)$-alkoxy or a group of the formula —$NR^{11}R^{12}$, in which $R^{11}$ and $R^{12}$ are independently of one another hydrogen, $(C_1-C_6)$-alkyl, phenyl, benzyl or pyridylmethyl, or together with the nitrogen atom to which they are bonded form a 4- to 7-membered heterocycle, or $R^6$ and $R^7$ together with the phenyl ring to which they are bonded form a group of the formula

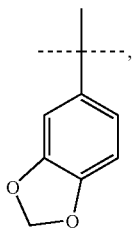

and the salts, solvates and solvates of the salts thereof.

The present invention further relates to compounds of the general formula (I) in which $R^1$ is ethoxy, n-propoxy or a group of the formula $R^8$—C(=O)—NH—, where ethoxy is substituted in position 2, and n-propoxy in position 2 or 3, by $(C_1-C_6)$-alkoxy, amino, mono- or di-$(C_1-C_6)$-alkylamino, $(C_3-C_8)$-cycloalkylamino, N-$(C_3-C_8)$-cycloalkyl-N-$(C_1-C_6)$-alkylamino or by a 4- to 7-membered heterocycle which is bonded via an N atom, where mono- and di-$(C_1-C_6)$-alkylamino in turn may be substituted by hydroxy, $(C_1-C_4)$-alkoxy, amino, mono- or di-$(C_1-C_4)$-alkylamino, and in which $R^8$ is 5- or 6-membered heteroaryl which may be substituted by $(C_1-C_4)$-alkyl or halogen, $R^2$ is ethoxy or n-propoxy, where ethoxy is substituted in position 2, and n-propoxy in position 2 or 3, by $(C_1-C_6)$-alkoxy, amino, mono- or di-$(C_1-C_6)$-alkylamino, $(C_3-C_8)$-cycloalkylamino, N-$(C_3-C_8)$-cycloalkyl-N-$(C_1-C_6)$-alkylamino or by a 4- to 7-membered heterocycle which is bonded via an N atom, where mono- and di-$(C_1-C_6)$-alkylamino in turn may be substituted by hydroxy, $(C_1-C_4)$-alkoxy, amino, mono- or di-$(C_1-C_4)$-alkylamino, $R^3$ is hydroxy and $R^4$ is hydrogen, or $R^3$ and $R^4$ together with the carbon atom to which they are bonded form a group of the formula >C=O, $R^5$ is hydrogen, n is the number 0, 1, 2 or 3, $R^6$ is located in the meta or para position relative to the point of linkage of the phenyl ring to the tricycle, and is halogen, $(C_1-C_6)$-alkyl or $(C_1-C_6)$-alkoxy, and $R^7$ is located in the meta or para position relative to the point of linkage of the phenyl ring to the tricycle, and in the ortho position relative to $R^6$, and is hydrogen, halogen, $(C_1-C_6)$-alkyl, $(C_1-C_6)$-alkoxy or a group of the formula —$NR^{11}R^{12}$, in which $R^{11}$ and $R^{12}$ are independently of one another hydrogen, $(C_1-C_6)$-alkyl, phenyl, benzyl or pyridylmethyl, or together with the nitrogen atom to which they are bonded form a 4- to 7-membered heterocycle, or $R^6$ and $R^7$ together with the phenyl ring to which they are bonded form a group of the formula

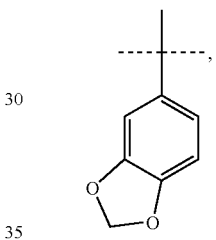

and the salts, solvates and solvates of the salts thereof.

Compounds according to the invention are the compounds of the formula (I) and the salts, solvates and solvates of the salts thereof, the compounds which are encompassed by formula (I) and are of the formulae mentioned hereinafter, and the salts, solvates and solvates of the salts thereof, and the compounds which are encompassed by formula (I) and are mentioned hereinafter as exemplary embodiments, and the salts, solvates and solvates of the salts thereof, insofar as the compounds encompassed by formula (I) and mentioned hereinafter are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

Where the compounds according to the invention can occur in tautomeric forms, the present invention encompasses all tautomeric forms.

Salts preferred for the purposes of the present invention are physiologically acceptable salts of the compounds according to the invention. However, salts which are themselves unsuitable for pharmaceutical applications but can be used for example for isolating or purifying the compounds according to the invention are also encompassed.

Physiologically acceptable salts of the compounds according to the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases such as, for example and preferably, alkali metal salts (e.g. sodium and potassium salts), alkaline earth metal salts (e.g. calcium and magnesium salts) and ammonium salts derived from ammonia or organic amines having 1 to 16 C atoms, such as, for example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methyl-morpholine, arginine, lysine, ethylenediamine and N-methylpiperidine.

Solvates refer for the purposes of the invention to those forms of the compounds according to the invention which form a complex in the solid or liquid state through coordination with solvent molecules. Hydrates are a specific form of solvates in which the coordination takes place with water. Solvates preferred in the context of the present invention are hydrates.

The present invention also encompasses prodrugs of the compounds according to the invention. The term "prodrugs" encompasses compounds which themselves may be biologically active or inactive but are converted during their residence time in the body into compounds according to the invention (for example by metabolism or hydrolysis).

In the context of the present invention, the substituents have the following meaning unless otherwise specified:

$(C_1-C_6)$-Alkyl and $(C_1-C_4)$-alkyl are in the context of the invention a straight-chain or branched alkyl radical having respectively 1 to 6 and 1 to 4 carbon atoms. A straight-chain or branched alkyl radical having 1 to 4 carbon atoms is preferred. Examples which may be preferably mentioned are: methyl, ethyl, n-propyl, isopropyl, n-butyl, isobutyl, sec-butyl, tert-butyl, 1-ethylpropyl, n-pentyl and n-hexyl.

$(C_3-C_8)$-Cycloalkyl and $(C_3-C_6)$-cycloalkyl are in the context of the invention a mono- or, where appropriate, bicyclic cycloalkyl group having respectively 3 to 8 and 3 to 6 carbon atoms. A monocyclic cycloalkyl radical having 3 to 6 carbon atoms is preferred. Examples which may be preferably mentioned are: cyclopropyl, cyclobutyl, cyclopentyl, cyclohexyl and cycloheptyl.

$(C_6-C_{10})$-Aryl is in the context of the invention an aromatic radical having preferably 6 to 10 carbon atoms. Preferred aryl radicals are phenyl and naphthyl.

$(C_1-C_6)$-Alkoxy and $(C_1-C_4)$-alkoxy are in the context of the invention a straight-chain or branched alkoxy radical having respectively 1 to 6 and 1 to 4 carbon atoms. A straight-chain or branched alkoxy radical having 1 to 4 carbon atoms is preferred. Examples which may be preferably mentioned are: methoxy, ethoxy, n-propoxy, isopropoxy and tert-butoxy.

Mono-$(C_1-C_6)$-alkylamino and mono-$(C_1-C_4)$-alkylamino are in the context of the invention an amino group having a straight-chain or branched alkyl substituent which have respectively 1 to 6 and 1 to 4 carbon atoms. A straight-chain or branched monoalkylamino radical having 1 to 4 carbon atoms is preferred. Examples which may be preferably mentioned are: methylamino, ethylamino, n-propylamino, isopropylamino and tert-butylamino.

Di-$(C_1-C_6)$-alkylamino and di-$(C_1-C_4)$-alkylamino are in the context of the invention an amino group having two identical or different straight-chain or branched alkyl substituents each of which have respectively 1 to 6 and 1 to 4 carbon atoms. Straight-chain or branched alkylamino radicals having in each case 1 to 4 carbon atoms are preferred. Examples which may be preferably mentioned are: N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino.

Mono- or di-$(C_1-C_6)$-alkylaminocarbonyl and mono- or di-$(C_1-C_4)$-alkylaminocarbonyl are in the context of the invention an amino group which is linked via a carbonyl group and which has respectively one straight-chain or branched or two identical or different straight-chain or branched alkyl substituents having in each case respectively 1 to 6 and 1 to 4 carbon atoms. Examples which may be preferably mentioned are: methylaminocarbonyl, ethylaminocarbonyl, isopropylaminocarbonyl, tert-butylaminocarbonyl, N,N-dimethylaminocarbonyl, N,N-diethylaminocarbonyl, N-ethyl-N-methylaminocarbonyl and N-tert-butyl-N-methylaminocarbonyl.

$(C_3-C_8)$-Cycloalkylamino and $(C_3-C_6)$-cycloalkylamino are in the context of the invention an amino group having a mono- or, where appropriate, bicyclic cycloalkyl substituent which has respectively 3 to 8 and 3 to 6 ring carbon atoms. A monocyclic cycloalkyl substituent having 3 to 6 ring carbon atoms is preferred. Examples which may be preferably mentioned are: cyclopropylamino, cyclobutylamino, cyclopentylamino, cyclohexylamino, cycloheptylamino and cyclooctylamino.

$(C_1-C_4)$-Alkylsulfonyl is in the context of the invention a straight-chain or branched alkylsulfonyl radical having 1 to 4 carbon atoms. A straight-chain or branched alkylsulfonyl radical having 1 to 3 carbon atoms is preferred. Examples which may be preferably mentioned are: methylsulfonyl, ethylsulfonyl, n-propylsulfonyl, isopropylsulfonyl, n-butylsulfonyl and tert-butylsulfonyl.

A 4- to 7-membered heterocycle is in the context of the invention a saturated or partially unsaturated heterocycle having 4 to 7 ring atoms, which comprises a ring nitrogen atom, and is linked via the latter and may comprise a further heteroatom from the series N, O, S, SO or $SO_2$. A 4- to 7-membered saturated N-linked heterocycle which may comprise a further heteroatom from the series N, O or S is preferred. Examples which may be preferably mentioned are: azetidinyl, pyrrolidinyl, pyrrolinyl, piperidinyl, piperazinyl, morpholinyl, thiomorpholinyl, azepinyl and 1,4-diazepinyl.

5- to 10-membered heteroaryl is in the context of the invention a mono- or, where appropriate, bicyclic aromatic heterocycle (heteroaromatic system) having up to four identical or different heteroatoms from the series N, O and/or S, which is linked via a ring carbon atom or, where appropriate, via a ring nitrogen atom of the heteroaromatic system. Examples which may be mentioned are: furyl, pyrrolyl, thienyl, pyrazolyl, imidazolyl, thiazolyl, oxazolyl, isoxazolyl, isothiazolyl, triazolyl, oxadiazolyl, thiadiazolyl, tetrazolyl, pyridyl, pyrimidinyl, pyridazinyl, pyrazinyl, triazinyl, benzofuranyl, benzothienyl, benzimidazolyl, benzoxazolyl, benzothiazolyl, benzotriazolyl, indolyl, indazolyl, quinolinyl, isoquinolinyl, naphthyridinyl, quinazolinyl, quinoxalinyl. Monocyclic 5- or 6-membered heteroaryl radicals having up to three heteroatoms from the series N, O and/or S are preferred, such as, for example, furyl, thienyl, thiazolyl, oxazolyl, isothiazolyl, isoxazolyl, pyrazolyl, imidazolyl, triazolyl, oxadiazolyl, thiadiazolyl, pyridyl, pyrimidinyl, pyridazinyl, pyrazinyl, triazinyl.

Halogen in the context of the invention includes fluorine, chlorine, bromine and iodine. Fluorine, chlorine or bromine are preferred.

If radicals in the compounds according to the invention are substituted, the radicals may, unless otherwise specified, be substituted one or more times. In the context of the present invention, all radicals which occur more than once have a mutually independent meaning. Substitution by one, two or three identical or different substituents is preferred. Substitution by one substituent is very particularly preferred.

Preference is given in the context of the present invention to compounds of the formula (I) in which $R^1$ is hydrogen, benzyloxy, ethoxy, n-propoxy or a group of the formula $R^8$—C(=O)—NH—, where ethoxy may be substituted in position 2, and n-propoxy in position 2 or 3, by $(C_1-C_4)$-alkoxy, amino, mono- or di-$(C_1-C_4)$-alkylamino, $(C_3-C_6)$-cycloalkylamino, N-$(C_3-C_6)$-cycloalkyl-N-$(C_1-C_4)$-alkylamino or by a 4- to 7-membered heterocycle which is bonded via an N atom,
where mono- and di-$(C_1-C_4)$-alkylamino in turn may be substituted by hydroxy, $(C_1-C_4)$-alkoxy, amino, mono- or di-$(C_1-C_4)$-alkylamino,
and in which
$R^8$ is 5- or 6-membered heteroaryl which may be substituted by $(C_1-C_4)$-alkyl or halogen, $R^2$ is hydrogen, ethoxy or n-propoxy, where ethoxy may be substituted in position 2, and n-propoxy in position 2 or 3, by $(C_1-C_4)$-alkoxy, amino, mono- or di-$(C_1-C_4)$-alkylamino, $(C_3-C_6)$-cycloalkylamino, N-$(C_3-C_6)$-cycloalkyl-N-$(C_1-C_4)$-alkylamino or by a 4- to 6-membered heterocycle which is bonded via an N atom,
where mono- and di-$(C_1-C_4)$-alkylamino in turn may be substituted by hydroxy, $(C_1-C_4)$-alkoxy, amino, mono- or di-$(C_1-C_4)$-alkylamino,
but where $R^1$ and $R^2$ are not simultaneously hydrogen, $R^3$ is hydroxy or amino
and
$R^4$ hydrogen,
or
$R^3$ and $R^4$ together with the carbon atom to which they are bonded form a group of the formula >C=O or >C=N—OH, $R^5$ is mono- or di-$(C_1-C_4)$-alkylaminocarbonyl, n is the number 0, 1, 2 or 3, $R^6$ is located in the meta or para position relative to the point of linkage of the phenyl ring to the tricycle, and is halogen, $(C_1-C_4)$-alkyl, $(C_1-C_4)$-alkoxy, $(C_6-C_{10})$-aryl, 5- to 6-membered heteroaryl or a group of the formula —$NR^9R^{10}$,
where aryl and heteroaryl in turn may each be substituted once to twice, identically or differently, by halogen, cyano, $(C_1-C_4)$-alkylsulfonyl or a group of the formula —$NR^9R^{10}$,
and in which
$R^9$ and $R^{10}$ are independently of one another hydrogen, $(C_1-C_4)$-alkyl, phenyl, benzyl or pyridylmethyl, or together with the nitrogen atom to which they are bonded form a 4 to 7-membered heterocycle,
and
$R^7$ is located in the meta or para position relative to the point of linkage of the phenyl ring to the tricycle, and in the ortho position relative to $R^6$, and is hydrogen, halogen, $(C_1-C_4)$-alkyl, $(C_1-C_4)$-alkoxy or a group of the formula —$NR^{11}R^{12}$, in which
$R^{11}$ and $R^{12}$ are independently of one another hydrogen, $(C_1-C_4)$-alkyl, phenyl, benzyl or pyridylmethyl, or together with the nitrogen atom to which they are bonded form a 4- to 7-membered heterocycle,
or
$R^6$ and $R^7$ together with the phenyl ring to which they are bonded form a group of the formula

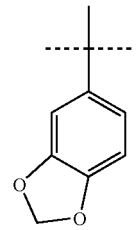

and the salts, solvates and solvates of the salts thereof.

Preference is likewise given in the context of the present invention to compounds of the formula (I) in which $R^1$ is hydrogen, benzyloxy, ethoxy, n-propoxy or a group of the formula $R^8$—C(=O)—NH—, where ethoxy may be substituted in position 2, and n-propoxy in position 2 or 3, by $(C_1-C_4)$-alkoxy, amino, mono- or di-$(C_1-C_4)$-alkylamino, $(C_3-C_6)$-cycloalkylamino, N-$(C_3-C_6)$-cycloalkyl-N-$(C_1-C_4)$-alkylamino or by a 4- to 7-membered heterocycle which is bonded via an N atom,
where mono- and di-$(C_1-C_4)$-alkylamino in turn may be substituted by hydroxy, $(C_1-C_4)$-alkoxy, amino, mono- or di-$(C_1-C_4)$-alkylamino,
and in which
$R^8$ is 5- or 6-membered heteroaryl which may be substituted by $(C_1-C_4)$-alkyl or halogen, $R^2$ is hydrogen, ethoxy or n-propoxy, where ethoxy may be substituted in position 2, and n-propoxy in position 2 or 3, by $(C_1-C_4)$-alkoxy, amino, mono- or di-$(C_1-C_4)$-alkylamino, $(C_3-C_6)$-cycloalkylamino, N-$(C_3-C_6)$-cycloalkyl-N-$(C_1-C_4)$-alkylamino or by a 4- to 7-membered heterocycle which is bonded via an N atom,
where mono- and di-$(C_1-C_4)$-alkylamino in turn may be substituted by hydroxy, $(C_1-C_4)$-alkoxy, amino, mono- or di-$(C_1-C_4)$-alkylamino,
but where $R^1$ and $R^2$ are not simultaneously hydrogen, $R^3$ is hydroxy or amino
and
$R^4$ is hydrogen,
or
$R^3$ and $R^4$ together with the carbon atom to which they are bonded form a group of the formula >C=O or >C=N—OH, $R^5$ is hydrogen, n is the number 0, 1, 2 or 3, $R^6$ is located in the meta or para position relative to the point of linkage of the phenyl ring to the tricycle, and is $(C_6-C_{10})$-aryl, 5- to 6-membered heteroaryl or a group of the formula —$NR^9R^{10}$,
where aryl and heteroaryl in turn may each be substituted once to twice, identically or differently, by halogen, cyano, $(C_1-C_4)$-alkylsulfonyl or a group of the formula —$NR^9R^{10}$,
and in which
$R^9$ and $R^{10}$ are independently of one another hydrogen, $(C_1-C_4)$-alkyl, phenyl, benzyl or pyridylmethyl, or together with the nitrogen atom to which they are bonded form a 4- to 7-membered heterocycle, and
R[7] is located in the meta or para position relative to the point of linkage of the phenyl ring to the tricycle, and in the ortho position relative to R[6], and is hydrogen, halogen, ($C_1$-$C_4$)-alkyl, ($C_1$-$C_4$)-alkoxy or a group of the formula —NR[11]R[12] in which R[11] and R[12] are independently of one another hydrogen, ($C_1$-$C_4$)-alkyl, phenyl, benzyl or pyridylmethyl, or together with the nitrogen atom to which they are bonded form a 4- to 7-membered heterocycle, or R[6] and R[7], together with the phenyl ring to which they are bonded form a group of the formula

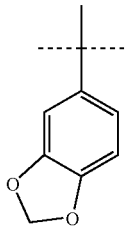

and the salts, solvates and solvates of the salts thereof.

Preference is likewise given in the context of the present invention to compounds of the formula (I) in which R[1] is hydrogen, benzyloxy, ethoxy, n-propoxy or a group of the formula R[8]—C(=O)—NH—, where ethoxy may be substituted in position 2, and n-propoxy in position 2 or 3, by ($C_1$-$C_4$)-alkoxy, amino, mono- or di-($C_1$-$C_4$)-alkylamino, ($C_3$-$C_6$)-cycloalkylamino, N-($C_3$-$C_6$)-cycloalkyl-N-($C_1$-$C_4$)-alkylamino or by a 4- to 7-membered heterocycle which is bonded via an N atom, where mono- and di-($C_1$-$C_4$)-alkylamino in turn may be substituted by hydroxy, ($C_1$-$C_4$)-alkoxy, amino, mono- or di-($C_1$-$C_4$)-alkylamino, and in which R[8] is 5- or 6-membered heteroaryl which may be substituted by ($C_1$-$C_4$)-alkyl or halogen, R[2] is hydrogen, ethoxy or n-propoxy, where ethoxy may be substituted in position 2, and n-propoxy in position 2 or 3, by ($C_1$-$C_4$)-alkoxy, amino, mono- or di-($C_1$-$C_4$)-alkylamino, ($C_3$-$C_6$)-cycloalkylamino, N-($C_3$-$C_6$)-cycloalkyl-N-($C_1$-$C_4$)-alkylamino or by a 4- to 7-membered heterocycle which is bonded via an N atom, where mono- and di-($C_1$-$C_4$)-alkylamino in turn may be substituted by hydroxy, ($C_1$-$C_4$)-alkoxy, amino, mono- or di-($C_1$-$C_4$)-alkylamino, but where R[1] and R[2] are not simultaneously hydrogen, R[3] is amino and R[4] is hydrogen, or R[3] and R[4] together with the carbon atom to which they are bonded form a group of the formula >C=N—OH, R[5] is hydrogen, n is the number 0, 1, 2 or 3, R[6] is located in the meta or para position relative to the point of linkage of the phenyl ring to the tricycle, and is halogen, ($C_1$-$C_4$)-alkyl or ($C_1$-$C_4$)-alkoxy, and R[7] is located in the meta or para position relative to the point of linkage of the phenyl ring to the tricycle, and in ortho position relative to R[6], and is hydrogen, halogen, ($C_1$-$C_4$)-alkyl, ($C_1$-$C_4$)-alkoxy or a group of the formula —NR[11]R[12] in which R[11] and R[12] are independently of one another hydrogen, ($C_1$-$C_4$)-alkyl, phenyl, benzyl or pyridylmethyl, or together with the nitrogen atom to which they are bonded form a 4- to 7-membered heterocycle, or R[6] and R[7] together with the phenyl ring to which they are bonded form a group of the formula

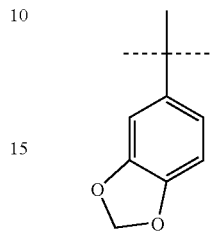

and the salts, solvates and solvates of the salts thereof.

Preference is likewise given in the context of the present invention to compounds of the formula (I) in which R[1] is hydrogen, benzyloxy, ethoxy, n-propoxy or a group of the formula R[8]—C(=O)—NH—, where ethoxy may be substituted in position 2, and n-propoxy in position 2 or 3, by ($C_1$-$C_4$)-alkoxy, amino, mono- or di-($C_1$-$C_4$)-alkylamino, ($C_3$-$C_6$)-cycloalkylamino, N-($C_3$-$C_6$)-cycloalkyl-N-($C_1$-$C_4$)-alkylamino or by a 4- to 7-membered heterocycle which is bonded via an N atom, where mono- and di-($C_1$-$C_4$)-alkylamino in turn may be substituted by hydroxy, ($C_1$-$C_4$)-alkoxy, amino, mono- or di-($C_1$-$C_4$)-alkylamino, and in which R[8] is 5- or 6-membered heteroaryl which may be substituted by ($C_1$-$C_4$)-alkyl or halogen, R[2] is hydrogen, ethoxy or n-propoxy, where ethoxy may be substituted in position 2, and n-propoxy in position 2 or 3, by ($C_1$-$C_4$)-alkoxy, amino, mono- or di-($C_1$-$C_4$)-alkylamino, ($C_3$-$C_6$)-cycloalkylamino, N-($C_3$-$C_6$)-cycloalkyl-N-($C_1$-$C_4$)-alkylamino or by a 4- to 7-membered heterocycle which is bonded via an N atom, where mono- and di-($C_1$-$C_4$)-alkylamino in turn may be substituted by hydroxy, ($C_1$-$C_4$)-alkoxy, amino, mono- or di-($C_1$-$C_4$)-alkylamino, but where R[1] and R[2] are not simultaneously hydrogen, R[3] is hydroxy and R[4] is hydrogen, or R[3] and R[4] together with the carbon atom to which they are bonded form a group of the formula >C=O, R[5] is hydrogen, n is the number 0, 1, 2 or 3, R[6] is located in the meta or para position relative to the point of linkage of the phenyl ring to the tricycle, and is halogen, ($C_1$-$C_4$)-alkyl or ($C_1$-$C_4$)-alkoxy, and R[7] is located in the meta or para position relative to the point of linkage of the phenyl ring to the tricycle, and in the ortho position relative to R[6], and is hydrogen, halogen, ($C_1$-$C_4$)-alkyl, ($C_1$-$C_4$)-alkoxy or a group of the formula —NR[11]R[12] in which R[11] and R[12] are independently of one another hydrogen, ($C_1$-$C_4$)-alkyl, phenyl, benzyl or pyridylmethyl or together with the nitrogen atom to which they are bonded form a 4- to 7-membered heterocycle, or $R^6$ and $R^7$ together with the phenyl ring to which they are bonded form a group of the formula

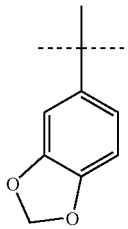

and the salts, solvates and solvates of the salts thereof.

Preference is likewise given in the context of the present invention to compounds of the formula (I) in which $R^1$ is ethoxy, n-propoxy or a group of the formula $R^8$—C(=O)—NH—, where ethoxy is substituted in position 2, and n-propoxy in position 2 or 3, by ($C_1$-$C_4$)-alkoxy, amino, mono- or di-($C_1$-$C_4$)-alkylamino, ($C_3$-$C_6$)-cycloalkylamino, N-($C_3$-$C_6$)-cycloalkyl-N-($C_1$-$C_4$)-alkylamino or by a 4- to 7-membered heterocycle which is bonded via an N atom, where mono- and di-($C_1$-$C_4$)-alkylamino in turn may be substituted by hydroxy, ($C_1$-$C_4$)-alkoxy, amino, mono- or di-($C_1$-$C_4$)-alkylamino, and in which $R^8$ is a 5- or 6-membered heteroaryl which may be substituted by ($C_1$-$C_4$)-alkyl or halogen, $R^2$ is ethoxy or n-propoxy, where ethoxy is substituted in position 2, and n-propoxy in position 2 or 3, by ($C_1$-$C_4$)-alkoxy, amino, mono- or di-($C_1$-$C_4$)-alkylamino, ($C_3$-$C_6$)-cycloalkylamino, N-($C_3$-$C_6$)-cycloalkyl-N-($C_1$-$C_4$)-alkylamino or by a 4- to 7-membered heterocycle which is bonded via an N atom, where mono- and di-($C_1$-$C_4$)-alkylamino in turn may be substituted by hydroxy, ($C_1$-$C_4$)-alkoxy, amino, mono- or di-($C_1$-$C_4$)-alkylamino, $R^3$ is hydroxy and $R^4$ is hydrogen, or $R^3$ and $R^4$ together with the carbon atom to which they are bonded form a group of the formula >C=O, $R^5$ is hydrogen, n is the number 0, 1, 2 or 3, $R^6$ is located in the meta or para position relative to the point of linkage of the phenyl ring to the tricycle, and is halogen, ($C_1$-$C_4$)-alkyl or ($C_1$-$C_4$)-alkoxy, and $R^7$ is located in the meta or para position relative to the point of linkage of the phenyl ring to the tricycle, and in the ortho position relative to $R^6$, and is hydrogen, halogen, ($C_1$-$C_4$)-alkyl, ($C_1$-$C_4$)-alkoxy or a group of the formula —$NR^{11}R^{12}$ in which $R^{11}$ and $R^{12}$ are independently of one another hydrogen, ($C_1$-$C_4$)-alkyl, phenyl, benzyl or pyridylmethyl, or together with the nitrogen atom to which they are bonded form a 4- to 7-membered heterocycle, or $R^6$ and $R^7$ together with the phenyl ring to which they are bonded form a group of the formula

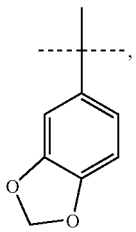

and the salts, solvates and solvates of the salts thereof.

Particular preference is given in the context of the present invention to compounds of the formula (I) in which $R^1$ and $R^2$ are independently of one another hydrogen, ethoxy or n-propoxy, where ethoxy is substituted in position 2, and n-propoxy in position 3, by methoxy, ethoxy, amino, methylamino, ethylamino, isopropylamino, dimethylamino, diethylamino, cyclopropylamino, N-cyclopropyl-N-methylamino, azetidino or pyrrolidino, but where $R^1$ and $R^2$ are not simultaneously hydrogen, $R^3$ is hydroxy or amino, $R^4$ is hydrogen, $R^5$ is methylaminocarbonyl or dimethylaminocarbonyl, n is the number 0 or 1, $R^6$ is located in the para position relative to the point of linkage of the phenyl ring to the tricycle, and is fluorine, chlorine, bromine, methyl, ethyl, methoxy or ethoxy, and $R^7$ is hydrogen, and the salts, solvates and solvates of the salts thereof.

Particular preference is likewise given in the context of the present invention to compounds of the formula (I) in which $R^1$ is hydrogen, ethoxy, n-propoxy or a group of the formula $R^8$—C(=O)—NH—, where ethoxy may be substituted in position 2, and n-propoxy in position 3, by methoxy, ethoxy, amino, methylamino, ethylamino, isopropylamino, dimethylamino, diethylamino, cyclopropylamino, N-cyclopropyl-N-methylamino, azetidino or pyrrolidino, in which $R^8$ is pyridyl, pyrrolyl, imidazolyl, pyrazolyl, triazolyl or thiadiazolyl, each of which may be substituted by methyl, ethyl, fluorine or chlorine, $R^2$ is hydrogen, ethoxy or n-propoxy, where ethoxy may be substituted in position 2, and n-propoxy in position 3, by methoxy, ethoxy, amino, methylamino, ethylamino, isopropylamino, dimethylamino, diethylamino, cyclopropylamino, N-cyclopropyl-N-methylamino, azetidino or pyrrolidino, but where $R^1$ and $R^2$ are not simultaneously hydrogen, $R^3$ is hydroxy or amino, $R^4$ is hydrogen, $R^5$ is hydrogen, n is the number 0 or 1, $R^6$ is located in the meta or para position relative to the point of linkage of the phenyl ring to the tricycle, and is phenyl, thienyl, indolyl, quinoxalinyl or a group of the formula —$NR^9R^{10}$, where phenyl, thienyl and indolyl in turn may each be substituted once to twice, identically or differently, by fluorine, chlorine, bromine, cyano or amino, and in which $R^9$ and $R^{10}$ are independently of one another hydrogen, methyl, ethyl, benzyl or pyridylmethyl, or together with the nitrogen atom to which they are bonded form a pyrrolidino ring, and R[7] is hydrogen, and the salts, solvates and solvates of the salts thereof.

Particular preference is likewise given in the context of the present invention to compounds of the formula (I) in which R[1] is hydrogen, ethoxy, n-propoxy or a group of the formula R[8]—C(=O)—NH—, where ethoxy may be substituted in position 2, and n-propoxy in position 3, by methoxy, ethoxy, amino, methylamino, ethylamino, isopropylamino, dimethylamino, diethylamino, cyclopropylamino, N-cyclopropyl-N-methylamino, azetidino or pyrrolidino, in which R[8] is pyridyl, pyrrolyl, imidazolyl, pyrazolyl, triazolyl or thiadiazolyl, each of which may be substituted by methyl, ethyl, fluorine or chlorine, R[2] is hydrogen, ethoxy or n-propoxy, where ethoxy may be substituted in position 2, and n-propoxy in position 3, by methoxy, ethoxy, amino, methylamino, ethylamino, isopropylamino, dimethylamino, diethylamino, cyclopropylamino, N-cyclopropyl-N-methylamino, azetidino or pyrrolidino, but where R[1] and R[2] are not simultaneously hydrogen, R[3] is amino, R[4] is hydrogen, R[5] is hydrogen, n is the number 0 or 1, R[6] is located in the meta or para position relative to the point of linkage of the phenyl ring to the tricycle, and is fluorine, chlorine, bromine, methyl, ethyl, methoxy or ethoxy, and R[7] is located in the meta or para position relative to the point of linkage of the phenyl ring to the tricycle, and in the ortho position relative to R[6], and is hydrogen, fluorine, chlorine, bromine, methyl, ethyl, methoxy, ethoxy or a group of the formula —NR[11]R[12] in which R[11] and R[12] are independently of one another hydrogen, methyl, ethyl, benzyl or pyridylmethyl, or together with the nitrogen atom to which they are bonded form a pyrrolidino or piperidino ring, or R[6] and R[7] together with the phenyl ring to which they are bonded form a group of the formula

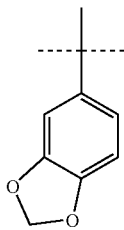

and the salts, solvates and solvates of the salts thereof.

Particular preference is likewise given in the context of the present invention to compounds of the formula (I) in which R[1] is hydrogen, ethoxy, n-propoxy or a group of the formula R[8]—C(=O)—NH—, where ethoxy may be substituted in position 2, and n-propoxy in position 3, by methoxy, ethoxy, amino, methylamino, ethylamino, isopropylamino, dimethylamino, diethylamino, cyclopropylamino, N-cyclopropyl-N-methylamino, azetidino or pyrrolidino, in which R[8] is pyridyl, pyrrolyl, imidazolyl, pyrazolyl, triazolyl or thiadiazolyl, each of which may be substituted by methyl, ethyl, fluorine or chlorine, R[2] is hydrogen, ethoxy or n-propoxy, where ethoxy may be substituted in position 2, and n-propoxy in position 3, by methoxy, ethoxy, amino, methylamino, ethylamino, isopropylamino, dimethylamino, diethylamino, cyclopropylamino, N-cyclopropyl-N-methylamino, azetidino or pyrrolidino, where R[1] or R[2] is hydrogen, but both are not simultaneously hydrogen, R[3] is hydroxy and R[4] is hydrogen, or R[3] and R[4] together with the carbon atom to which they are bonded form a group of the formula >C=O, R[5] is hydrogen, n is the number 0 or 1, R[6] is located in the meta or para position relative to the point of linkage of the phenyl ring to the tricycle, and is fluorine, chlorine, bromine, methyl, ethyl, methoxy or ethoxy, and R[7] is located in the meta or para position relative to the point of linkage of the phenyl ring to the tricycle, and in the ortho position relative to R[6], and is hydrogen, fluorine, chlorine, bromine, methyl, ethyl, methoxy, ethoxy or a group of the formula —NR[11]R[12] in which R[11] and R[12] are independently of one another hydrogen, methyl, ethyl, benzyl or pyridylmethyl, or together with the nitrogen atom to which they are bonded form a pyrrolidino or piperidino ring, or R[6] and R[7] together with the phenyl ring to which they are bonded form a group of the formula

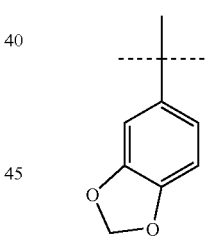

and the salts, solvates and solvates of the salts thereof.

Particular preference is likewise given in the context of the present invention to compounds of the formula (I) in which R[1] is ethoxy, n-propoxy or a group of the formula R[8]—C(=O)—NH—, where ethoxy is substituted in position 2, and n-propoxy in position 3, by methoxy, ethoxy, amino, methylamino, ethylamino, isopropylamino, dimethylamino, diethylamino, cyclopropylamino, N-cyclo-propyl-N-methylamino, azetidino or pyrrolidino, in which R[8] is pyridyl, pyrrolyl, imidazolyl, pyrazolyl, triazolyl or thiadiazolyl, each of which may be substituted by methyl, ethyl, fluorine or chlorine, R[2] is ethoxy or n-propoxy, where ethoxy is substituted in position 2, and n-propoxy in position 3, by methoxy, ethoxy, amino, methylamino, ethylamino, isopropylamino, dimethylamino, diethylamino, cyclopropylamino, N-cyclopropyl-N-methylamino, azetidino or pyrrolidino, $R^3$ is hydroxy and $R^4$ is hydrogen, or $R^3$ and $R^4$ together with the carbon atom to which they are bonded form a group of the formula >C=O, $R^5$ is hydrogen, n is the number 0 or 1, $R^6$ is located in the meta or para position relative to the point of linkage of the phenyl ring to the tricycle, and is fluorine, chlorine, bromine, methyl, ethyl, methoxy or ethoxy, and $R^7$ is located in the meta or para position relative to the point of linkage of the phenyl ring to the tricycle, and in the ortho position relative to $R^6$, and is hydrogen, fluorine, chlorine, bromine, methyl, ethyl, methoxy, ethoxy or a group of the formula —$NR^{11}R^{12}$ in which $R^{11}$ and $R^{12}$ are independently of one another hydrogen, methyl, ethyl, benzyl or pyridylmethyl, or together with the nitrogen atom to which they are bonded form a pyrrolidino or piperidino ring, or $R^6$ and $R^7$ together with the phenyl ring to which they are bonded form a group of the formula

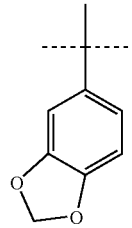

and the salts, solvates and solvates of the salts thereof.

The definitions of radicals indicated specifically in the respective combinations or preferred combinations for the radicals are replaced as desired irrespective of the particular combinations indicated for the radicals also by definitions of radicals of other combinations.

Combinations of two or more of the abovementioned preferred ranges are very particularly preferred.

The compounds according to the invention of the formula (I) in which $R^5$ is hydrogen can in principle be prepared by the processes described in WO 00/08007. The content of WO 00/08007, especially pages 14-26, is hereby expressly included as part of the disclosure. Depending on the specific meaning of the substituents in (I), in particular of $R^1$ and $R^2$, however, individual process stages described in WO 00/08007 are in some cases associated with only very low yields. The present invention therefore further relates to a novel process for preparing the compounds according to the invention of the formula (I) in which $R^5$ is hydrogen, characterized in that either

[A] Compounds of the Formula (II)

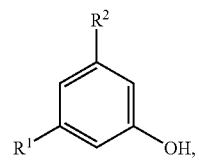

(II)

in which $R^1$ and $R^2$ each have the meaning indicated above, are reacted in an inert solvent in the presence of a base with a compound of the formula (III)

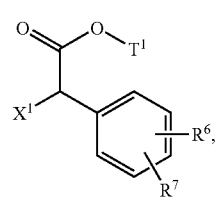

(III)

in which $R^6$ and $R^7$ each have the meaning indicated above, $X^1$ is a suitable leaving group such as, for example, halogen, mesylate, tosylate or triflate and $T^1$ is $(C_1$-$C_4)$-alkyl, to give compounds of the formula (IV)

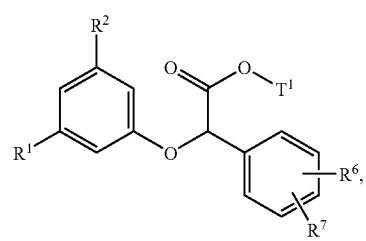

(IV)

in which $R^1$, $R^2$, $R^6$, $R^7$ and $T^1$ each have the meaning indicated above, subsequently converted by basic or acidic hydrolysis into carboxylic acids of the formula (V)

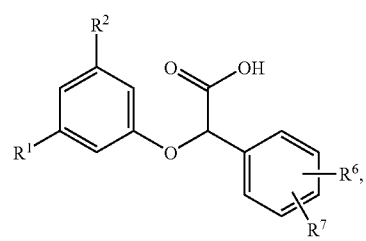

(V)

in which $R^1$, $R^2$, $R^6$ and $R^7$ each have the meaning indicated above, the latter are then cyclized after activation with phosphoryl chloride in the presence of a Lewis acid to compounds of the formula (VI)

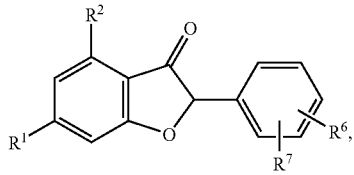
(VI)

in which $R^1$, $R^2$, $R^6$ and $R^7$ each have the meaning indicated above, or

[B] Compounds of the Formula (VII)

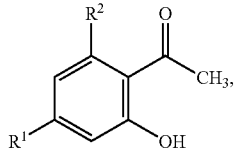
(VII)

in which $R^1$ and $R^2$ each have the meaning indicated above, are initially converted by conventional methods into phenacyl bromides of the formula (VIII)

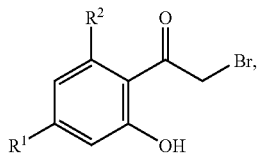
(VIII)

in which $R^1$ and $R^2$ each have the meaning indicated above, and the latter are then cyclized in the presence of a base to compounds of the formula (IX)

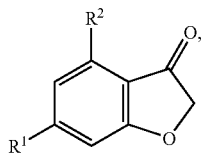
(IX)

in which $R^1$ and $R^2$ each have the meaning indicated above, subsequently brominated in an inert solvent to give compounds of the formula (X)

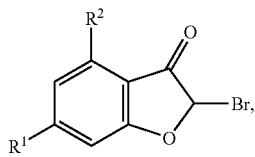
(X)

in which $R^1$ and $R^2$ each have the meaning indicated above, and converted by conventional methods into silyl enol ethers of the formula (XI)

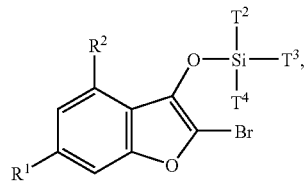
(XI)

in which $R^1$ and $R^2$ each have the meaning indicated above and $T^2$, $T^3$ and $T^4$ are identical or different and are each ($C_1$-$C_4$)-alkyl or phenyl, subsequently reacted in an inert solvent in the presence of a suitable palladium catalyst and of a base with a compound of the formula (XII)

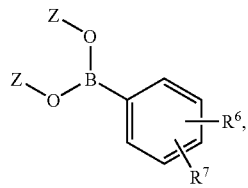
(XII)

in which $R^6$ and $R^7$ each have the meaning indicated above and

Z is hydrogen or methyl, or the two Z groups together form a $CH_2CH_2$— or $C(CH_3)_2$—$C(CH_3)_2$ bridge, to give compounds of the formula (XIII)

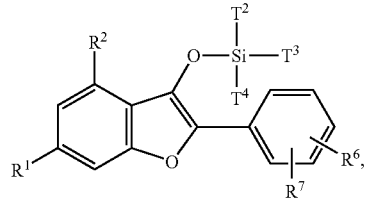
(XIII)

in which $R^1$, $R^2$, $R^6$, $R^7$, $T^2$, $T^3$ and $T^4$ each have the meaning indicated above, the silyl group is subsequently eliminated again by conventional methods to give compounds of the formula (VI), and the compounds of the formula (VI) resulting in each case are then converted in an inert solvent in the presence of a base by the process described in WO 00/08007 with a cinnamaldehyde of the formula (XIV)

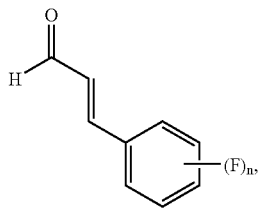

(XIV)

in which n has the meaning indicated above,
into compounds of the formula (XV)

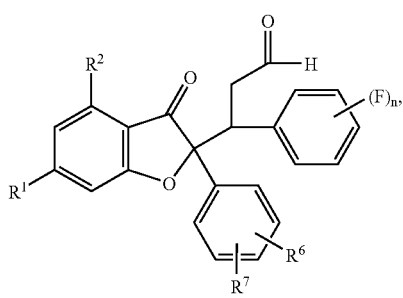

(XV)

in which $R^1$, $R^2$, $R^6$, $R^7$ and n each have the meaning indicated above, and the latter are then reacted further by the reaction sequence described in WO 00/08007, and the compounds of the formula (I) are where appropriate reacted with the appropriate (i) solvents and/or (ii) bases or acids to give the solvates, salts and/or solvates of the salts thereof.

Process step (VII)→(IX) can also be carried out in a three-stage one-pot process via the silyl enol ethers of the formula (XVI)

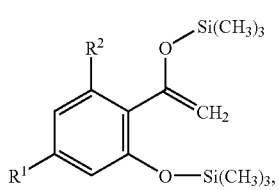

(XVI)

in which $R^1$ and $R^2$ each have the meaning indicated above and which can be obtained from (VII) by conventional methods, bromination thereof with N-bromosuccinimide, and subsequent cyclization to (IX) in the presence of sodium hydroxide solution.

The compounds of the formulae (II), (III), (VII), (XII) and (XIV) are commercially available, disclosed in the literature or can be prepared in analogy to processes disclosed in the literature.

Inert solvents for process step (II)+(III)→(IV) are for example halohydrocarbons such as dichloromethane, trichloromethane, tetrachloromethane, trichloroethane, tetrachloroethane, 1,2-dichloroethane or trichloroethylene, ethers such as diethyl ether, dioxane, tetrahydrofuran, glycol dimethyl ether or diethylene glycol dimethyl ether, hydrocarbons such as benzene, toluene, xylene, hexane, cyclohexane or petroleum fractions, or other solvents such as ethyl acetate, acetone, 2-butanone, dimethylformamide, dimethyl sulfoxide, pyridine or acetonitrile. It is likewise possible to employ mixtures of the solvents mentioned. 2-Butanone, diethyl ether, dioxane, tetrahydrofuran, dichloromethane, toluene or benzene are preferred.

Bases suitable for process step (II)+(III)→(IV) are the usual inorganic or organic bases. These preferably include alkali metal hydroxides such as, for example, lithium, sodium or potassium hydroxide, alkali metal or alkaline earth metal carbonates or bicarbonates, such as lithium, sodium, potassium, calcium or cesium carbonate, or sodium or potassium bicarbonate, alkali metal hydrides such as sodium hydride, amides such as sodium amide, lithium bis(trimethylsilyl)amide or lithium diisopropylamide, or organic amines such as pyridine, triethylamine, ethyldiisopropylamine, N-methylmorpholine or N-methylpiperidine. Sodium or potassium hydroxide, sodium or potassium carbonate or sodium hydride are particularly preferred.

Process step (II)+(III)→(IV) is generally carried out in a temperature range from +20° C. to +160° C., preferably from +60° C. to +100° C. The reaction can be carried out under atmospheric, elevated or reduced pressure (e.g. from 0.5 to 5 bar). It is generally carried out under atmospheric pressure.

Inert solvents for process step (IV)→(V) are for example water, alcohols such as methanol, ethanol, n-propanol, isopropanol or n-butanol, hydrocarbons such as benzene or other solvents such as acetone, dimethylformamide, dimethyl sulfoxide or acetonitrile. It is likewise possible to employ mixtures of the solvents mentioned. Methanol, ethanol, n-propanol and/or water are preferred.

Bases suitable for process step (IV)→(V) are the usual inorganic bases. These preferably include alkali metal hydroxides such as, for example, lithium, sodium or potassium hydroxide, alkali metal or alkaline earth metal carbonates such as lithium, sodium, potassium calcium carbonate, or alkali metal alcoholates such as sodium or potassium methanolate, or sodium or potassium ethanolate or potassium tert-butoxide. Sodium or potassium hydroxide or sodium or potassium carbonate are particularly preferred.

Acids suitable for process step (IV)→(V) are in general sulfuric acid, hydrogen chloride/hydrochloric acid, hydrogen bromide/hydrobromic acid, phosphoric acid, acetic acid, trifluoroacetic acid, toluenesulfonic acid, methanesulfonic acid or trifluoromethanesulfonic acid or mixtures thereof, where appropriate with addition of water. Hydrogen chloride or trifluoroacetic acid in the case of tert-butyl esters, and hydrochloric acid or sulfuric acid in the case of methyl esters, are preferred.

Process step (IV)→(V) is generally carried out in a temperature range from 0° C. to +100° C., preferably from +40° C. to +80° C. The reaction can be carried out under atmospheric, elevated or reduced pressure (e.g. from 0.5 to 5 bar). It is generally carried out under atmospheric pressure.

Process step (V)→(VI) is preferably carried out without further solvent. Lewis acids suitable for this process step are the usual inorganic Lewis acids such as, for example, aluminum trichloride, iron trichloride, boron trifluoride, boron trichloride, boron tribromide, titanium tetrachloride, titanium trichloride, tin dichloride, tin tetrachloride or zinc dichloride. Zinc dichloride is preferred.

Process step (V)→(VI) is generally carried out in a temperature range from 0° C. to +100° C., preferably from 0° C. to +40° C. The reaction can be carried out under atmospheric, elevated or reduced pressure (e.g. from 0.5 to 5 bar). It is generally carried out under atmospheric pressure.

Inert solvents for process steps (VII)→(VIII) and (IX)→(X) are for example halohydrocarbons such as dichloromethane, trichloromethane, tetrachloromethane, trichloroethane, tetrachloroethane, 1,2-dichloroethane or trichloroethylene, ethers such as diethyl ether, dioxane, tetrahydrofuran, glycol dimethyl ether or diethylene glycol dimethyl ether, hydrocarbons such as hexane or cyclohexane, or other solvents such as ethyl acetate, dimethylformamide or dimethyl sulfoxide. It is likewise possible to employ mixtures of the solvents mentioned. Diethyl ether, dioxane, tetrahydrofuran, ethyl acetate, trichloromethane and/or tetrachloromethane are preferred.

Brominating agents suitable for process steps (VII)→(VIII) and (IX)→(X) are the usual inorganic or organic reagents. These preferably include bromine, N-bromosuccinimide, copper dibromide, pyridine hydrotribromide, dimethylbenzylammonium tribromide or phenyltrimethylammonium tribromide. Bromine and copper dibromide are particularly preferred.

Process steps (VII)→(VIII) and (IX)→(X) are generally carried out in a temperature range from −20° C. to +150° C., preferably from 0° C. to +80° C. The reaction can be carried out under atmospheric, elevated or reduced pressure (e.g. from 0.5 to 5 bar). It is generally carried out under atmospheric pressure.

Inert solvents for process step (VIII)→(IX) are for example water, alcohols such as methanol, ethanol, n-propanol, isopropanol, n-butanol or tert-butanol, halohydrocarbons such as dichloromethane, trichloromethane, tetrachloromethane, trichloroethane, tetrachloroethane, 1,2-dichloroethane or trichloroethylene, ethers such as diethyl ether, dioxane, tetrahydrofuran, glycol dimethyl ether or diethylene glycol dimethyl ether, hydrocarbons such as benzene, toluene, xylene, hexane, cyclohexane or petroleum fractions, or other solvents such as dimethylformamide, dimethyl sulfoxide, pyridine or acetonitrile. It is likewise possible to employ mixtures of the solvents mentioned. Methanol, ethanol, water and/or tetrahydrofuran are preferred.

Bases suitable for process step (VIII)→(IX) are the usual inorganic or organic bases. These preferably include alkali metal hydroxides such as lithium, sodium or potassium hydroxide, alkali metal or alkaline earth metal carbonates or bicarbonates, such as lithium, sodium, potassium, calcium or cesium carbonate, or sodium or potassium bicarbonate, alkali metal alcoholates such as sodium or potassium methanolate, sodium or potassium ethanolate or potassium tert-butoxide, alkali metal acetates such as sodium or potassium acetate, alkali metal hydrides such as sodium hydride, amides such as sodium amide, lithium bis(trimethylsilyl)amide or lithium diisopropylamide, or organic amides such as pyridine, triethylamine, ethyldiisopropylamine, N-methylmorpholine or N-methylpiperidine. Sodium or potassium hydroxide or sodium acetate are particularly preferred.

Process step (VIII)→(IX) is generally carried out in a temperature range from 0° C. to +100° C., preferably from +20° C. to +80° C. The reaction can be carried out under atmospheric, elevated or reduced pressure (e.g. from 0.5 to 5 bar). It is generally carried out under atmospheric pressure.

Inert solvents for process step (X)→(XI) are for example halohydrocarbons such as dichloromethane, trichloromethane, tetrachloromethane, trichloroethane, tetrachloroethane, 1,2-dichloroethane or trichloroethylene, ethers such as diethyl ether, dioxane, tetrahydrofuran, glycol dimethyl ether or diethylene glycol dimethyl ether, hydrocarbons such as benzene, toluene, xylene, hexane, cyclohexane or petroleum fractions, or other solvents such as dimethylformamide, dimethyl sulfoxide, pyridine or acetonitrile. It is likewise possible to employ mixtures of the solvents mentioned. Toluene, hexane, diethyl ether or tetrahydrofuran are preferred.

Bases suitable for process step (X)→(XI) are the usual inorganic or organic bases. These preferably include alkali metal hydrides such as sodium hydride, amides such as sodium amide, lithium bis(trimethylsilyl)amide or lithium diisopropylamide, or organic amines such as pyridine, triethylamine, ethyldiisopropylamine, N-methylmorpholine or N-methylpiperidine. Lithium diisopropylamide, triethylamine or ethyldiisopropylamine are particularly preferred.

Process step (X)→(XI) is generally carried out in a temperature range from −20° C. to +50° C., preferably from 0° C. to +30° C. The reaction can be carried out under atmospheric, elevated or reduced pressure (e.g. from 0.5 to 5 bar). It is generally carried out under atmospheric pressure.

Inert solvents for process step (XI)+(XII)→(XIII) are for example halohydrocarbons such as dichloromethane, trichloromethane, tetrachloromethane, trichloroethane, tetrachloroethane, 1,2-dichloroethane or trichloroethylene, ethers such as diethyl ether, dioxane, tetrahydrofuran, glycol dimethyl ether or diethylene glycol dimethyl ether, alcohols such as methanol, ethanol, n-propanol, isopropanol, n-butanol or tert-butanol, hydrocarbons such as benzene, toluene, xylene, hexane, cyclohexane or petroleum fractions, or other solvents such as ethyl acetate, acetone, water, dimethylformamide, dimethyl sulfoxide, pyridine or acetonitrile. It is likewise possible to employ mixtures of the solvents mentioned. Toluene, tetrahydrofuran, dioxane or dimethylformamide are preferred.

Bases suitable for process step (XI)+(XII)→(XIII) are the usual inorganic or organic bases. These preferably include alkali metal hydroxides such as, for example, lithium, sodium or potassium hydroxide, alkali metal, alkaline earth metal or heavy metal carbonates such as silver, thallium, lithium, sodium, potassium, cesium or calcium carbonate, alkali metal or alkaline earth metal bicarbonates such as sodium or potassium bicarbonate, alkali metal alcoholates such as sodium or potassium methanolate, sodium or potassium ethanolate or lithium, sodium or potassium tert-butoxide, alkali metal hydrides such as sodium hydride, amides such as sodium amide, lithium or sodium bis(trimethylsilyl)amide or lithium diisopropylamide, or organic amines such as pyridine, triethylamine, ethyldiisopropylamine, 1,5-diazabicyclo[5.4.0]undec-5-ene (DBU), N-methylmorpholine or N-methylpiperidine. Cesium or sodium carbonate, sodium hydride, potassium tert-butoxide, lithium diisopropylamide, DBU, triethylamine or ethyldiisopropylamine are particularly preferred.

Catalysts suitable for process step (XI)+(XII)→(XIII) are the palladium catalysts usual for Suzuki reaction conditions. Catalysts such as, for example, dichlorobis(triphenylphosphine)palladium, tetrakis(triphenylphosphine)palladium(0), palladium(II) acetate or bis(diphenylphosphaneferrocenyl)palladium(II) chloride are preferred. Suitable catalyst ligands are preferably the ligands usual for Suzuki reactions, such as, for example, triphenylphosphine, tri(o-tolyl)phosphine, tributylphosphine, 2,2'-bis(diphenylphosphino)-1,1'-binaphthyl (BINAP), 1,1'-bis(diphenylphosphino)ferrocene (dppf) or 1,3-bis(diphenylphosphino)propane (dppp).

Process step (XI)+(XII)→(XIII) is generally carried out in a temperature range from +20° C. to +200° C., preferably from +50° C. to +150° C. The reaction can be carried out under atmospheric, elevated or reduced pressure (e.g. from 0.5 to 5 bar). It is generally carried out under atmospheric pressure.

Inert solvents for process step (XIII)→(VI) are for example halohydrocarbons such as dichloromethane, trichloromethane, tetrachloromethane, trichloroethane, tetrachloroethane, 1,2-dichloroethane or trichloroethylene, ethers such as diethyl ether, dioxane, tetrahydrofuran, glycol dimethyl ether or diethylene glycol dimethyl ether, alcohols such as methanol, ethanol, n-propanol, isopropanol, n-butanol or tert-butanol, hydrocarbons such as benzene, toluene, xylene, hexane or cyclohexane, or other solvents such as dimethylformamide, dimethyl sulfoxide, acetonitrile or water. It is likewise possible to employ mixtures of the solvents mentioned. Methanol, ethanol, water, tetrahydrofuran or dioxane are preferred.

Elimination of the silyl group in process step (XIII)→(VI) can be carried out by the usual methods alternatively with the aid of a base or with the aid of an acid. Suitable bases are preferably tetrabutylammonium fluoride, pyridine or triethylamine, and preferred acids are hydrogen fluoride, hydrogen chloride/hydrochloric acid, formic acid, acetic acid, trifluoroacetic acid or toluenesulfonic acid.

Process step (XIII)→(VI) is generally carried out in a temperature range from −80° C. to +100° C., preferably from 0° C. to +80° C. The reaction can be carried out under atmospheric, elevated or reduced pressure (e.g. from 0.5 to 5 bar). It is generally carried out under atmospheric pressure.

The compounds according to the invention of the formula (I) in which $R^5$ is mono- or di-$(C_1-C_6)$-alkylaminocarbonyl can be prepared by initially converting compounds of the formula (XVII)

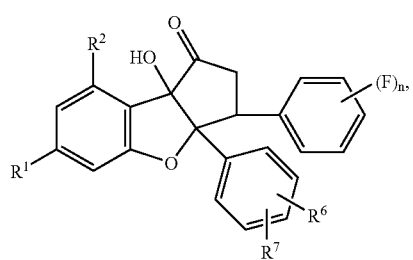

in which $R^1$, $R^2$, $R^6$, $R^7$ and n each have the meaning indicated above, in an inert solvent with methoxymagnesium methyl carbonate [M. Stiles, *J. Amer. Chem. Soc.* 81, 2598 (1959)] into carboxylic acids of the formula (XVIII)

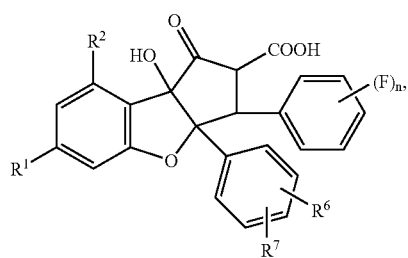

in which $R^1$, $R^2$, $R^6$, $R^7$ and n each have the meaning indicated above, subsequently reacted in the presence of a condensing agent and of a base with a compound of the formula (XIX)

$$HNR^{13}R^{14} \qquad (XIX),$$

in which
$R^{13}$ is hydrogen or $(C_1-C_6)$-alkyl
and
$R^{14}$ is $(C_1-C_6)$-alkyl,
to give compounds of the formula (XX)

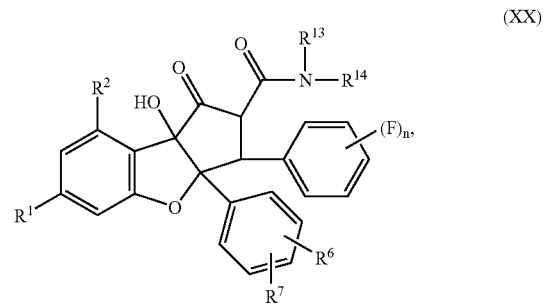

in which $R^1$, $R^2$, $R^6$, $R^7$, $R^{13}$, $R^{14}$ and n each have the meaning indicated above, and then further converting the latter where appropriate by the reaction sequences described in WO 00/08007.

The compounds of the formula (XVII) can be obtained by the processes described above or in WO 00/08007. The compounds of the formula (XIX) are commercially available or disclosed in the literature.

Inert solvents for process step (XVII)→(XVIII) are for example halohydrocarbons such as dichloromethane, trichloromethane, tetrachloromethane, trichloroethane, tetrachloroethane, 1,2-dichloroethane or trichloroethylene, ethers such as diethyl ether, dioxane, tetrahydrofuran, glycol dimethyl ether or diethylene glycol dimethyl ether, or other solvents such as dimethylformamide, dimethyl sulfoxide or acetonitrile. It is likewise possible to employ mixtures of the solvents mentioned. Dimethylformamide is preferred.

Process step (XVII)→(XVIII) is generally carried out in a temperature range from 0° C. to +200° C., preferably from +50° C. to +150° C. The reaction can be carried out under atmospheric, elevated or reduced pressure (e.g. from 0.5 to 5 bar). It is generally carried out under atmospheric pressure.

Inert solvents for process step (XVIII)+(XIX)→(XX) are for example halohydrocarbons such as dichloromethane, trichloromethane, tetrachloromethane, trichloroethane, tetrachloroethane, 1,2-dichloroethane or trichloroethylene, ethers such as diethyl ether, methyl tert-butyl ether, dioxane, tetrahydrofuran, glycol dimethyl ether or diethylene glycol dimethyl ether, hydrocarbons such as benzene, toluene, xylene, hexane, cyclohexane or petroleum fractions, or other solvents such as ethyl acetate, acetone, 2-butanone, dimethylformamide, dimethylacetamide, dimethyl sulfoxide, acetonitrile, N-methylpyrrolidine or pyridine. It is likewise possible to employ mixtures of the solvents mentioned. Dimethylformamide and tetrahydrofuran are preferred.

Condensing agents suitable for the amide formation in process step (XVIII)+(XIX)→(XX) are for example carbodiimides such as N,N'-diethyl-, N,N'-dipropyl-, N,N'-diisopropyl-, N,N'-dicyclohexylcarbodiimide (DCC), N-(3-dimethylaminoisopropyl)-N'-ethylcarbodiimide hydrochloride (EDC), N-cyclohexylcarbodiimide-N'-propyloxymethyl-polystyrene (PS-carbodiimide) or phosgene derivatives such as N,N'-carbonyldiimidazole, or 1,2-oxazolium compounds such as 2-ethyl-5-phenyl-1,2-oxazolium 3-sulfate or 2-tert-butyl-5-methylisoxazolium perchlorate, or acylamino compounds such as 2-ethoxy-1-ethoxycarbonyl-1,2-dihydroquinoline, or isobutyl chloroformate, propanephosphonic anhydride, diethyl cyanophosphonate, bis(2-oxo-3-oxazolidinyl)phosphoryl chloride, benzotriazol-1-yloxytris(dimethylamino)phosphonium hexafluorophosphate (BOP), benzotriazol-1-yloxy-tris(pyrrolidino)phosphonium hexafluorophosphate (PyBOP), O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), where appropriate in combination with further auxiliaries such as 1-hydroxybenzotriazole (HOBt) or N-hydroxysuccinimide (HOSu), and as bases alkali metal carbonates, e.g. sodium or potassium carbonate or bicarbonate, or organic amine bases such as, for example, triethylamine, N-methylmorpholine, N-methylpiperidine, N,N-diisopropylethylamine, pyridine, 4-N,N-dimethylaminopyridine, 1,5-diazabicyclo[4.3.0]non-5-ene (DBN) or 1,8-diazabicyclo[5.4.0]undec-7-ene (DBU). BOP, PyBOP or HATU, each in combination with triethylamine or N,N-diisopropylethylamine, are preferred.

Process step (XVIII)+(XIX)→(XX) is generally carried out in a temperature range from −20° C. to +100° C., preferably from 0° C. to +50° C. The reaction can be carried out under atmospheric, elevated or reduced pressure (e.g. from 0.5 to 5 bar). It is generally carried out under atmospheric pressure.

The compounds according to the invention of the formula (I) in which $R^1$ and $R^2$ are each ethoxy or n-propoxy which are substituted in position 2 or 3 by amino, mono- or di-$(C_1-C_6)$-alkylamino, $(C_3-C_8)$-cycloalkylamino, N-$(C_3-C_8)$-cycloalkyl-N-$(C_1-C_6)$-alkylamino or by a 4- to 7-membered heterocycle which is bonded via an N atom can also be prepared by reacting compounds of the formula (XXI)

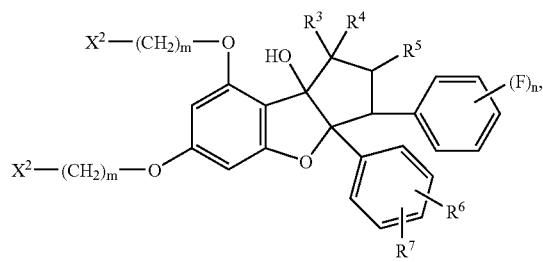

in which $R^3$, $R^4$, $R^5$, $R^6$, $R^7$ and n each have the meaning indicated above, $X^2$ is a suitable leaving group such as, for example, halogen, mesylate or tosylate and m is the number 2 or 3, in an inert solvent where appropriate in the presence of an auxiliary base with a compound of the formula (XXII)

HNR$^{15}$R$^{16}$ (XXII), in which $R^{15}$ is hydrogen, $(C_1-C_6)$-alkyl or $(C_3-C_8)$-cycloalkyl and $R^{16}$ is hydrogen or $(C_1-C_6)$-alkyl, or $R^{15}$ and $R^{16}$ together with the nitrogen atom to which they are bonded form a 4 to 7-membered heterocycle, to give compounds of the formula (XXIII)

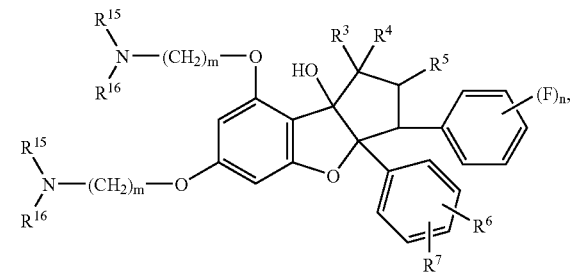

in which $R^3$, $R^4$, $R^5$, $R^6$, $R^7$, $R^{15}$, $R^{16}$, m and n each have the meaning indicated above, and then further modifying the latter where appropriate by the reaction sequences described in WO 00/08007.

The compounds of the formula (XXI) can be obtained by the processes described above or in WO 00/08007. The compounds of the formula (XXII) are commercially available or disclosed in the literature.

Inert solvents for process step (XXI)+(XXII)→(XXIII) are for example ethers such as tetrahydrofuran, dioxane, glycol dimethyl ether or diethylene glycol dimethyl ether, alcohols such as methanol, ethanol, n-propanol, isopropanol, n-butanol or tert-butanol, hydrocarbons such as toluene or xylene, or other solvents such as acetone, dimethylformamide or dimethyl sulfoxide. It is likewise possible to employ mixtures of the solvents mentioned. Ethanol, dimethylformamide, dimethyl sulfoxide or xylene are preferred.

Auxiliary bases suitable for process step (XXI)+(XXII)→(XXIII) are the usual inorganic or organic bases. These preferably include alkali metal hydroxides such as, for example, sodium or potassium hydroxide, alkali metal or alkaline earth metal carbonates such as sodium or potassium carbonate, alkali metal hydrides such as sodium hydride, or organic amines such as triethylamine or ethyldiisopropylamine.

Process step (XXI)+(XXII)→(XXIII) is generally carried out in a temperature range from +20° C. to +200° C., preferably from +70° C. to +150° C. The reaction can be carried out under atmospheric, elevated or reduced pressure (e.g. from 0.5 to 5 bar). It is generally carried out under atmospheric pressure.

The compounds according to the invention can, if expedient, also be prepared by synthetic transformations of functional groups of individual substituents in compounds of the formula (I) which are obtained by the processes described above. Such transformations of functional groups are carried out by methods usual in the literature and include for example processes for alkylation, acylation, amination, esterification, ester cleavage, hydrogenation, oxidation and reduction.

Preparation of the compounds according to the invention can be illustrated by the following synthesis schemes:

Scheme 1

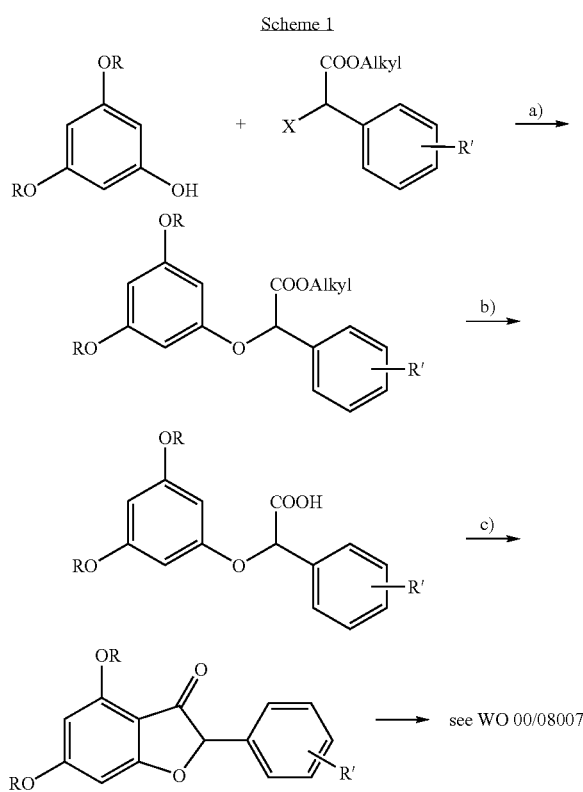

[X = halogen; a): potassium carbonate, 2-butanone, 80° C.; b): potassium carbonate, methanol/water, 65° C., c): phosphoryl chloride, zinc chloride, 0° C. → RT].

Scheme 2

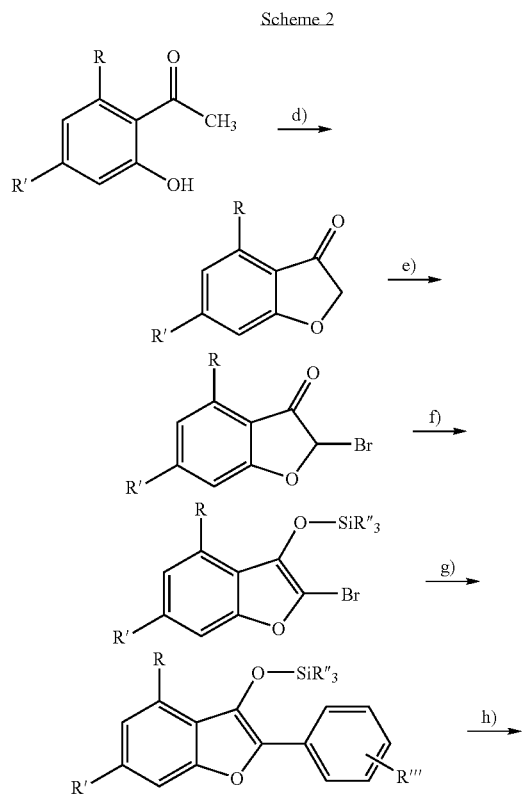

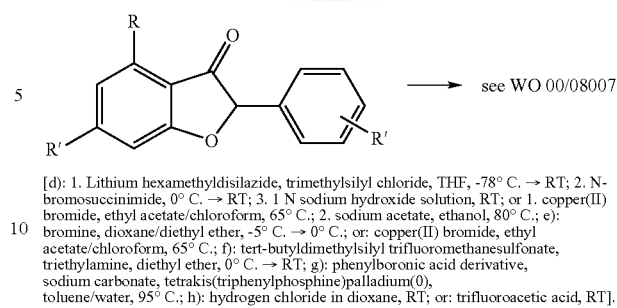

[d]: 1. Lithium hexamethyldisilazide, trimethylsilyl chloride, THF, -78° C. → RT; 2. N-bromosuccinimide, 0° C. → RT; 3. 1 N sodium hydroxide solution, RT; or 1. copper(II) bromide, ethyl acetate/chloroform, 65° C.; 2. sodium acetate, ethanol, 80° C.; e): bromine, dioxane/diethyl ether, -5° C. → 0° C.; or: copper(II) bromide, ethyl acetate/chloroform, 65° C.; f): tert-butyldimethylsilyl trifluoromethanesulfonate, triethylamine, diethyl ether, 0° C. → RT; g): phenylboronic acid derivative, sodium carbonate, tetrakis(triphenylphosphine)palladium(0), toluene/water, 95° C.; h): hydrogen chloride in dioxane, RT; or: trifluoroacetic acid, RT].

Scheme 3

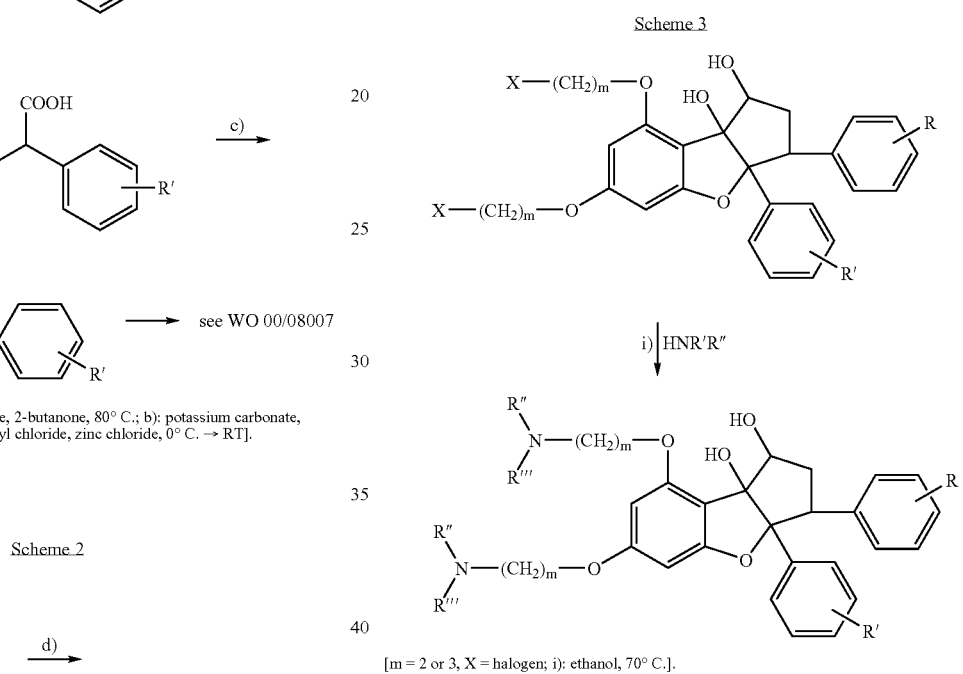

[m = 2 or 3, X = halogen; i): ethanol, 70° C.].

Scheme 4

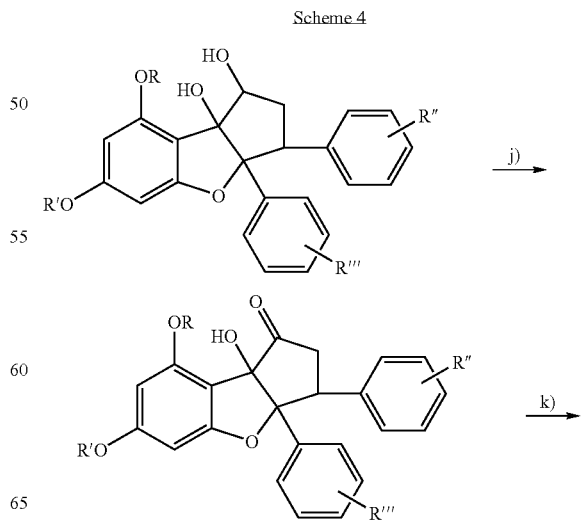

-continued

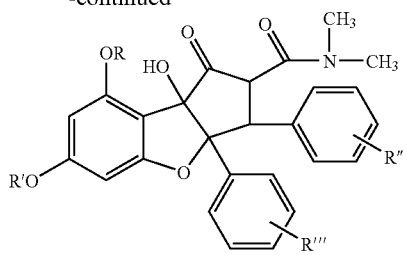

[j]: methoxymagnesium methyl carbonate, DMF, 100° C.; k):
benzotriazol-1-yloxytripyrrolidino-phosphonium hexafluorophosphate (PyBOP),
diisopropylethylamine, dimethylamine hydrochloride, THF, 0° C.].

The compounds according to the invention have valuable pharmacological properties and can be used for the prevention and treatment of disorders in humans and animals. They are moreover distinguished by an increased metabolic stability compared with the compounds described in WO 00/08007.

The compounds according to the invention are potent inhibitors/modulators of NF-κB and/or AP-1 activity and are suitable as such in particular for the treatment of chronic inflammatory and autoimmune diseases (such as, for example, Crohn's disease, ulcerative colitis, rheumatoid arthritis, psoriasis, multiple sclerosis, lupus, asthma, diabetes), cardiovascular disorders (such as, for example, coronary heart disease, myocardial infarction, atherosclerosis, restenosis, thromboses), fibrotic disorders of the liver and other organs, cerebrovascular disorders (such as, for example, stroke, craniocerebral trauma, spinal cord injuries) and chronic neurodegenerative disorders (such as, for example, Alzheimer's disease, Parkinson's disease, Huntington's chorea, amyotrophic lateral sclerosis, peripheral neuropathies and chronic pain). They can additionally be used for the prophylaxis and/or therapy of radiation damage, transplant rejection, sepsis and septic shock, and of bacterial meningitis.

The compounds according to the invention are further suitable, because of their inhibitory/modulatory activity on NF-κB and/or AP-1-mediated signal transduction for the treatment of hyperproliferative disorders such as solid tumors (such as, for example, breast cancer, lung cancer, tumors of the brain and of the nervous system, skin cancer, liver cancer, tumors of the reproductive organs, tumors of the digestive tract, bladder cancer, tumors of the urinary tract systems, tumors of various endocrine glands, tumors of the eye), lymphomas (such as, for example, Hodgkin's disease, lymphomas of the central nervous system), sarcomas (such as, for example, osteosarcomas, lymphosarcomas) and leukemias (such as, for example, acute myeloid leukemia, lymphoblastic leukemias, myelogenous leukemias). The compounds according to the invention can further be used for the prophylaxis and/or therapy of viral disorders, in particular disorders caused by HIV, HTLV, Epstein-Barr virus, cytomegalovirus (CMV) and/or adenoviruses.

The present invention further relates to the use of the compounds according to the invention for the treatment and/or prevention of disorders, especially of the aforementioned disorders.

The present invention further relates to the use of the compounds according to the invention for producing a medicament for the treatment and/or prevention of disorders, especially of the aforementioned disorders.

The present invention further relates to a method for the treatment and/or prevention of disorders, especially of the aforementioned disorders, by using an effective amount of at least one of the compounds according to the invention.

The compounds according to the invention can be employed alone or, if required, in combination with other active ingredients. The present invention further relates to medicaments comprising at least one compound according to the invention and one or more further active ingredients, in particular for the treatment and/or prevention of the aforementioned disorders. Examples of suitable combination active ingredients which may be preferably mentioned are substances having cytostatic or cytotoxic activity, antiinflammatory substances (e.g. corticosteroids, NSAIDs) and substances having neuroprotective activity.

The compounds according to the invention can act systemically and/or locally. For this purpose, they can be administered in a suitable way such as, for example, by the oral, parenteral, pulmonal, nasal, sublingual, lingual, buccal, rectal, dermal, transdermal, conjunctival, otic route or as implant or stent.

The compounds according to the invention can be administered in administration forms suitable for these administration routes.

Suitable for oral administration are administration forms which function according to the prior art and deliver the compounds according to the invention rapidly and/or in modified fashion, and which contain the compounds according to the invention in crystalline and/or amorphized and/or dissolved form, such as, for example, tablets (uncoated or coated tablets, for example having enteric coatings or coatings which are insoluble or dissolve with a delay and control the release of the compound according to the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilizates or sterile powders.

Suitable for the other administration routes are, for example, pharmaceutical forms for inhalation (inter alia powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Oral or parenteral administration is preferred, especially oral administration.

The compounds according to the invention can be converted into the stated administration forms. This can take place in a manner known per se by mixing with inert, nontoxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colors (e.g. inorganic pigments such as, for example, iron oxides) and masking flavors and/or odors.

The present invention further relates to medicaments comprising at least one compound according to the invention, usually together with one or more inert, non-toxic, pharmaceutically suitable excipients, and to the use thereof for the aforementioned purposes.

It has generally proved advantageous to administer on parenteral administration amounts of about 0.001 to 1 mg/kg, preferably about 0.01 to 0.5 mg/kg, of body weight to achieve effective results, and on oral administration the dosage is about 0.01 to 100 mg/kg, preferably about 0.01 to 20 mg/kg, and very particularly preferably 0.1 to 10 mg/kg, of body weight.

It may nevertheless be necessary where appropriate to deviate from the stated amounts, in particular as a function of the body weight, route of administration, individual response to the active ingredient, nature of the preparation and time or interval over which administration takes place. Thus, it may be sufficient in some cases to make do with less than the aforementioned minimum amount, whereas in other cases the stated upper limit must be exceeded. It may in the event of administration of larger amounts be advisable to divide these into a plurality of individual doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data for the liquid/liquid solutions are in each case based on volume.

A. EXAMPLES

| Abbreviations: | |
|---|---|
| b.p. | Boiling point |
| DCI | Direct chemical ionization (in MS) |
| DMF | N,N-Dimethylformamide |
| DMSO | Dimethyl sulfoxide |
| ESI | Electrospray ionization (in MS) |
| H | Hour(s) |
| HPLC | High pressure/high performance liquid chromatography |
| LC-MS | Coupled liquid chromatography-mass spectroscopy |
| min. | Minute(s) |
| MS | Mass spectroscopy |
| NMR | Nuclear magnetic resonance spectroscopy |
| RF | Reflux |
| RT | Room temperature (20° C.) |
| $R_t$ | Retention time (in HPLC) |
| TEA | Triethylamine |
| tert. | Tertiary |
| THF | Tetrahydrofuran |
| UV | Ultraviolet |
| v/v | Volume to volume (in liquid/liquid mixtures) |

HPLC and LC/MS Methods:
Method 1:
Instrument: Micromass Platform LCZ with HPLC Agilent Series 1100; Column: Grom-Sil 120 ODS-4 HE, 50 mm×2.0 mm, 3 µm; eluent A: 1 l of water+1 ml of 50% formic acid, eluent B: 1 l of acetonitrile+1 ml of 50% formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 208-400 nm.
Method 2:
Instrument: Micromass Quattro LCZ with HPLC Agilent Series 1100; Column: Grom-Sil 120 ODS-4 HE, 50 mm×2.0 mm, 3 µm; eluent A: 1 l of water+1 ml of 50% formic acid, eluent B: 1 l of acetonitrile+1 ml of 50% formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 208-400 nm.
Method 3:
MS instrument type: Micromass ZQ; HPLC instrument type: Waters Alliance 2790; column: Grom-Sil 120 ODS-4 HE, 50 mm×2 mm, 3.0 µm; eluent B: acetonitrile+0.05% formic acid, eluent A: water+0.05% formic acid; gradient: 0.0 min 5% B→2.0 min 40% B→4.5 min 90% B→5.5 min 90% B; oven: 45° C.; flow rate: 0.0 min 0.75 ml/min→4.5 min 0.75 ml/min→5.5 min 1.25 ml/min; UV detection: 210 nm.
Method 4:
MS instrument type: Micromass ZQ; HPLC instrument type: TSP P4000, TSP AS300, TSP UV3000; column: Grom-Sil 120 ODS-4 HE, 50 mm×2 mm, 3.0 µm; eluent A: water+250 µl of 50% formic acid/l, eluent B: acetonitrile+250 µl of 50% formic acid/l; gradient: 0.0 min 0% B→0.2 min 0% B→2.9 min 70% B→3.1 min 90% B→4.5 min 90% B; oven: 50° C.; flow rate: 0.8 ml/min; UV detection: 210 nm.
Method 5:
MS instrument type: Micromass ZQ; HPLC instrument type: Waters Alliance 2790; column: Grom-Sil 120 ODS-4 HE, 50 mm×2 mm, 3.0 µm; eluent B: acetonitrile+500 µl of 50% formic acid/l; eluent A: water+500 µl of 50% formic acid/l; gradient: 0.0 min 0% B→0.2 min 0% B→2.9 min 70% B→3.1 min 90% B→4.5 min 90% B; oven: 50° C.; flow rate: 0.8 ml/min; UV detection: 210 nm.
Method 6:
MS instrument type: Micromass ZQ; HPLC instrument type: Waters Alliance 2795; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A, flow rate 1 ml/min→2.5 min 30% A, flow rate 2 ml/min→3.0 min 5% A, flow rate 2 ml/min→4.5 min 5% A, flow rate 2 ml/min; oven: 50° C.; UV detection: 210 nm.
Method 7:
Instrument: Micromass Platform LCZ with HPLC Agilent Series 1100; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A, flow rate 1 ml/min→2.5 min 30% A, flow rate 2 ml/min→3.0 min 5% A, flow rate 2 ml/min→4.5 min 5% A, flow rate 2 ml/min; oven: 50° C.; UV detection: 210 nm.
Method 8:
Instrument: Micromass Platform LCZ with HPLC Agilent Series 1100; column: Grom-Sil 120 ODS-4 HE, 50 mm×2.0 mm, 3 µm; eluent A: 1 l of water+1 ml of 50% formic acid, eluent B: 1 l of acetonitrile+1 ml of 50% formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 210 nm.
Method 9:
MS instrument type: Micromass ZQ; HPLC instrument type: Waters Alliance 2795; column: Merck Chromolith SpeedROD RP-18e 50 mm×4.6 mm; eluent A: water+500 µl of 50% formic acid/l; eluent B: acetonitrile+500 µl of 50% formic acid/l; gradient: 0.0 min 10% B→3.0 min 95% B→4.0 min 95% B; oven: 35° C.; flow rate: 0.0 min 1.0 ml/min→3.0 min 3.0 ml/min→4.0 min 3.0 ml/min; UV detection: 210 nm.
Method 10:
MS instrument type: Micromass TOF (LCT); HPLC instrument type: 2-column switching, Waters 2690; column: YMC-ODS-AQ, 50 mm×4.6 mm, 3.0 µm; eluent A: water+0.1% formic acid, eluent B: acetonitrile+0.1% formic acid; gradient: 0.0 min 100% A→0.2 min 95% A→1.8 min 25%

A→1.9 min 10% A→3.2 min 10% A; oven: 40° C.; flow rate: 3.0 ml/min; UV detection: 210 nm.

Method 11:

Instrument: Micromass Quattro LCZ with HPLC Agilent Series 1100; column: Uptisphere HDO, 50 mm×2.0 mm, 3 µm; eluent A: 1 l of water+1 ml of 50% formic acid, eluent B: 1 l of acetonitrile+1 ml of 50% formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 208-400 nm.

Method 12:

MS instrument type: Micromass ZQ; HPLC instrument type: Waters Alliance 2790; column: Uptisphere C 18, 50 mm×2.0 mm, 3.0 µm; eluent B: acetonitrile+0.05% formic acid, eluent A: water+0.05% formic acid; gradient: 0.0 min 5% B→2.0 min 40% B→4.5 min 90% B→5.5 min 90% B; oven: 45° C.; flow rate: 0.0 min 0.75 ml/min→4.5 min 0.75 ml/min→5.5 min 1.25 ml/min; UV detection: 210 nm.

Method 13:

MS instrument type: Micromass ZQ; HPLC instrument type: HP 1100 Series; UV DAD; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 14:

MS instrument type: Micromass ZQ; HPLC instrument type: Waters Alliance 2795; column: Merck Chromolith SpeedROD RP-18e 50 mm×4.6 mm; eluent A: water+500 µl of 50% formic acid/l, eluent B: acetonitrile+500 µl of 50% formic acid/l; gradient: 0.0 min 10% B→2.0 min 95% B→4.0 min 95% B; oven: 35° C.; flow rate: 0.0 min 1.0 ml/min→2.0 min 3.0 ml/min→4.0 min 3.0 ml/min; UV detection: 210 nm.

Chiral HPLC Methods:

Method 15A (Preparative):

Column: Chiral silica gel selector Daicel Chiralpak AD; 10 µm, 250×20 mm; eluent: i-hexane/ethanol+0.2% diethylamine 40:60 (v/v); flow rate: 20 ml/min; UV detection: 220 nm; temperature: 30° C.; sample loading in i-hexane/ethanol 1:1.

Method 15B (Analytical):

Column: Chiral silica gel selector Daicel Chiralpak AD; 10 µm, 250×4.6 mm; eluent: i-hexane/ethanol+0.2% diethylamine 40:60 (v/v); flow rate: 0.7 ml/min; UV detection: 220 nm; temperature: 30° C.; sample loading in eluent.

Method 16A (Preparative):

Column: Chiral silica gel selector Daicel Chiralpak AD-H; 5 µm, 250×20 mm; eluent: acetonitrile/methanol+0.2% diethylamine 90:10 (v/v); flow rate: 20 ml/min; UV detection: 220 nm; temperature: 25° C.; sample loading in acetonitrile/methanol 54:46 (v/v).

Method 16B (Analytical):

Column: Daicel Chiralpak AD-H; 5 µm, 250×20 mm; eluent: acetonitrile/methanol+0.2% diethylamine 90:10 (v/v); flow rate: 1.0 ml/min; UV detection: 220 nm; temperature: 25° C.; sample loading in eluent.

Method 17A (Preparative):

Column: Chiral silica gel selector Daicel Chiralpak AD-H; 5 µm, 250×20 mm; eluent: acetonitrile/methanol+0.2% diethylamine 85:15 (v/v); flow rate: 20 ml/min; UV detection: 230 nm; temperature: 25° C.; sample loading in acetonitrile.

Method 17B (Analytical):

Column: Chiral silica gel selector Daicel Chiralpak AD-H; 5 µm, 250×4.6 mm; eluent: methanol/acetonitrile+0.5% diethylamine 20:80 (v/v); flow rate 0.5 ml/min; UV detection: 230 nm; temperature: 25° C.; sample loading in eluent.

Method 18A (Preparative):

Column: Chiral silica gel selector Daicel Chiralpak AD-H; 5 µm, 250×20 mm; eluent: acetonitrile/methanol+0.2% diethylamine 60:40 (v/v); flow rate: 20 ml/min; UV detection: 230 nm; temperature: 25° C.; sample loading in acetonitrile/methanol 58:42 (v/v).

Method 18B (Analytical):

Column: Chiral silica gel selector Daicel Chiralpak AD-H; 5 µm, 250×4.6 mm; eluent: methanol/acetonitrile+0.5% diethylamine 20:80 (v/v); flow rate: 1.0 ml/min; UV detection: 230 nm; temperature: 30° C.; sample loading in eluent.

Method 19A (Preparative):

Column: Chiral silica gel selector Daicel Chiralpak AD; 10 µm, 250×10 mm; eluent: ethanol+0.2% diethylamine; flow rate: 10 ml/min; UV detection: 220 nm; temperature: 40° C.; sample loading in ethanol.

Method 19B (Analytical):

Column: Chiral silica gel selector Daicel Chiralpak AD; 10 µm, 250×4.6 mm; eluent: ethanol+0.2% diethylamine; flow rate: 0.7 ml/min; UV detection: 220 nm; temperature: 25° C.; sample loading in eluent.

Method 20A (Preparative):

Column: Chiral silica gel selector KBD 5326A based on the selector poly(N-methacryloyl-L-leucine dicyclopropylamide); 10 µm, 250×20 mm; eluent: isohexane/methyl tert-butyl ether 1:1 (v/v); flow rate: 25 ml/min; UV detection: 254 nm; temperature: 24° C.; sample loading in isohexane/methyl tert-butyl ether 1:1.

Method 20B (Analytical):

Column: Chiral silica gel selector KBD 5326A; 10 µm, 250×4.6 mm; eluent: isohexane/methyl tert-butyl ether 2:3 (v/v); flow rate: 1 ml/min; UV detection: 254 nm; temperature: 25° C.; sample loading in eluent.

Method 21A (Preparative):

Column: Chiral silica gel selector KBD 5326A based on the selector poly(N-methacryloyl-L-leucine dicyclopropylamide); 10 µm, 250×20 mm; eluent: isohexane/methyl tert-butyl ether 2:3 (v/v); flow rate: 25 ml/min; UV detection: 254 nm; temperature: 24° C.; sample loading in isohexane/methyl tert-butyl ether 1:1.

Method 21B (Analytical):

Column: Chiral silica gel selector KBD 5326A; 10 µm, 250×4.6 mm; eluent: isohexane/methyl tert-butyl ether 2:3 (v/v); flow rate: 1 ml/min; UV detection: 254 nm; temperature: 25° C.; sample loading in eluent.

Method 22A (Preparative):

Column: Chiral silica gel selector KBD 8361, based on the selector poly(N-methacryloyl-L-leucine 1-menthylamide); 10 µm, 250×20 mm; eluent:isohexane/methyl tert-butyl ether 3:2 (v/v); flow rate: 25 ml/min; UV detection: 254 nm; temperature: 24° C.; sample loading in isohexane/methyl tert-butyl ether 3:2.

Method 22B (Analytical):

Column: Chiral silica gel selector KBD 5326A; 10 µm, 250×4.6 mm; eluent: isohexane/methyl tert-butyl ether 2:3 (v/v); flow rate: 1 ml/min; UV detection: 254 nm; temperature: 25° C.; sample loading in eluent.

Method 23A (Preparative):

Column: Kromasil 100 C18; 5 µm, 250×20 mm; flow rate: 25 ml/min; running time: 20 min; eluent A: water+0.2% trifluoroacetic acid, eluent B: acetonitrile; gradient: 5% B (0 min)→95% B (15 min)→5% B (15.1 min)→5% B (20 min); UV detection: 210 nm; temperature: 40° C.; sample loading in acetonitrile/water 2:1 (v/v).

Method 23B (Analytical):
Column: Kromasil 100 C18; 5 μm, 250×4 mm; flow rate: 1.0 ml/min; running time: 20 min; eluent A: water+0.2% trifluoroacetic acid, eluent B: acetonitrile; gradient: 5% B (0 min)→95% B (10 min)→95% B (15.0 min)→5% B (15.1 min)→5% B (20 min); UV detection: 210 nm; temperature: 40° C.; sample loading in acetonitrile/water 2:1 (v/v).

Method 24A (Preparative):
Column: Chiral silica gel selector Daicel Chiralpak AD; 10 μm, 250×20 mm; eluent: i-hexane/ethanol+0.2% diethylamine 90:10 (v/v); flow rate: 25 ml/min; UV detection: 220 nm; temperature: 25° C.; sample loading in i-hexane/ethanol 5:1 (v/v).

Method 25A (Preparative):
Column: Chiral silica gel selector Daicel Chiralpak AD; 20 μm, 500×40 mm; eluent: isopropanol/methanol+0.1% diethylamine 85:15 (v/v); flow rate: 100 ml/min; UV detection: 220 nm; temperature: 30° C.; sample loading in isopropanol.

Method 25B (Analytical):
Column: Chiral silica gel selector Daicel Chiralpak AD; 10 μm, 250×4.6 mm; eluent: isopropanol/methanol+0.1% diethylamine 85:15 (v/v); flow rate: 1.0 ml/min; UV detection: 250 nm; temperature: 25° C.; sample loading in eluent.

Method 26A (Preparative):
Column: Chiral silica gel selector Daicel Chiralpak AD; 20 μm, 350×30 mm; eluent: isopropanol/methanol+0.1% diethylamine 75:25 (v/v); flow rate: 50 ml/min; UV detection: 220 nm; temperature: 25° C.; sample loading in isopropanol/methanol 75:25 (v/v).

Method 26B (Analytical):
Column: Chiral silica gel selector Daicel Chiralpak AD; 10 μm, 250×4.6 mm; eluent: isopropanol/methanol+0.2% diethylamine 85:15 (v/v); flow rate: 1.0 ml/min; UV detection: 250 nm; temperature: 25° C.; sample loading in eluent.

Method 27A (Preparative):
Column: Chiral silica gel selector Daicel Chiralpak AD; 20 μm, 500×40 mm; eluent: isopropanol/methanol+0.1% diethylamine 75:25 (v/v); flow rate: 50 ml/min; UV detection: 220 nm; temperature: 25° C.; sample loading in isopropanol/methanol 75:25 (v/v).

Method 27B (Analytical):
Column: Chiral silica gel selector Daicel Chiralpak AD; 10 μm, 250×4.6 mm; eluent: isopropanol/methanol+0.2% diethylamine 85:15 (v/v); flow rate: 1.0 ml/min; UV detection: 250 nm; temperature: 25° C.; sample loading in eluent.

Method 28A (Preparative):
Column: Chiral silica gel selector Daicel Chiralpak AD; 20 μm, 500×40 mm; eluent: isopropanol/methanol+0.1% diethylamine 85:15 (v/v); flow rate: 50 ml/min; UV detection: 220 nm; temperature: 25° C.; sample loading in isopropanol/methanol 85:15 (v/v).

Method 28B (Analytical):
Column: Chiral silica gel selector Daicel Chiralpak AD; 10 μm, 250×4.6 mm; eluent: isopropanol/methanol+0.1% diethylamine 5:1 (v/v); flow rate: 1 ml/min; UV detection: 250 nm; temperature: 25° C.; sample loading in eluent.

Method 29A (Preparative):
Column: Chiral silica gel selector Daicel Chiralpak AD; 10 μm, 250×20 mm; eluent: i-hexane/ethanol+0.2% diethylamine 85:15 (v/v); flow rate: 25 ml/min; UV detection: 220 nm; temperature: 25° C.; sample loading in ethanol.

Method 29B (Analytical):
Column: Chiral silica gel selector Daicel Chiralpak AD; 10 μm, 250×4.6 mm; eluent: isopropanol/methanol+0.1% diethylarnine 5:1 (v/v); flow rate: 1 ml/min; UV detection: 250 nm; temperature: 25° C.; sample loading in eluent.

Method 30A (Preparative):
Column: Chiral silica gel selector ZWE 803AB, based on the selector poly(N-methacryloyl-L-phenylalanine d-neomenthylamide); 10 μm, 250×20 mm; eluent: isohexane/methyl tert-butyl ether 1:4 (v/v); flow rate: 25 ml/min; UV detection: 254 nm; temperature: 24° C.; sample loading in methyl tert-butyl ether.

Method 30B (Analytical):
Column: Chiral silica gel selector ZWE 803AB; 10 μm, 250×4.6 mm; eluent: methyl tert-butyl ether; flow rate: 1 ml/min; UV detection: 254 nm; temperature: 25° C.; sample loading in eluent.

Starting Compounds and Intermediates:

Example 1A 3,5-Diethoxyphenol

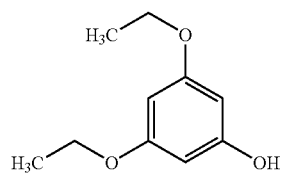

Hydrogen chloride gas is passed into a solution of 188 g (1.49 mol) of phloroglucinol in 600 ml of ethanol under RF for 5 h. Cooling is followed by stirring at RT overnight. Hydrogen chloride gas is then again passed in under RF for 5 h. After cooling, the reaction mixture is concentrated and the residue is taken up in dichloromethane and water. The organic phase is separated off, the aqueous phase is extracted twice with dichloromethane, and the combined organic phases are dried over sodium sulfate, filtered and concentrated. The residue is distilled in vacuo (b.p.: 145-150° C./0.5 mbar). The distillate is dissolved in dichloromethane, and the solution is extracted five times with 5% strength aqueous potassium carbonate solution to remove 5-ethoxyresorcinol, and the organic phase is dried over sodium sulfate, filtered and concentrated. 156 g (57% of theory) of the product are obtained.

LC-MS (Method 1): $R_t$=3.32 min.

MS (ESIpos): m/z=183 (M+H)$^+$ $^1$H-NMR (400 MHz, DMSO-d$_6$): δ=9.35 (s, 1 H), 5.90 (s, 3 H), 3.91 (q, 4 H), 1.27 (t, 6 H).

Example 2A

Methyl(4-bromophenyl)-(3,5-diethoxyphenoxy)acetate

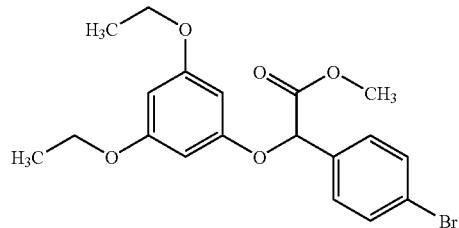

20.0 g (110 mmol) of 3,5-diethoxyphenol and 30.7 g (99.8 mmol) of methyl bromo(4-bromophenyl)acetate are dissolved in 39 ml of 2-butanone under argon at RT, and 31.0 g (225 mmol) of potassium carbonate are added. The reaction mixture is heated under RF for 4 h. After cooling, the precipitate is filtered off with suction and washed with 2-butanone, and the filtrate is concentrated. Chromatography on silica gel 60 (mobile phase: toluene) results in 33.1 g (81% of theory) of the product.

LC-MS (Method 2): $R_t$=4.64 min.
MS (ESIpos): m/z=409 (M+H)$^+$
$^1$H-NMR (400 MHz, DMSO-d$_6$): δ=7.66-7.60 (m, 2 H), 7.53-7.46 (m, 2 H), 6.11 (d, 2 H), 6.09 (t, 1 H), 6.05 (s, 1 H), 3.95 (q, 4 H), 3.66 (s, 3 H), 1.28 (t, 6 H).

Example 3A (4-Bromophenyl)-(3,5-diethoxyphenoxy)acetic acid

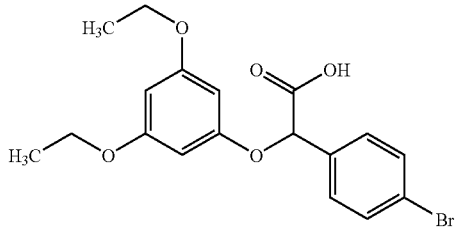

16.9 g (41.3 mmol) of methyl(4-bromophenyl)-(3,5-diethoxyphenoxy)acetate are dissolved in 80 ml of methanol and 8 ml of water under argon at RT, and 7.99 g (57.8 mmol) of potassium carbonate are added. The mixture is heated under RF for 4 h. After cooling, the precipitate is filtered off, the filtrate is concentrated, the residue is taken up in water and the solution is extracted four times with diethyl ether. The aqueous phase is adjusted to a pH of 2 by adding 10% strength hydrochloric acid and is extracted three times with ethyl acetate, and the combined ethyl acetate phases are washed with saturated sodium chloride solution, dried over sodium sulfate, filtered and concentrated. 16.1 g (99% of theory) of the product are obtained.

LC-MS (Method 4): $R_t$=3.85 min.
MS (ESIpos): m/z=395 (M+H)$^+$
$^1$H-NMR (400 MHz, DMSO-d$_6$): δ=13.37 (s, 1 H), 7.66-7.58 (m, 2 H), 7.53-7.45 (m, 2 H), 6.11-6.06 (m, 3 H), 5.83 (s, 1 H), 3.95 (q, 4 H), 1.28 (t, 6 H).

Example 4A 2-(4-Bromophenyl)-4,6-diethoxybenzofuran-3(2H)-one

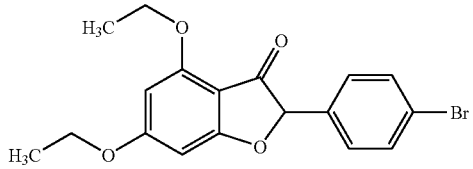

38 ml (407 mmol) of phosphoryl chloride are added to 16.1 g (40.7 mmol) of (4-bromophenyl)-(3,5-diethoxyphenoxy)acetic acid under argon at RT. The mixture is cooled to 0° C., and 8.32 g (61.0 mmol) of zinc chloride are added. After 10 min, the ice bath is removed and the mixture is stirred at RT overnight. The reaction mixture is poured into a large amount of ice-water and stirred for 15 min. Dichloromethane is added, the phases are separated, and the organic phase is washed with water, dried over sodium sulfate, filtered and concentrated. Gradient chromatography on silica gel 60 (mobile phase: toluene/ethyl acetate) results in 10.2 g (67% of theory) of the product.

LC-MS (Method 4): $R_t$=4.04 min.
MS (ESIpos): m/z=377 (M+H)$^+$
$^1$H-NMR (400 MHz, DMSO-d$_6$): δ=7.64-7.58 (m, 2 H), 7.28-7.23 (m, 2 H), 6.46 (d, 1 H), 6.19 (d, 1 H), 5.72 (s, 1 H), 4.22-4.05 (m, 4 H), 1.39-1.26 (m, 6 H).

Example 5A (S*,R*)-3-[2-(4-Bromophenyl)-4,6-diethoxy-3-oxo-2,3-dihydrobenzofuran-2-yl]-3-phenylpropanal

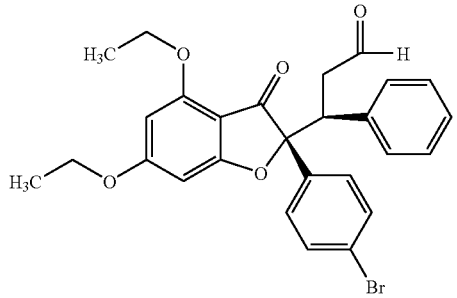

Under argon, 20.9 g (55.4 mmol) of 2-(4-bromophenyl)-4,6-diethoxybenzofuran-3-one are dissolved in 422 ml of degassed methanol and 100 ml of degassed toluene. At RT, 2.00 g (11.1 mmol) of a 30% strength methanolic sodium methoxide solution are added. One minute later, cinnamaldehyde (9.52 g, 72.0 mmol) dissolved in 111 ml of degassed toluene is added. The mixture is stirred at RT overnight and then left to stand for 48 h. Subsequently saturated ammonium chloride solution is added and the mixture is extracted three times with dichloromethane. The combined organic phases are dried over sodium sulfate, filtered and concentrated. Column chromatography on silica gel 60 (mobile phase: toluene/ethyl acetate 95:5) results in 10.7 g (38% of theory) of the title compound as racemic mixture and 6.00 g (21% of theory) of the diastereomer (R*,R*)-3-[2-(4-bromophenyl)-4,6-diethoxy-3-oxo-2,3-dihydrobenzofuran-2-yl]-3-phenylpropanal as racemic mixture.

LC-MS (Method 4): $R_t$=4.19 min.
MS (ESIpos): m/z=509 (M+H)$^+$
$^1$H-NMR (400 MHz, DMSO-d$_6$): δ=9.32 (d, 1 H), 7.69-7.62 (m, 2 H), 7.61-7.54 (m, 2 H), 7.31-7.10 (m, 5 H), 6.48 (d, 1 H), 5.97 (d, 1 H), 4.24 (dd, 1 H), 4.12 (q, 2 H), 4.01-3.81 (m, 2 H), 3.02 (ddd, 1 H), 2.57-2.44 (m, 1 H), 1.33 (t, 3 H), 1.18 (t, 3 H).

Example 6A (1S*,3S*,3aR*,8bS*)-3a-(4-Bromophenyl)-6,8-diethoxy-3-phenyl-2,3,3a,8b-tetrahydrocyclopenta-[b]benzofuran-1,8b-(1H)-diol

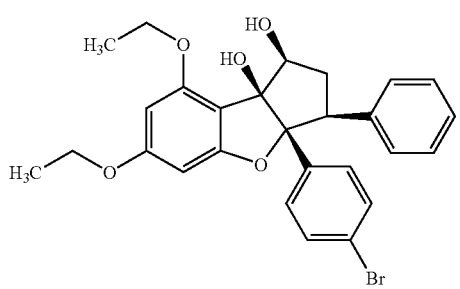

178 ml (17.9 mmol) of a 0.1 M solution of samarium diiodide in THF is cooled to 0° C. under argon, and a solution of 2.60 g (5.10 mmol) of (S*,R*)-3-[2-(4-bromophenyl)-4,6-diethoxy-3-oxo-2,3-dihydrobenzofuran-2-yl]-3-phenylpropanal in 30 ml of degassed THF is added dropwise. The mixture is stirred at 0° C. for 1 h and at RT for 1 h. An ice-cold saturated sodium potassium tartrate solution with 10% potassium carbonate is added, the phases are separated, the aqueous phase is extracted three times with dichloromethane, and the combined organic phases are washed with saturated sodium chloride solution, dried over sodium sulfate, filtered and concentrated. Column chromatography on silica gel 60 (mobile phase: toluene/ethyl acetate 95:5) results in 1.55 g (58% of theory) of the product as racemic mixture.

LC-MS (Method 3): $R_t$=4.62 min.

MS (ESIpos): m/z=511 (M+H)$^+$ $^1$H-NMR (400 MHz, DMSO-d$_6$): δ=7.35-7.28 (m, 2 H), 7.24-7.02 (m, 5 H), 6.91-6.84 (m, 2 H), 6.28 (d, 1 H), 6.14 (d, 1 H), 5.81 (d, 1 H), 4.84 (s, 1 H), 4.71 (ddd, 1 H), 4.13-3.98 (m, 4 H), 3.32-3.18 (m, 1 H), 2.58-2.41 (m, 1 H), 2.15 (dt, 1 H), 1.35 (t, 3 H), 1.33 (t, 3 H).

Example 7A (3S*,3aR*,8bR*)-3a-(4-Bromophenyl)-6,8-ethoxy-8b-hydroxy-3-phenyl-2,3,3a,8b-tetrahydrocyclopenta[b]benzofuran-1-one

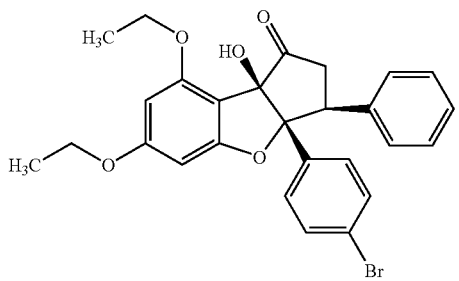

2.60 g (5.08 mmol) of (1S*,3S*,3aR*,8bS*)-3a-(4-bromophenyl)-6,8-diethoxy-3-phenyl-2,3,3a,8b-tetrahydrocyclopenta[b]benzofuran-1,8b-(1H)-diol are dissolved in 19 ml of DMSO under argon and cooled to 0° C. 7.80 ml (55.9 mmol) of TEA and a solution of 2.43 g (15.3 mmol) of sulfur trioxide-pyridine complex in 9.60 ml of DMSO are added dropwise, and the mixture is allowed to warm to RT and is stirred overnight. It is then mixed with ice-cold saturated ammonium chloride solution and stirred for 30 min. The precipitate is filtered off with suction and washed with a little water. Gradient chromatography on silica gel 60 (mobile phase: toluene/ethyl acetate) results in 2.00 g (77% of theory) of the product as racemic mixture.

LC-MS (Method 5): $R_t$=4.02 min.

MS (ESIpos): m/z=509 (M+H)$^+$ $^1$H-NMR (400 MHz, DMSO-d$_6$): δ=7.39-6.90 (m, 9 H), 6.43 (d, 1 H), 6.17 (d, 1 H), 5.82 (s, 1 H), 4.20-3.93 (m, 4 H), 3.70 (dd, 1 H), 3.12 (dd, 1 H), 2.93 (dd, 1 H), 1.34 (t, 3 H), 1.30 (t, 3 H).

Example 8A (1R*,3S*,3aR*,8bS*)-3a-(4-Bromophenyl)-6,8-diethoxy-3-phenyl-2,3,3a,8b-tetrahydrocyclopenta-[b]benzofuran-1,8b-(1H)-diol

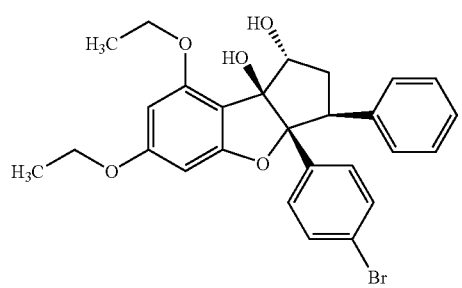

1.2 ml of glacial acetic acid are added to 814 mg (3.09 mmol) of tetramethylammonium triacetoxyborohydride in 1.2 ml of acetonitrile under argon, and the mixture is stirred at RT for 0.5 h. Then 105 mg (0.21 mmol) of (3S*,3aR*,8bR*)-3a-(4-bromophenyl)-6,8-diethoxy-8b-hydroxy-3-phenyl-2,3,3a,8b-tetrahydrocyclopenta[b]benzofuran-1-one are added dropwise as solution in 12 ml of acetonitrile. The mixture is stirred at RT overnight. At 0° C., saturated sodium bicarbonate solution is added to the reaction mixture, the aqueous phase is extracted twice with dichloromethane, and the combined organic phases are dried over sodium sulfate, filtered and concentrated. Gradient chromatography on silica gel 60 (mobile phase: toluene/ethyl acetate) results in 77 mg (71% of theory) of the product as racemic mixture.

LC-MS (Method 1): $R_t$=4.20 min.

MS (ESIpos): m/z=512 (M+H)$^+$ $^1$H-NMR (200 MHz, DMSO-d$_6$): δ=7.27-7.18 (m, 2 H), 7.15-6.96 (m, 7 H), 6.24 (d, 1 H), 6.10 (d, 1 H), 4.95 (s, 1 H), 4.54-4.46 (m, 1 H), 4.42 (d, 1 H), 4.13-3.89 (m, 5 H), 2.70 (dt, 1 H), 2.01 (dd, 1 H), 1.33 (t, 3 H), 1.31 (t, 3 H).

Preparative separation of the racemate into the enantiomers is carried out by HPLC on a chiral phase by method 22A.

Analytical Data (Method 22B):

Enantiomer A: $R_t$=3.66 min., Enantiomer B: $R_t$=4.30 min.

Example 9A (2R*,3S*,3aR*,8bR*)-3a-(4-Bromophenyl)-6,8-diethoxy-8b-hydroxy-1-oxo-3-phenyl-2,3,3a,8b-tetrahydrocyclopenta[b]benzofuran-2-carboxylic acid

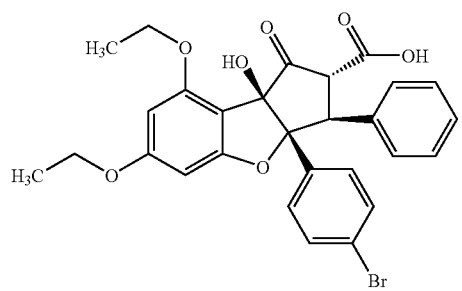

The title compound is prepared in analogy to the synthesis of Example 17A starting from Example 7A. The compound is employed directly in the next stage without further characterization.

Example 10A (4-Methylchlorophenyl)-(3,5-diethoxyphenoxy)acetate

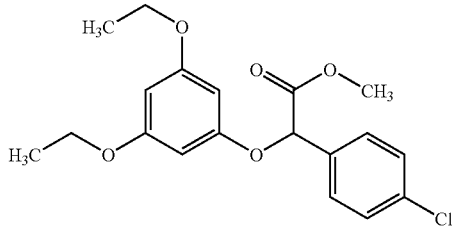

The title compound is prepared in analogy to the synthesis of Example 2A starting from methyl bromo(4-chlorophenyl)acetate.

Yield: 96% of theory.

LC-MS (Method 2): $R_t$=3.33 min.

MS (ESIpos): m/z=365 (M+H)$^+$ $^1$H-NMR (200 MHz, DMSO-d$_6$): δ=7.58-7.47 (m, 4 H), 6.12-6.08 (m, 4 H), 3.95 (q, 4 H), 3.66 (s, 3 H), 1.28 (t, 3 H).

Example 11A (4-Chlorophenyl)-(3,5-diethoxyphenoxy)acetic acid

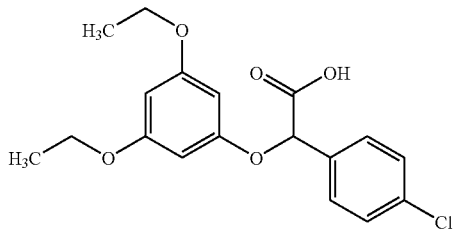

The title compound is prepared in analogy to the synthesis of Example 3A starting from Example 10A.

Yield: 91% of theory.

LC-MS (Method 1): $R_t$=3.80 min.

MS (ESIpos): m/z=351 (M+H)$^+$ $^1$H-NMR (300 MHz, DMSO-d$_6$): δ=13.26 (br. s, 1 H), 7.57 (d, 2 H), 7.48 (d, 2 H), 6.11-6.09 (m, 3 H), 5.85 (s, 1 H), 3.95 (q, 2 H), 1.28 (t, 3 H).

Example 12A 2-(4-Chlorophenyl)-4,6-diethoxybenzofuran-3(2H)-one

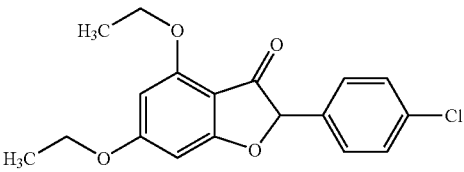

The title compound is prepared in analogy to the synthesis of Example 4A starting from Example 11A.

Yield: 85% of theory.

LC-MS (Method 1): $R_t$=4.00 min.

MS (ESIpos): m/z=333 (M+H)$^+$ $^1$H-NMR (200 MHz, DMSO-d$_6$): δ=7.48 (d, 2 H), 7.31 (d, 2 H), 6.47 (d, 1 H), 6.20 (d, 1 H), 5.75 (s, 1 H), 4.22-4.04 (m, 4 H), 1.39-1.37 (m, 6 H).

Example 13A (S*,R*)-3-[2-(4-Chlorophenyl)-4,6-diethoxy-3-oxo-2,3-dihydrobenzofuran-2-yl]-3-phenylpropanal

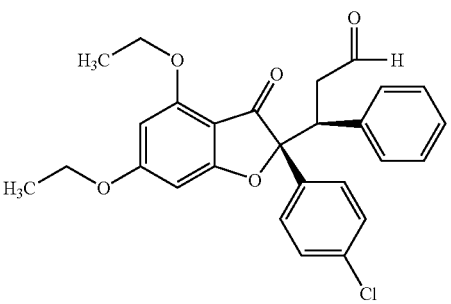

The title compound is prepared in analogy to the synthesis of Example 5A starting from Example 12A.

Yield: 35% of theory (pure diastereomer)

LC-MS (Method 4): $R_t$=4.09 min.

MS (ESIpos): m/z=465 (M+H)$^+$ $^1$H-NMR (300 MHz, DMSO-d$_6$): δ=9.32 (d, 1 H), 7.64 (d, 2 H), 7.51 (d, 2 H), 7.28-7.25 (m, 2 H), 7.19-7.08 (m, 3 H), 6.46 (d, 1 H), 5.97 (d, 1 H), 4.23 (dd, 1 H), 4.12 (q, 2 H), 3.98-3.85 (m, 2 H), 3.01 (ddd, 1 H), 2.54-2.47 (m, 1 H), 1.33 (t, 3 H), 1.17 (t, 3 H).

Example 14A (1S*,3S*,3aR*,8bS*)-3a-(4-Chlorophenyl)-6,8-diethoxy-3-phenyl-2,3,3a,8b-tetrahydrocyclopenta-[b]benzofuran-1,8b-(1H)-diol

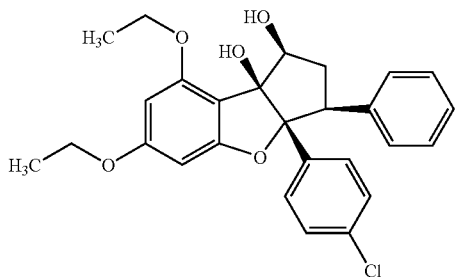

The title compound is prepared in analogy to the synthesis of Example 6A starting from Example 13A.

Yield: 55% of theory.

LC-MS (Method 3): $R_t$=3.79 min.

MS (ESIpos): m/z=467 (M+H)$^+$ $^1$H-NMR (200 MHz, DMSO-d$_6$): δ=7.26-7.05 (m, 7 H), 6.89-6.85 (m, 2 H), 6.28 (d, 1 H), 6.14 (d, 1 H), 5.81 (d, 1 H), 4.84 (s, 1 H), 4.76-4.67 (m, 1 H), 4.12-3.99 (m, 4 H), 3.31-3.19 (m, 1 H), 2.47-2.42 (m, 1 H), 2.23-2.04 (m, 1 H), 1.39-1.30 (m, 6 H).

Example 15A (3S*,3aR*,8bR*)-3a-(4-Chlorophenyl)-6,8-diethoxy-8b-hydroxy-3-phenyl-2,3,3a,8b-tetrahydrocyclopenta[b]benzofuran-1-one

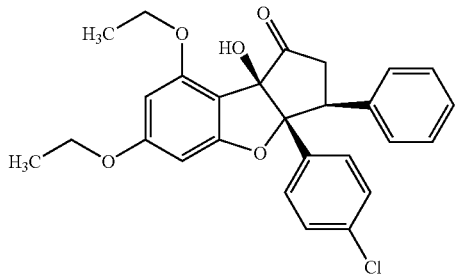

The title compound is prepared in analogy to the synthesis of example 7A starting from Example 14A.

Yield: 93% of theory.

LC-MS (Method 5): $R_t$=1.27 min.

MS (ESIpos): m/z=465 (M+H)$^+$ $^1$H-NMR (300 MHz, DMSO-d$_6$): δ=7.19-6.97 (m, 9 H), 6.43 (d, 1 H), 6.16 (d, 1 H), 5.78 (s, 1 H), 4.12-3.95 (m, 4 H), 3.71 (dd, 1 H), 3.15-2.89 (m, 2 H), 1.34 (t, 3 H), 1.30 (t, 3 H).

Example 16A (1R*,3S*,3aR*,8bS*)-3a-(4-Chlorophenyl)-6,8-diethoxy-3-phenyl-2,3,3a,8b-tetrahydrocyclopenta-[b]benzofuran-1,8b-(1H)-diol

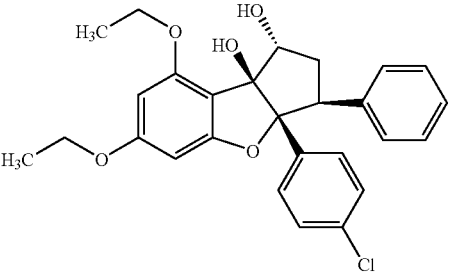

The title compound is prepared in analogy to the synthesis of Example 8A starting from Example 15A.

Yield: 83% of theory.

LC-MS (Method 2): $R_t$=4.59 min.

MS (ESIneg): m/z=465 (M−H)$^-$ $^1$H-NMR (200 MHz, DMSO-d$_6$): δ=7.20-6.96 (m, 9 H), 6.24 (d, 1 H), 6.10 (d, 1 H), 4.95 (s, 1 H), 4.54-4.47 (m, 1 H), 4.42 (d, 1 H), 4.13-3.89 (m, 5 H), 2.70 (dt, 1 H), 2.01 (dd, 1 H), 1.33 (t, 3 H), 1.31 (t, 3 H).

Preparative separation of the racemate into the enantiomers is carried out by HPLC on a chiral phase by method 21A.

Analytical Data (Method 21B):

Enantiomer A: $R_t$=4.52 min., enantiomer B: $R_t$=7.56 min.

Example 17A (2R*,3S*,3aR*,8bR*)-3a-(4-Chlorophenyl)-6,8-diethoxy-8-hydroxy-3-phenyl-2,3,3a,8b-tetrahydrocyclopenta[b]benzofuran-2-carboxylic acid

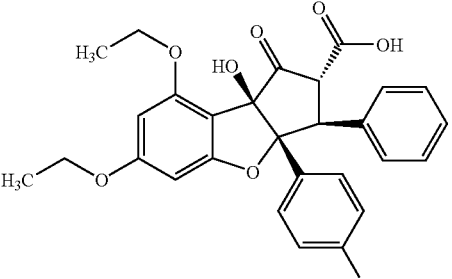

A mixture of 500 mg (1.08 mmol) of (3S*,3aR*,8bR*)-3a-(4-chlorophenyl)-6,8-diethoxy-8b-hydroxy-3-phenyl-2,3,3a,8b-tetrahydrocyclopenta[b]benzofuran-1-one (Example 15A) and 1.08 ml (2.15 mmol) of a 2 M solution of methoxymagnesium methyl carbonate in DMF is heated with stirring at 100° C. in a closed vessel for 16 h. The resulting suspension is then poured into a mixture of ice-cold 5 N hydrochloric acid and ethyl acetate. The organic phase is separated off, washed with saturated sodium chloride solution, dried over magnesium sulfate, filtered with suction and concentrated. 531 mg of crude product are employed directly in the next stage without further characterization.

Example 18A 3,5-Bis-(2-methoxyethoxy)-phenol

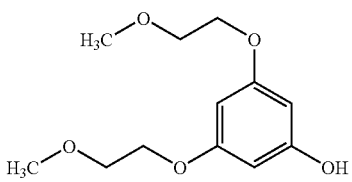

Hydrogen chloride gas is passed into a solution of 50.0 g (397 mmol) of phloroglucinol in 500 ml of ethylene glycol monomethyl ether at 80° C. over the course of 4 h. Addition of a further 300 ml of ethylene glycol monomethyl ether is followed by heating under RF while continuing to pass in hydrogen chloride gas for 2 h. The mixture is cooled and concentrated, the residue is taken up in 200 ml of DMF, 10.9 g (79.2 mmol) of potassium carbonate are added, and the mixture is heated to 50° C. Then 10.9 g (78.2 mmol) of 2-bromomethyl methyl ether are added dropwise as solution in 100 ml of DMF. The mixture is stirred at 50° C. for 2 h. It is then concentrated, the residue is taken up in a mixture of diethyl ether and water, the phases are separated and the aqueous phase is extracted twice with diethyl ether. The aqueous phase is adjusted to a pH of 5 with concentrated hydrochloric acid and extracted three times with diethyl ether. The combined organic phases are washed with saturated sodium chloride solution, dried over sodium sulfate, filtered and concentrated. Gradient chromatography on silica gel 60 (mobile phase: toluene/ethyl acetate) results in 9.20 g (10% of theory) of the product.

LC-MS (Method 9): $R_t$=1.60 min.

MS (ESIpos): m/z=243 (M+H)$^+$ $^1$H-NMR (300 MHz, DMSO-d$_6$): δ=9.35 (s, 1 H), 5.97-5.91 (m, 3 H), 4.01-3.96 (m, 4 H), 3.63-3.58 (m, 4 H), 3.29 (s, 6 H).

Example 19A

Methyl[3,5-bis-(2-methoxyethoxy)-phenoxy]-(4-bromophenyl)acetate

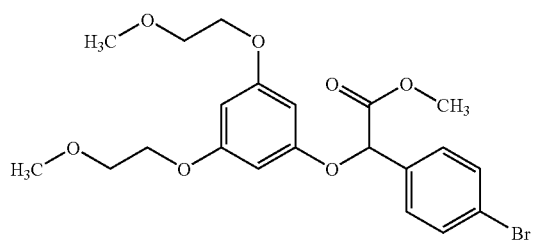

The title compound is prepared in analogy to the synthesis of Example 2A starting from Example 18A.

Yield: 73% of theory.

LC-MS (Method 3): $R_t$=4.17 min.

MS (ESIpos): m/z=470 (M+H)$^+$ $^1$H-NMR (300 MHz, DMSO-d$_6$): δ=7.66-7.60 (m, 2 H), 7.52-7.46 (m, 2 H), 6.17-6.13 (m, 3 H), 6.07 (s, 1 H), 4.05-4.00 (m, 4 H), 3.66 (s, 3 H), 3.63-3.59 (m, 4 H), 3.29 (s, 6 H).

Example 20A

[3,5-Bis-(2-methoxyethoxy)-phenoxy]-(4-bromophenyl)acetic acid

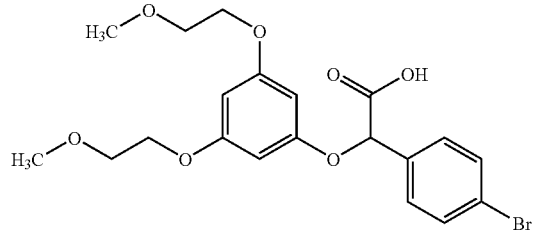

The title compound is prepared in analogy to the synthesis of Example 3A starting from Example 19A.

Yield: 86% of theory.

LC-MS (Method 3): $R_t$=3.68 min.

MS (ESIpos): m/z=456 (M+H)$^+$ $^1$H-NMR (300 MHz, DMSO-d$_6$): δ=13.3 (s, 1 H), 7.65-7.59 (m, 2 H), 7.53-7.47 (m, 2 H), 6.14 (s, 3 H), 5.86 (s, 1 H), 4.05-4.00 (m, 4 H), 3.64-3.59 (m, 4 H), 3.29 (s, 6 H).

Example 21A 4,6-Bis-(2-methoxyethoxy)-2-(4-bromophenyl)-benzofuran-3(2H)-one

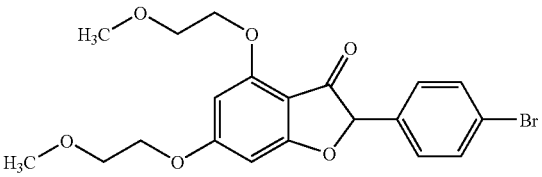

The title compound is prepared in analogy to the synthesis of Example 4A starting from Example 20A.

Yield: 19% of theory.

LC-MS (Method 2): $R_t$=4.29 min.

MS (ESIpos): m/z=438 (M+H)$^+$ $^1$H-NMR (300 MHz, DMSO-d$_6$): δ=7.64-7.58 (m, 2 H), 7.29-7.23 (m, 2 H), 6.50 (d, 1 H), 6.26 (d, 1 H), 5.74 (s, 1 H), 4.27-4.15 (m, 4 H), 3.71-3.62 (m, 4 H), 3.32 (s, 3 H), 3.31 (s, 3 H).

Example 22A (S\*,R\*)-3-[4,6-Bis-(2-methoxyethoxy)-2-(4-bromophenyl)-3-oxo-2,3-dihydrobenzofuran-2-yl]-3-phenylpropanal

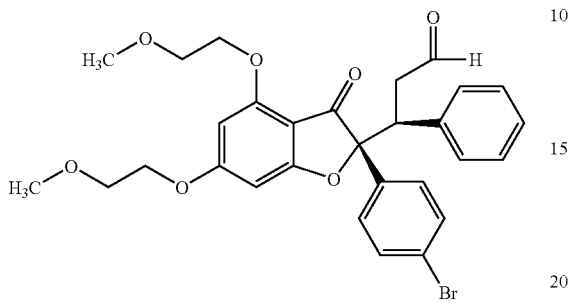

The title compound is prepared in analogy to the synthesis of Example 5A starting from Example 21A.

Yield: 30% of theory.

LC-MS (Method 2): $R_t$=4.48 min.

MS (ESIpos): m/z=570 (M+H)$^+$ $^1$H-NMR (300 MHz, DMSO-d$_6$): δ=9.32 (d, 1 H), 7.67-7.62 (m, 2 H), 7.61-7.55 (m, 2 H), 7.29-7.23 (m, 2 H), 7.20-7.09 (m, 3 H), 6.51 (d, 1 H), 6.04 (d, 1 H), 4.24 (dd, 1 H), 4.22-4.17 (m, 2 H), 4.08-3.93 (m, 2 H), 3.68-3.63 (m, 2 H), 3.54-3.49 (m, 2 H), 3.30 (s, 3 H), 3.22 (s, 3 H), 3.01 (ddd, 1 H), 2.56-2.46 (m, 1 H).

Example 23A 3,5-Bis-(2-chloroethoxy)phenol

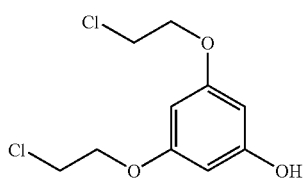

Hydrogen chloride gas is passed into a solution of 150 g (1.19 mol) of phloroglucinol in 1000 ml of 2-chloroethanol at 80° C. over the course of 5 h. Cooling is followed by stirring at RT overnight. The mixture is then heated at 80° C. while continuing to pass in hydrogen chloride gas for 2 h. The mixture is cooled and concentrated, the residue is taken up in a mixture of dichloromethane and water, the phases are separated, and the aqueous phase is extracted twice with dichloromethane. The combined organic phases are dried over sodium sulfate, filtered and concentrated. Column chromatography on silica gel 60 (mobile phase: toluene/ethyl acetate 95:5) results in 81.2 g (27% of theory) of the product.

LC-MS (Method 4): $R_t$=3.27 min.

MS (ESIpos): m/z=252 (M+H)$^+$ $^1$H-NMR (200 MHz, DMSO-d$_6$): δ=9.51 (s, 1 H), 6.03-5.96 (m, 3 H), 4.20-4.13 (m, 4 H), 3.94-3.86 (m, 4 H).

Example 24A

Methyl[3,5-bis-(2-chloroethoxy)phenoxy]-(4-chlorophenyl)acetate

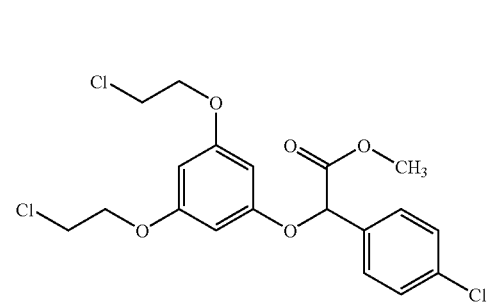

The title compound is prepared in analogy to the synthesis of Example 2A starting from Example 23A.

Yield: 76% of theory.

LC-MS (Method 4): $R_t$=4.05 min.

MS (ESIpos): m/z=433 (M+H)$^+$ $^1$H-NMR (400 MHz, DMSO-d$_6$): δ=7.59-7.54 (m, 2 H), 7.52-7.46 (m, 2 H), 6.23-6.18 (m, 3 H), 6.13 (s, 1 H), 4.24-4.19 (m, 4 H), 3.93-3.88 (m, 4 H), 3.67 (s, 3 H).

Example 25A

[3,5-Bis-(2-chloroethoxy)phenoxy]-(4-chlorophenyl)acetic acid

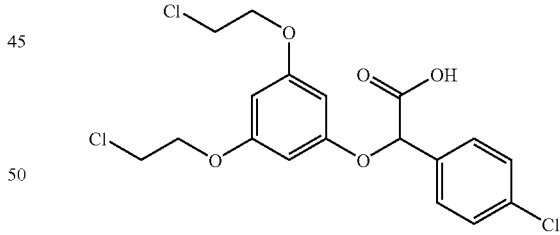

The title compound is prepared in analogy to the synthesis of Example 3A starting from Example 24A.

Yield: 92% of theory.

LC-MS (Method 4): $R_t$=3.91 min.

MS (ESIpos): m/z=419 (M+H)$^+$ $^1$H-NMR (200 MHz, DMSO-d$_6$): δ=13.4 (s, 1 H), 7.61-7.53 (m, 2 H), 7.52-7.45 (m, 2 H), 6.19 (s, 3 H), 5.92 (s, 1 H), 4.25-4.16 (m, 4 H), 3.96-3.88 (m, 4 H).

Example 26A 4,6-Bis-(2-chloroethoxy)-2-(4-chlorophenyl)-benzofuran-3(2H)-one

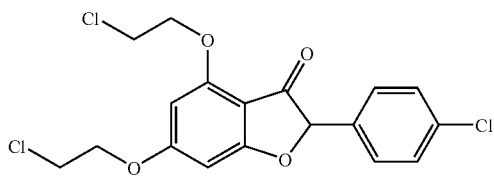

The title compound is prepared in analogy to the synthesis of Example 4A starting from Example 25A.

Yield: 55% of theory.

LC-MS (Method 3): $R_t$=3.82 min.

MS (ESIpos): m/z=401 (M+H)$^+$ $^1$H-NMR (300 MHz, DMSO-$d_6$): δ=7.51-7.45 (m, 2 H), 7.36-7.30 (m, 2 H), 6.57 (d, 1 H), 6.32 (d, 1 H), 5.79 (s, 1 H), 4.45-4.35 (m, 4 H), 4.02-3.89 (m, 4 H).

Example 27A (S*,R*)-3-[4,6-Bis-(2-chloroethoxy)-2-(4-chlorophenyl)-3-oxo-2,3-dihydrobenzofuran-2-yl]-3-phenyl-propanal

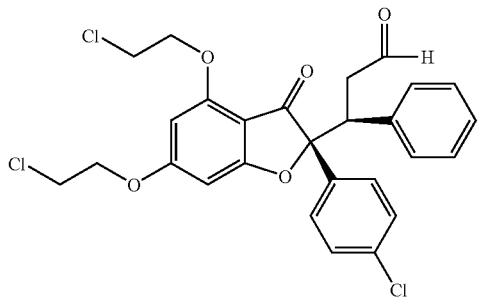

The title compound is prepared in analogy to the synthesis of Example 5A starting from Example 26A.

Yield: 48% of theory.

LC-MS (Method 4): $R_t$=3.72 min.

MS (ESIpos): m/z=533 (M+H)$^+$ $^1$H-NMR (200 MHz, DMSO-$d_6$): δ=9.33 (d, 1 H), 7.68-7.62 (m, 2 H), 7.54-7.48 (m, 2 H), 7.29-7.24 (m, 2 H), 7.19-7.09 (m, 3 H), 6.57 (d, 1 H), 6.09 (d, 1 H), 4.40-4.35 (m, 2 H), 4.30-4.09 (m, 3 H), 3.99-3.94 (m, 2 H), 3.81-3.76 (m, 2 H), 3.02 (ddd, 1 H), 2.56-2.46 (m, 1 H).

Example 28A (1S*,3S*,3aR*,8bS*)-6,8-Bis-(2-chloroethoxy)-3a-(4-chlorophenyl)-3-phenyl-2,3,3a,8b-tetrahydrocyclopenta[b]benzofuran-1,8b-(1H)-diol

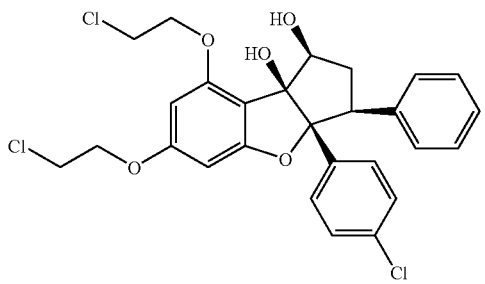

The title compound is prepared in analogy to the synthesis of Example 6A starting from Example 27A.

Yield: 31% of theory.

LC-MS (Method 5): $R_t$=4.01 min.

MS (ESIpos): m/z=535 (M+H)$^+$ $^1$H-NMR (300 MHz, DMSO-$d_6$): δ=7.26-7.15 (m, 4 H), 7.10-7.03 (m, 3 H), 6.92-6.86 (m, 2 H), 6.38 (d, 1 H), 6.25 (d, 1 H), 5.68 (d, 1 H), 4.83 (s, 1 H), 4.82-4.73 (m, 1 H), 4.36-4.28 (m, 4 H), 4.02-3.93 (m, 4 H), 3.29-3.23 (m, 1 H), 2.51-2.43 (m, 1 H), 2.17 (ddd, 1 H).

Example 29A (3S*,3aR*,8bR*)-6,8-Bis-(2-chloroethoxy)-3a-(4-chlorophenyl)-8b-hydroxy-3-phenyl-2,3,3a,8b-tetrahydrocyclopenta[b]benzofuran-1-one

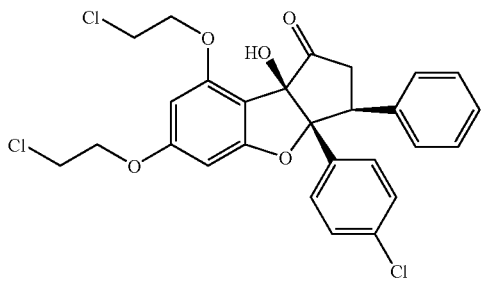

The title compound is prepared in analogy to the synthesis of Example 7A starting from Example 28A.

Yield: 71% of theory.

LC-MS (Method 2): $R_t$=3.40 min.

MS (ESIpos): m/z=533 (M+H)$^+$ $^1$H-NMR (300 MHz, DMSO-$d_6$): δ=7.21-7.15 (m, 2 H), 7.12-7.05 (m, 3 H), 7.02-6.96 (m, 4 H), 6.54 (d, 1 H), 6.30 (d, 1 H), 5.87 (s, 1 H), 4.36-4.26 (m, 4 H), 3.99-3.94 (m, 2 H), 3.90-3.85 (m, 2 H), 3.73 (dd, 1 H), 3.11 (dd, 1 H), 2.93 (dd, 1 H).

Example 30A (1R*,3S*,3aR*,8bS*)-6,8-Bis-(2-chloroethoxy)-3a-(4-chlorophenyl)-3-phenyl-2,3,3a,8b-tetrahydrocyclopenta[b]benzofuran-1,8b-(1H)-diol

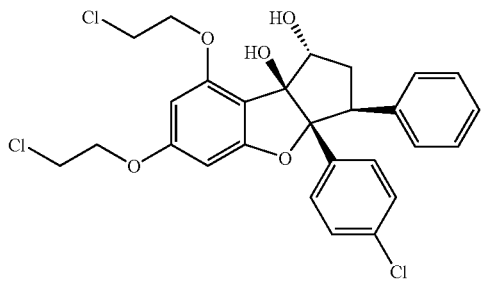

The title compound is prepared in analogy to the synthesis of Example 8A starting from Example 29A.
Yield: 85% of theory.
LC-MS (Method 1): $R_t$=4.09 min.
MS (ESIpos): m/z=535 (M+H)$^+$
$^1$H-NMR (300 MHz, DMSO-d$_6$): δ=7.11-6.98 (m, 9 H), 6.33 (d, 1 H), 6.21 (d, 1 H), 4.97 (s, 1 H), 4.55-4.50 (m, 1 H), 4.36 (d, 1 H), 4.32-4.26 (m, 4 H), 4.02-3.90 (m, 5 H), 2.72 (ddd, 1 H), 2.03 (ddd, 1 H).

Example 31A

Methyl[3,5-Bis-(2-chloroethoxy)phenoxy]-(4-bromophenyl)acetate

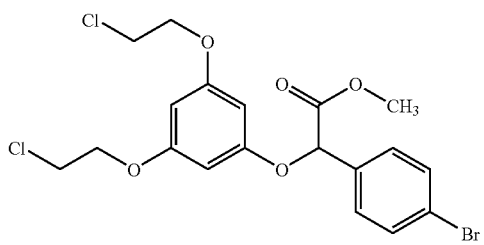

The title compound is prepared in analogy to the synthesis of Example 2A starting from Example 23A.
Yield: 48% of theory.
LC-MS (Method 4): $R_t$=4.11 min.
MS (ESIpos): m/z=477 (M+H)$^+$
$^1$H-NMR (400 MHz, DMSO-d$_6$): δ=7.68-7.60 (m, 2 H), 7.54-7.45 (m, 2 H), 6.23-6.18 (m, 3 H), 6.13 (s, 1 H), 4.25-4.17 (m, 4 H), 3.95-3.87 (m, 4 H), 3.66 (s, 3 H).

Example 32A

[3,5-Bis-(2-chloroethoxy)phenoxy]-(4bromophenyl)acetic acid

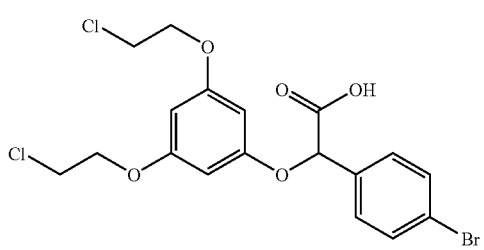

The title compound is prepared in analogy to the synthesis of Example 3A starting from Example 31A.
Yield: 99% of theory.
LC-MS (Method 2): $R_t$=4.33 min.
MS (ESIpos): m/z=463 (M+H)$^+$
$^1$H-NMR (300 MHz, DMSO-d$_6$): δ=13.4 (s, 1 H), 7.64-7.58 (m, 2 H), 7.52-7.46 (m, 2 H), 6.21-6.16 (m, 3 H), 5.85 (s, 1 H), 4.24-4.18 (m, 4 H), 3.93-3.88 (m, 4 H).

Example 33A 4,6-Bis-(2-chloroethoxy)-2-(4-bromophenyl)benzofuran-3(2H)-one

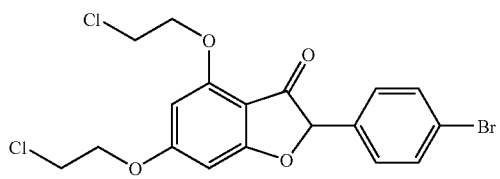

The title compound is prepared in analogy to the synthesis of Example 4A starting from Example 32A.
Yield: 16% of theory.
LC-MS (Method 4): $R_t$=3.96 min.
MS (ESIpos): m/z=446 (M+H)$^+$
$^1$H-NMR (200 MHz, DMSO-d$_6$): δ=7.66-7.57 (m, 2 H), 7.30-7.22 (m, 2 H), 6.58 (d, 1 H), 6.32 (d, 1 H), 5.79 (s, 1 H), 4.46-4.34 (m, 4 H), 4.04-3.88 (m, 4 H).

Example 34A (S*,R*)-3-[4,6-Bis-2-chloroethoxy)-2-(4-bromophenyl)-3-oxo-2,3-dihydrobenzofuran-2-yl]-3-phenylpropanal

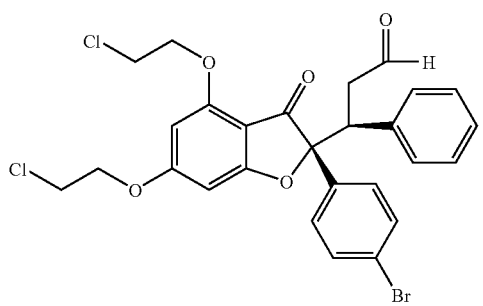

The title compound is prepared in analogy to the synthesis of Example 5A starting from Example 33A.
Yield: 35% of theory.
LC-MS (Method 4): $R_t$=4.05 min.
MS (ESIpos): m/z=578 (M+H)$^+$
$^1$H-NMR (200 MHz, DMSO-d$_6$): δ=9.33 (d, 1 H), 7.70-7.63 (m, 2 H), 7.62-7.54 (m, 2 H), 7.31-7.09 (m, 5 H), 6.58 (d, 1 H), 6.10 (d, 1 H), 4.42-4.33 (m, 2 H), 4.31-4.07 (m, 3 H), 4.02-3.93 (m, 2 H), 3.83-3.76 (m, 2 H), 3.03 (ddd, 1 H), 2.58-2.44 (m, 1 H).

Example 35A (1S*,3S*,3aR*,8bS*)-6,8-Bis-(2-chloroethoxy)-3a-(4-bromophenyl)-3-phenyl-2,3,3a,8b-tetrahydrocyclopenta[b]benzofuran-1,8b -(1H)-diol

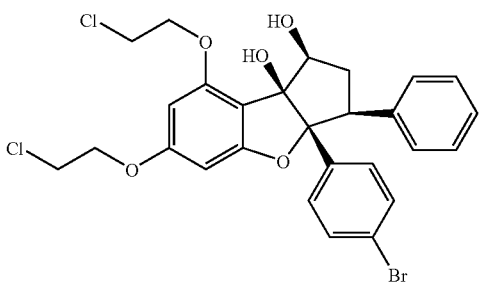

The title compound is prepared in analogy to the synthesis of Example 6A starting from Example 34A.
Yield: 30% of theory.
LC-MS (Method 2): $R_t$=4.60 min.
MS (ESIpos): m/z=579 (M+H)$^+$
$^1$H-NMR (400 MHz, DMSO-d$_6$): δ=7.34-7.28 (m, 2 H), 7.18-7.12 (m, 2 H), 7.09-7.03 (m, 3 H), 6.92-6.87 (m, 2 H), 6.37 (d, 1 H), 6.25 (d, 1 H), 5.68 (d, 1 H), 4.83 (s, 1 H), 4.81-4.73 (m, 1 H), 4.35-4.27 (m, 4 H), 4.01-3.93 (m, 4 H), 3.28-3.23 (m, 1 H), 2.54-2.42 (m, 1 H), 2.17 (ddd, 1 H).

Example 36A

Methyl(4-chlorophenyl)-(3-ethoxyphenoxy)acetate

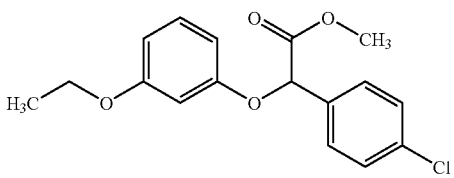

The title compound is prepared in analogy to the synthesis of Example 2A starting from 3-ethoxyphenol.
Yield: 97% of theory.
LC-MS (Method 5): $R_t$=3.86 min.
MS (ESIpos): m/z=321 (M+H)$^+$
$^1$H-NMR (300 MHz, DMSO-d$_6$): δ=7.57 (d, 2 H), 7.49 (d, 2 H), 7.19-7.13 (m, 1 H), 6.54-6.52 (m, 3 H), 6.07 (s, 1 H), 3.98 (q, 2 H), 3.66 (s, 3 H), 1.29 (t, 3 H).

Example 37A (4-Chlorophenyl)(3-ethoxyphenoxy)acetic acid

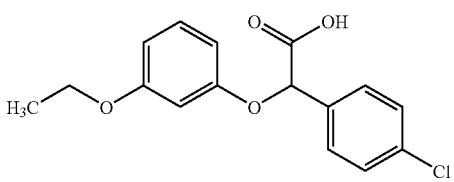

The title compound is prepared in analogy to the synthesis of Example 3A starting from Example 36A.
Yield: 96% of theory.
LC-MS (Method 4): $R_t$=3.18 min.
MS (ESIpos): m/z=307 (M+H)$^+$
$^1$H-NMR (200 MHz, DMSO-d$_6$): δ=7.58 (d, 2 H), 7.48 (d, 2 H), 7.20-7.12 (m, 1 H), 6.55-6.50 (m, 3 H), 5.88 (s, 1 H), 3.98 (q, 2 H), 1.30 (t, 3 H).

Example 38A 2-(4-Chlorophenyl)-6-ethoxybenzofuran-3(2H)-one

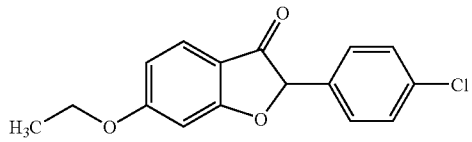

The title compound is prepared in analogy to the synthesis of Example 4A starting from Example 37A.
Yield: 26% of theory.
LC-MS (Method 2): $R_t$=3.37 min.
MS (ESIpos): m/z=289 (M+H)$^+$.

Example 39A (S*,R*)-3-[2-(4-Chlorophenyl)-6-ethoxy-3-oxo-2,3-dihydrobenzofuran-2-yl]-3-phenylpropanal

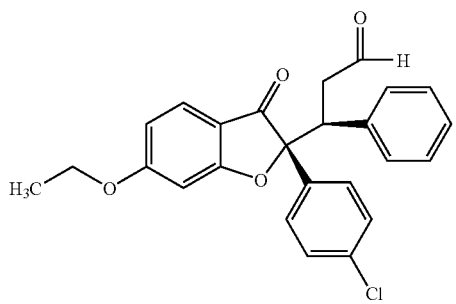

The title compound is prepared in analogy to the synthesis of Example 5A starting from Example 38A.
Yield: 19% of theory (pure diastereomer)
LC-MS (Method 12): $R_t$=4.53 min.
MS (ESIpos): m/z=421 (M+H)$^+$
$^1$H-NMR (400 MHz, DMSO-d$_6$): δ=9.34 (s, 1 H), 7.69 (d, 2 H), 7.52 (d, 2 H), 7.24 (d, 2 H), 7.18-7.06 (m, 4 H), 6.90 (s, 1 H), 6.50 (dd, 1 H), 4.28 (dd, 1 H), 4.14 (q, 2 H), 3.12-3.04 (m, 1 H), 2.57-2.52 (m, 1 H), 1.34 (t, 3 H).

Example 40A (2R*,3S*,3aR*,8bR*)-3a-(4-Chlorophenyl)-6-ethoxy-8b-hydroxy-1-oxo-3-phenyl-2,3,3a,8b-tetrahydro-1H-cyclopenta[b]benzofuran-2-carboxylic acid

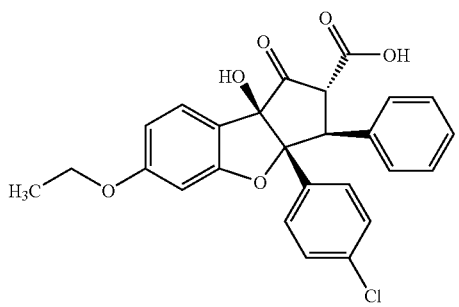

The title compound is prepared in analogy to the synthesis of Example 17A starting from Example 24. The compound is employed directly in the next stage without further characterization.

Example 41A 4-(2-Chloroethoxy)-2-hydroxyacetophenone

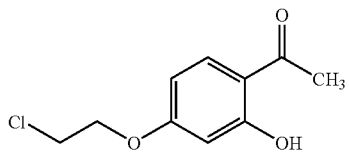

300 g (1.97 mol) of 2,4-dihydroxyacetophenone, 238 g (2.96 mol) of 2-chloroethanol and 776 g (2.96 mol) of triphenylphosphine are introduced into 4800 ml of THF. At RT 380 g (2.96 mol) of diisopropyl azodicarboxylate are added dropwise as solution in 1200 ml of THF. The mixture is heated under RF for 16 h and then cooled and concentrated. The residue is stirred with 2 N sodium hydroxide solution and filtered with suction. The solid is stirred with ethyl acetate, filtered with suction and washed with ethyl acetate, and the solid is dried. The solid is taken up in a mixture of 4 N hydrochloric acid and ethyl acetate, the phases are separated and the aqueous phase is extracted once more with ethyl acetate. The combined organic phases are washed with saturated sodium chloride solution, dried over sodium sulfate, filtered and concentrated. Column chromatography twice on silica gel 60 (1st mobile phase: toluene, 2nd mobile phase: cyclohexane) results in 232 g (55% of theory) of the product.

LC-MS (Method 13): $R_t$=2.41 min.

MS (ESIpos): m/z=215 (M+H)$^+$ $^1$H-NMR (200 MHz, DMSO-d$_6$): δ=12.6 (s, 1 H), 7.86 (d, 1 H), 6.57 (dd, 1 H), 6.50 (d, 1 H), 4.38-4.30 (m, 2 H), 4.00-3.92 (m, 2 H), 2.57 (s, 3 H).

Example 42A 6-(2-Chloroethoxy)-benzofuran-3-one

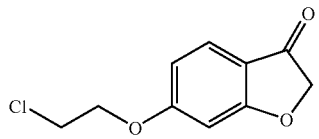

76.0 g (354 mmol) of 4-(2-chloroethoxy)-2-hydroxyacetophenone are introduced into 1050 ml of THF at −78° C. under argon, and 148 g (885 mmol) of lithium hexamethyldisilazide are added dropwise as solution in 750 ml of THF. Warming to RT and addition of 96.2 g (885 mmol) of chlorotrimethylsilane are followed by stirring at RT for 2 h. Then, at 0° C., 65.6 g (369 mmol) of N-bromosuccinimide are added in portions, and the mixture is stirred at 0° C. for 0.5 h and at RT for 1 h. Then 369 ml of 1 N sodium hydroxide solution are added, and the mixture is stirred at RT for 0.5 h. After addition of saturated ammonium chloride solution, the aqueous phase is extracted several times with diethyl ether, and the combined organic phases are dried over sodium sulfate, filtered and concentrated. Gradient chromatography on silica gel 60 (mobile phase: petroleum ether/ethyl acetate) results in 59.0 g (78% of theory) of the product.

LC-MS (Method 6): $R_t$=1.80 min.

MS (ESIpos): m/z=213 (M+H)$^+$ $^1$H-NMR (300 MHz, DMSO-d$_6$): δ=7.54 (d, 1 H), 6.86 (d, 1 H), 6.73 (dd, 1 H), 4.77 (s, 2 H), 4.41-4.36 (m, 2 H), 4.00-3.95 (m, 2 H).

Example 43A

2-Bromo-6-(2-chloroethoxy)benzofuran-3-one

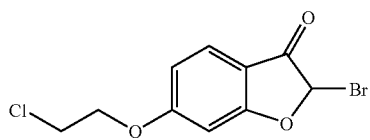

Method a):

127 g (597 mmol) of 6-(2-chloroethoxy)benzofuran-3-one are dissolved in 1850 ml of dioxane and 1850 ml of diethyl ether under argon at RT and cooled to −5° C. While stirring vigorously, 95.6 g (597 mmol) of bromine are slowly added dropwise, and the mixture is stirred at 0° C. for 1 h. It is then added to ice-water, the phases are separated, the aqueous phase is extracted twice with dichloromethane, and the combined organic phases are dried over sodium sulfate, filtered and concentrated. Column chromatography on silica gel 60 (mobile phase: toluene) results in 150 g (86% of theory) of the product as hydrate.

Method b):

5.00 g (23.5 mmol) of 6-(2-chloroethoxy)benzofuran-3-one in 30 ml of chloroform are added to a boiling suspension of 10.5 g (47.0 mmol) of copper(II) bromide in 60 ml of ethyl acetate. The mixture is heated under RF overnight. After cooling, the solid is filtered off and washed with ethyl acetate. The filtrate is washed with water and saturated aqueous sodium chloride solution, dried over sodium sulfate, filtered and concentrated. Gradient chromatography on silica gel 60 (mobile phase: toluene/cyclohexane) results in 1.50 g (20% of theory) of the product as hydrate.

LC-MS (Method 2): $R_t$=4.13 min.

MS (ESIpos): m/z=291 (M+H)$^+$ $^1$H-NMR (400 MHz, DMSO-d$_6$): δ=7.52 (d, 1 H), 7.30 (s, 2 H), 6.75 (d, 1 H), 6.70 (dd, 1 H), 5.57 (s, 1 H), 4.42-4.37 (m, 2 H), 4.00-3.95 (m, 2 H).

Example 44A

2-Bromo-3-tert-butyldimethylsilyloxy-6-(2-chloroethoxy)benzofuran

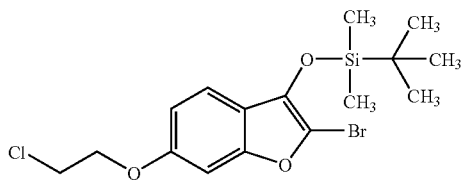

1.50 g (5.15 mmol) of the hydrate of 2-bromo-6-(2-chloroethoxy)benzofuran-3-one (Example 43A) are concentrated three times with toluene under argon in order to remove water azeotropically. The residue is then dissolved under argon in 25 ml of diethyl ether and cooled to 0° C. 0.79 ml (5.66 mmol) of TEA and 1.30 ml (5.66 mmol) of tert-butyldimethylsilyl trifluoromethanesulfonate are successively slowly added dropwise, and the mixture is stirred at 0° C. for 10 min and at RT for 1 h. The diethyl ether phase is then separated off, the residue is extracted twice with diethyl ether, and the combined diethyl ether phases are concentrated. Column chromatography on silica gel 60 (mobile phase: cyclohexane) results in 2.00 g (96% of theory) of the product.

LC-MS (Method 2): $R_t$=4.92 min.

MS (ESIpos): m/z=405 (M+H)$^+$ $^1$H-NMR (400 MHz, DMSO-d$_6$): δ=7.36 (d, 1 H), 7.21 (d, 1 H), 6.96 (dd, 1 H), 4.32-4.27 (m, 2 H), 3.98-3.93 (m, 2 H), 1.03 (s, 9 H), 0.23 (s, 6 H).

Example 45A 3-tert-Butyldimethylsilyloxy-6-(2-chloroethoxy)-2-(4-chlorophenyl)-benzofuran

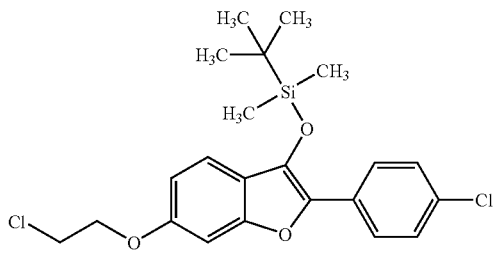

Method a):

2.00 g (4.93 mmol) of 2-bromo-3-tert-butyldimethylsilyloxy-6-(2-chloroethoxy)benzofuran are dissolved in 41 ml of toluene under argon, and 0.92 g (5.91 mmol) of 4-chlorophenylboronic acid and a solution of 1.15 g (10.8 mmol) of sodium carbonate in 5.4 ml of water are added. The mixture is degassed and ventilated twice with argon, 0.28 g (0.25 mmol) of tetrakis(triphenylphosphine)palladium(0) is added, and the mixture is heated at 95° C. for 2 h. After cooling, the reaction mixture is poured into a mixture of ice-cold saturated ammonium chloride solution and diethyl ether, the phases are separated, the aqueous phase is extracted twice with diethyl ether, and the combined organic phases are washed with water and saturated brine, dried over sodium sulfate, filtered and concentrated. Column chromatography on silica gel 60 (mobile phase: toluene/cyclohexane 1:1) results in 1.69 g (78% of theory) of the product.

Method b):

39.4 g (135 mmol) of the hydrate of 2-bromo-6-(2-chloroethoxy)benzofuran-3-one (Example 43A) are concentrated three times with toluene under argon to remove water azeotropically. The residue is then dissolved in 1200 ml of toluene under argon and cooled to −10° C. 22.7 ml (162 mmol) of TEA and 34.2 ml (149 mmol) of tert-butyldimethylsilyl trifluoromethanesulfonate are successively slowly added dropwise, and the mixture is stirred at 0° C. for 0.5 h and at RT for 0.5 h. The lower triethylamine trifluoromethanesulfonic acid salt phase is then separated off, and the supernatant solution is added without further purification to 25.4 g (162 mmol) of 4-chlorophenylboronic acid under argon. Addition of 31.6 g (298 mmol) of sodium carbonate as solution in 148 ml of water is followed by degassing by application of vacuum and ventilation with argon. 7.82 g (6.76 mmol) of tetrakis(triphenylphosphine)palladium(0) are added, and the mixture is degassed and ventilated with argon. It is heated at 95° C. while stirring vigorously for 2 h. After cooling, the phases are separated, and the organic phase is washed three times with saturated ammonium chloride solution, once with water and once with saturated sodium chloride solution, dried over magnesium sulfate, filtered and concentrated. Column chromatography on silica gel 60 (mobile phase: toluene/cyclohexane 1:1) results in 53.1 g (90% of theory) of the product, which is still contaminated with 9% 4,4'-dichlorobiphenyl.

MS (DCI): m/z=437 (M+H)$^+$ $^1$H-NMR (400 MHz, DMSO-d$_6$): δ=7.83-7.77 (m, 2 H), 7.56-7.51 (m, 2 H), 7.43 (d, 1 H), 7.21 (d, 1 H), 6.95 (dd, 1 H), 4.35-4.30 (m, 2 H), 3.99-3.94 (m, 2 H), 1.02 (s, 9 H), 0.12 (s, 6 H).

Example 46A 6-(2-Chloroethoxy)-2-(4-chlorophenyl)benzofuran-3(2H)-one

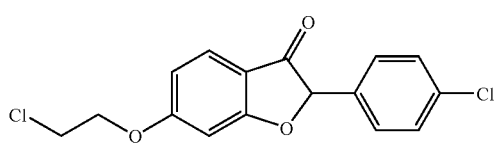

66.5 g (152 mmol) of 3-tert-butyldimethylsilyloxy-6-(2-chloroethoxy)-2-(4-chlorophenyl)benzofuran are dissolved in 500 ml of a 4 M hydrogen chloride solution in dioxane at RT under argon and stirred for 1.5 h. The mixture is concentrated to result in 49.2 g of a residue which is stored under argon and reacted further without purification.

LC-MS (Method 5): $R_t$=3.77 min.
MS (ESIpos): m/z=323 (M+H)$^+$.

Example 47A (S*,R*)-3-[6-(2-Chloroethoxy)-2-(4-chlorophenyl)-3-oxo-2,3-dihydrobenzofuran-2-yl]-3-phenylpropanal

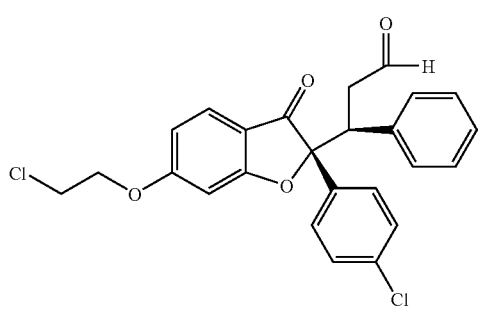

The title compound is prepared in analogy to the synthesis of Example 5A starting from Example 46A.

Yield: 31% of theory.
LC-MS (Method 4): $R_t$=3.73 min.
MS (ESIpos): m/z=455 (M+H)$^+$
$^1$H-NMR (200 MHz, DMSO-d$_6$): δ=9.34 (d, 1 H), 7.75-7.66 (m, 2 H), 7.58-7.49 (m, 2 H), 7.30-7.05 (m, 6 H), 6.98 (d, 1 H), 6.56 (dd, 1 H), 4.43-4.34 (m, 2 H), 4.30 (dd, 1 H), 4.02-3.94 (m, 2 H), 3.09 (ddd, 1 H), 2.55 (dd, 1 H).

Example 48A (1S*,3S*,3aR*,8bS*)-6-(2-Chloroethoxy)-3a-(4-chlorophenyl)-3-phenyl-2,3,3a,8b-tetrahydrocyclopenta[b]benzofuran-1,8b-(1H)-diol

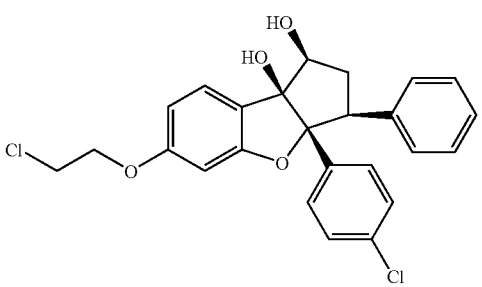

The title compound is prepared in analogy to the synthesis of Example 6A starting from Example 47A.

Yield: 94% of theory.
LC-MS (Method 6): $R_t$=2.73 min.
MS (ESIpos): m/z=457 (M+H)$^+$
$^1$H-NMR (200 MHz, DMSO-d$_6$): δ=7.32-7.02 (m, 8 H), 6.96-6.88 (m, 2 H), 6.72 (d, 1 H), 6.62 (dd, 1 H), 5.86 (d, 1 H), 5.07 (s, 1 H), 4.45 (q, 1 H), 4.34-4.25 (m, 2 H), 4.00-3.93 (m, 2 H), 3.40-3.25 (m, 1 H), 2.49-2.36 (m, 1 H), 2.20 (ddd, 1 H).

Example 49A (1S*,3S*,3aR*,8bS*)-6-(2-Azidoethoxy)-3a-(4-chlorophenyl)-3-phenyl-2,3,3a,8b-tetrahydrocyclopenta[b]benzofuran-1,8b-(1H)-diol

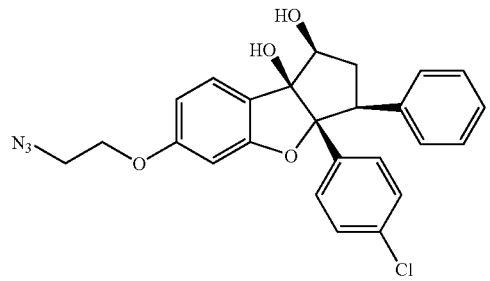

56.9 mg (0.87 mmol) of sodium azide are added to 200 mg (0.44 mmol) of (1S*,3S*,3aR*,8bS*)-6-(2-chloroethoxy)-3a-(4-chlorophenyl)-3-phenyl-2,3,3a,8b-tetrahydrocyclopenta[b]benzofuran-1,8b-(1H)-diol (Example 48A) in 4 ml of DMF under argon, and the mixture is heated at 100° C. overnight. After cooling and concentration, the residue is taken up in water and dichloromethane, the phases are separated, the aqueous phase is extracted twice with dichloromethane, and the combined organic phases are washed with saturated sodium chloride solution, dried over magnesium sulfate, filtered and concentrated. Gradient chromatography on silica gel 60 (mobile phase: toluene/ethyl acetate) results in 190 mg (94% of theory) of the product.

LC-MS (Method 9): $R_t$=2.66 min.
MS (ESIpos): m/z=464 (M+H)$^+$
$^1$H-NMR (200 MHz, DMSO-d$_6$): δ=7.29 (d, 1 H), 7.26-7.02 (m, 7 H), 6.96-6.90 (m, 2 H), 6.71 (d, 1 H), 6.61 (dd, 1 H), 5.83 (d, 1 H), 5.02 (s, 1 H), 4.49-4.41 (m, 1 H), 4.24-4.19 (m, 2 H), 3.69-3.63 (m, 2 H), 3.34-3.25 (m, 1 H), 2.50-2.40 (m, 1 H), 2.21 (ddd, 1 H).

Preparative separation of the racemate into the enantiomers is carried out by HPLC on a chiral phase by method 25A.

Analytical Data (Method 25B):
Enantiomer A: $R_t$=5.52 min., enantiomer B: $R_t$=8.56 min.

Example 50A (3S*,3aR*,8bR*)-6-(2-Chloroethoxy)-3a-(4-chlorophenyl)-8b-hydroxy-3-phenyl-2,3,3a,8b-tetrahydrocyclopenta[b]benzofuran-1-one

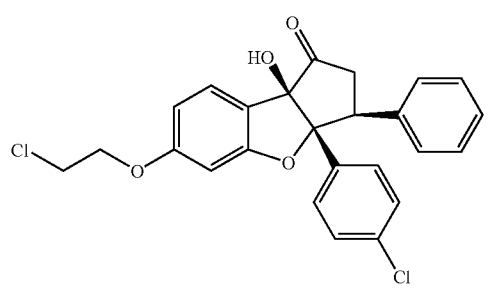

The title compound is prepared in analogy to the synthesis of Example 7A starting from Example 48A.

Yield: 92% of theory.

LC-MS (Method 4): $R_t$=3.54 min.

MS (ESIpos): m/z=455 (M+H)$^+$ $^1$H-NMR (200 MHz, DMSO-$d_6$): δ=7.29-7.00 (m, 10 H), 6.89 (d, 1 H), 6.66 (dd, 1 H), 6.31 (s, 1 H), 4.36-4.28 (m, 2 H), 4.02-3.94 (m, 2 H), 3.65 (dd, 1 H), 3.42-3.20 (m, 1 H), 2.84 (dd, 1 H).

Example 51A (1R*,3S*,3aR*,8bS*)-6-(2-Chloroethoxy)-3a-(4-chlorophenyl)-3-phenyl-2,3,3a,8b-tetrahydrocyclopenta[b]benzofuran-1,8b-(1H)-diol

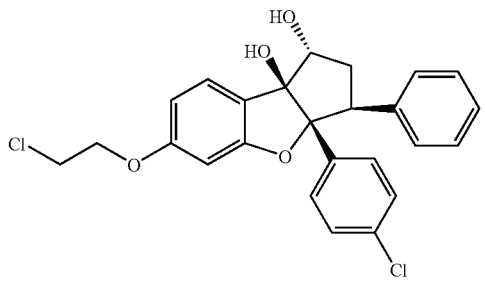

The title compound is prepared in analogy to the synthesis of Example 8A starting from Example 50A.

Yield: 99% of theory.

LC-MS (Method 2): $R_t$=4.24 min.

MS (ESIneg): m/z=501 (M−H)$^−$ $^1$H-NMR (200 MHz, DMSO-$d_6$): δ=7.32 (d, 1 H), 7.14-6.91 (m, 9 H), 6.66 (d, 1 H), 6.55 (dd, 1 H), 5.26 (s, 1 H), 5.17 (d, 1 H), 4.62-4.51 (m, 1 H), 4.32-4.24 (m, 2 H), 4.00-3.92 (m, 2 H), 3.90-3.77 (m, 1 H), 2.66 (dt, 1 H), 1.98-1.83 (m, 1 H).

Example 52A (2R*,3S*,3aR*,8bR*)-6-(2-Chloroethoxy)-3a-(4-chlorophenyl)-8b-hydroxy-1-oxo-3-phenyl-2,3,3a,8b-tetrahydrocyclopenta[b]benzofuran-2-carboxylic acid

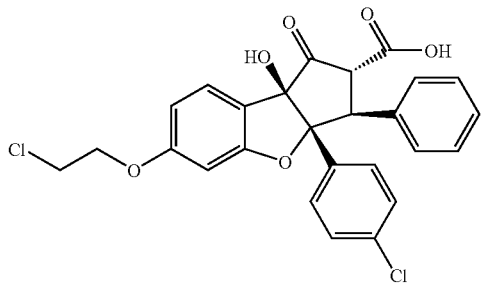

The title compound is prepared in analogy to the synthesis of Example 17A starting from Example 50A. The compound is employed in the next stage without further purification.

Example 53A (2R*,3S*,3aR*,8bR*)-6-(2-Chloroethoxy)-3a-(4-chlorophenyl)-2-dimethylcarbamid-8b-hydroxy-3-phenyl-2,3,3a,8b-tetrahydrocyclopenta[b]benzofuran-1-one

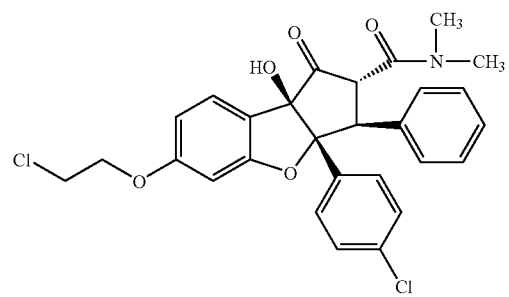

The title compound is prepared in analogy to the synthesis of Example 16 starting from Example 52A.

Yield: 14% of theory (starting from Example 50A)

LC-MS (Method 13): $R_t$=2.71 min.

MS (ESIpos): m/z=526 (M+H)$^+$ $^1$H-NMR (200 MHz, DMSO-$d_6$): δ=7.23-7.16 (m, 5 H), 7.14-7.05 (m, 3 H), 7.02-6.94 (m, 2 H), 6.89 (d, 1 H), 6.64 (dd, 1 H), 6.47 (s, 1 H), 4.79 (d, 1 H), 4.38-4.29 (m, 2 H), 4.19 (d, 1 H), 4.02-3.94 (m, 2 H), 3.28 (s, 3 H), 2.77 (s, 3 H).

Example 54A (1R*,2R*,3S*,3aR*,8bS*)-6-(2-Chloroethoxy)-3a-(4-chlorophenyl)-2-dimethylcarbamid-3-phenyl-2,3,3a,8b-tetrahydrocyclopenta[b]benzofuran-1,8b-(1H)-diol

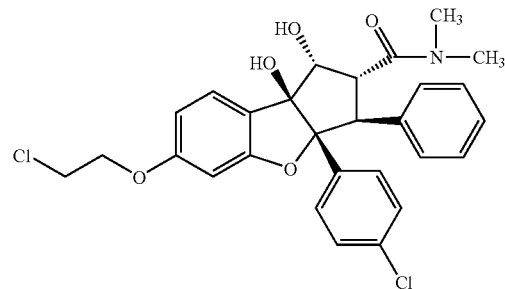

The title compound is prepared in analogy to the synthesis of Example 17 starting from Example 53A.

Yield: 81% of theory.

LC-MS (Method 6): $R_t$=2.31 min.

MS (ESIpos): m/z=528 (M+H)$^+$ $^1$H-NMR (200 MHz, DMSO-$d_6$): δ=7.36 (d, 1 H), 7.23-7.10 (m, 4 H), 7.06-6.96 (m, 3 H), 6.86-6.79 (m, 2 H), 6.70 (d, 1 H), 6.55 (dd, 1 H), 5.50 (d, 1 H), 5.32 (s, 1 H), 4.92-4.82 (m, 1 H), 4.34-4.23 (m, 2 H), 4.20-3.93 (m, 4 H), 3.20 (s, 3 H), 2.72 (s, 3 H).

Example 55A (3S*,3aR*,8bR*)-6-(2-Chloroethoxy)-3a-(4-chlorophenyl)-8b-hydroxy-3-phenyl-2,3,3a,8b-tetrahydrocyclopenta[b]benzofuran-1-oxime

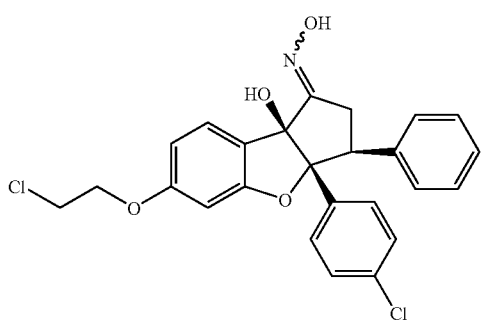

The title compound is prepared in analogy to the synthesis of Example 14 starting from Example 50A.

Yield: 82% of theory.

LC-MS (Method 6): $R_t$=2.55 min.

MS (ESIneg): m/z=468 (M−H)⁻

$^1$H-NMR (300 MHz, DMSO-$d_6$): δ=11.1 (s, 1 H), 7.35 (d, 1 H), 7.23-7.06 (m, 7 H), 7.02-6.97 (m, 2 H), 6.79 (d, 1 H), 6.65 (dd, 1 H), 5.78 (s, 1 H), 4.34-4.28 (m, 2 H), 3.99-3.93 (m, 2 H), 3.45 (t, 1 H), 3.03 (d, 2 H).

Example 56A (1R*,3S*,3aR*,8bS*)-6-(2-Chloroethoxy)-3a-(4-chlorophenyl)-8b-hydroxy-3-phenyl-2,3,3a,8b-tetrahydrocyclopenta[b]benzofuran-1-amine

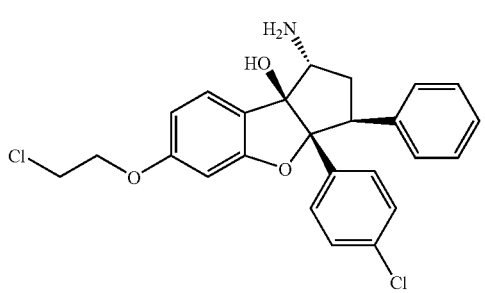

The title compound is prepared in analogy to the synthesis of Example 15 starting from Example 55A.

Yield: 89% of theory.

LC-MS (Method 6): $R_t$=1.89 min.

MS (ESIpos): m/z=456 (M+H)⁺

$^1$H-NMR (200 MHz, DMSO-$d_6$): δ=7.27-6.90 (m, 10 H), 6.69 (d, 1 H), 6.58 (dd, 1 H), 4.32-4.24 (m, 2 H), 3.99-3.92 (m, 2 H), 3.62 (dd, 1 H), 3.43 (dd, 1 H), 2.44-2.31 (m, 1 H), 2.25-2.02 (m, 1 H).

Example 57A

4-Benzyloxy-6-hydroxyacetophenone

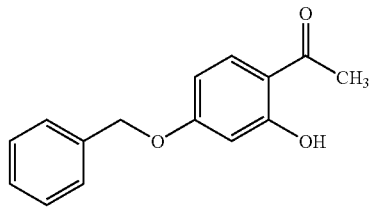

41 ml (345 mmol) of benzyl bromide and 47.69 g (345 mmol) of potassium carbonate are added to a solution of 50.00 g (329 mmol) of 2,4-dihydroxyacetophenone in 500 ml of DMF, and the resulting suspension is stirred at room temperature overnight. The solid is then filtered off with suction through a glass frit, and the filtrate is poured into 200 ml of water and 200 ml of ethyl acetate. The phases are separated and the organic phase is washed with saturated ammonium chloride solution, water, saturated sodium bicarbonate solution and saturated sodium chloride solution, dried over magnesium sulfate, filtered and concentrated. Crystallization from a diethyl ether/petroleum ether mixture results in 56.40 g (71% of theory) of the title substance as pink-colored crystals.

LC-MS (Method 1): $R_t$=3.70 min.

MS (ESIpos): m/z=243 (M+H)⁺

$^1$H-NMR (300 MHz, DMSO-$d_6$): δ=12.60 (s, 1 H), 7.85 (d, 1 H), 7.48-7.31 (m, 5 H), 6.60 (dd, 1 H), 6.55 (d, 1 H), 5.19 (s, 2 H), 2.56 (s, 3 H).

Example 58A

6-Benzyloxy-benzofuran-3-one

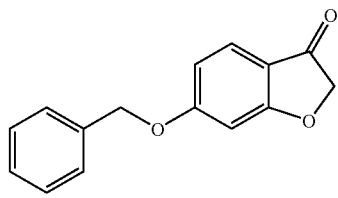

10 g (41.28 mmol) of 4-benzyloxy-6-hydroxyacetophenone suspended in 30 ml of chloroform are added to a boiling suspension of 18.44 g (82.55 mmol) of copper(II) bromide in 70 ml of ethyl acetate, and the suspension is heated under reflux overnight. The still hot solution is then filtered, and the filter cake is washed with ethyl acetate. The organic phase is washed with water and saturated sodium chloride solution, dried over magnesium sulfate, filtered and concentrated. The residue is dissolved in 150 ml of ethanol, 7.72 g (94.06 mmol) of sodium acetate trihydrate are added, and the resulting solution is heated under reflux for one hour. The reaction mixture is then added to ice, and the ethanol is stripped off.

The aqueous residue is extracted three times with ethyl acetate, and the combined organic phases are washed with 1 N sodium hydroxide solution, 1 N hydrochloric acid and subsequently with saturated sodium chloride solution, dried over magnesium sulfate, filtered and concentrated. Column chromatography on silica gel 60 (mobile phase: toluene→toluene/ethyl acetate 1:1) results in 5.52 g (56% of theory) of the product as beige-colored crystals.

LC-MS (Method 4): $R_t$=3.53 min.

MS (ESIpos): m/z=241 (M+H)$^+$ $^1$H-NMR (200 MHz, DMSO-d$_6$): δ=7.56-7.35 (m, 6 H), 6.91 (d, 1 H), 6.77 (dd, 1 H), 5.23 (s, 2 H), 4.77 (s, 2 H).

Example 59A

2-Bromo-6-benzyloxy-benzofuran-3(2H)-one

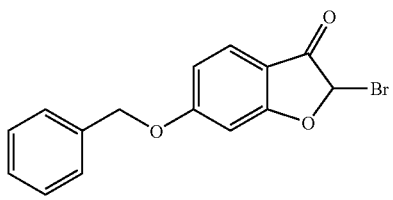

The title compound is prepared in analogy to the synthesis of Example 43A starting from Example 58A.

Yield: 40% of theory.

LC-MS (Method 12): $R_t$=4.12 min.

MS (ESIpos): m/z=319 (M+H)$^+$ $^1$H-NMR (200 MHz, DMSO-d$_6$): δ=7.54-7.37 (m, 5 H), 6.81-6.71 (m, 2 H), 5.56 (s, 1 H), 5.24 (s, 2 H).

Example 60A 3-tert-Butyldimethylsilyloxy-6-benzyloxy-2-(4-chlorophenyl)benzofuran

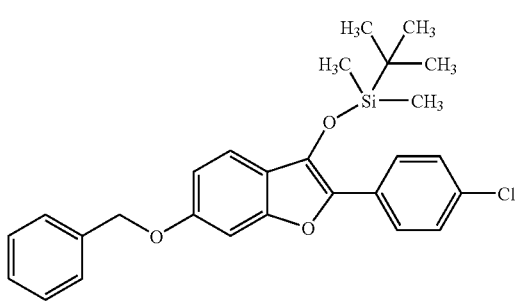

The title compound is prepared in analogy to the synthesis of Example 44A starting from Example 59A.

Yield: 77% of theory.

LC-MS (Method 4): $R_t$=5.20 min.

MS (ESIpos): m/z=465 (M+H)$^+$ $^1$H-NMR (300 MHz, DMSO-d$_6$): δ=7.85 (d, 2 H), 7.59-7.20 (m, 9 H), 7.04 (dd, 1 H), 5.22 (s, 2 H), 1.07 (s, 9 H), 0.17 (s, 3 H), 0.04 (s, 3 H).

Example 61A (S*,R*)-3-[6-Benzyloxy-2-(4-chlorophenyl)-3-oxo-2,3-dihydrobenzofuran-2-yl]-3-phenylpropanal

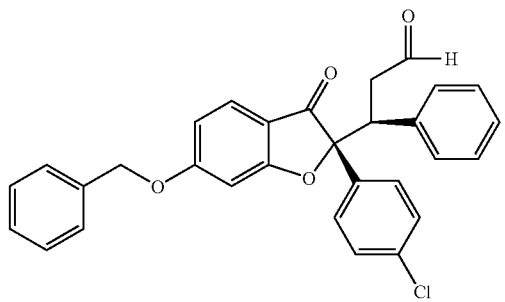

The title compound (as mixture of diastereomers) is prepared in analogy to the synthesis of Example 5A starting from Example 60A.

Example 62A 2-(2-Chloroethoxy)-6-hydroxyacetophenone

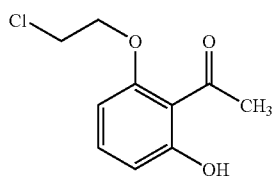

The title compound is prepared in analogy to the synthesis of Example 41A starting from 2,6-dihydroxyacetophenone.

Yield: 90% of theory.

LC-MS (Method 2): $R_t$=2.86 min.

MS (ESIpos): m/z=215 (M+H)$^+$ $^1$H-NMR (200 MHz, DMSO-d$_6$): δ=12.1 (s, 1 H), 7.34 (t, 1 H), 6.56 (dd, 1 H), 6.52 (dd, 1 H), 4.36-4.29 (m, 2 H), 4.05-3.97 (m, 2 H), 2.61 (s, 3 H).

Example 63A 4-(2-Chloroethoxy)-benzofuran-3-one

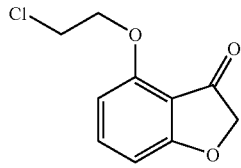

The title compound is prepared in analogy to the synthesis of Example 42A starting from Example 62A.

Yield: 69% of theory.

LC-MS (Method 2): $R_t$=2.42 min.

MS (ESIpos): m/z=213 (M+H)$^+$ $^1$H-NMR (200 MHz, DMSO-d$_6$): δ=7.61 (t, 1 H), 6.80 (d, 1 H), 6.67 (d, 1 H), 4.70 (s, 2 H), 4.43-4.35 (m, 2 H), 400-3.93 (m, 2 H).

Example 64A

2-Bromo-4-(2-chloroethoxy)-benzofuran-3(2H)-one

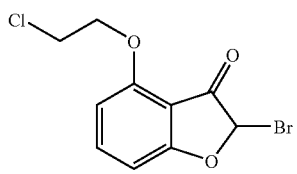

The title compound is prepared in analogy to the synthesis of Example 43A starting from Example 63A.

Yield: 86% of theory.

LC-MS (Method 4): $R_t$=2.90 min.

MS (ESIpos): m/z=291 (M+H)$^+$ $^1$H-NMR (300 MHz, DMSO-d$_6$): δ=7.62 (t, 1 H), 6.69 (d, 1 H), 6.65 (d, 1 H), 5.47 (s, 1 H), 4.42-4.37 (m, 2 H), 3.98-3.93 (m, 2 H).

Example 65A

2-Bromo-3-tert-butyldimethylsilyloxy-4-(2-chloroethoxy)benzofuran

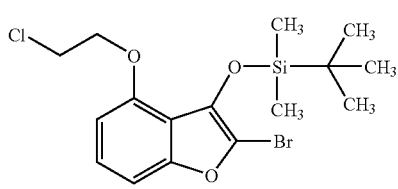

The title compound is prepared in analogy to the synthesis of Example 44A starting from Example 64A.

Yield: 46% of theory.

LC-MS (Method 9): $R_t$=2.14 min.

MS (ESIpos): m/z=292 [M+H—Si(CH$_3$)$_2$C(CH$_3$)$_3$]$^+$ $^1$H-NMR (300 MHz, DMSO-d$_6$): δ=7.22 (t, 1 H), 7.11 (dd, 1 H), 6.84 (dd, 1 H), 4.43-4.38 (m, 2 H), 3.99-3.94 (m, 2 H), 1.03 (s, 9 H), 0.26 (s, 6 H).

Example 66A 3-tert-Butyldimethylsilyloxy-4-(2-chloroethoxy)-2-(4-chlorophenyl)benzofuran

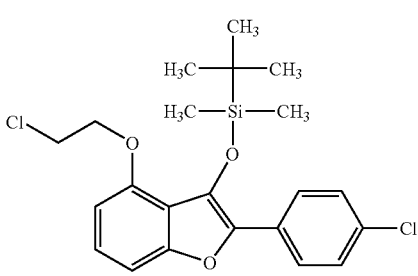

The title compound is prepared in analogy to the synthesis of Example 45A starting from Example 65A.

Yield: 75% of theory.

LC-MS (Method 4): $R_t$=3.29 min.

MS (ESIpos): m/z=437 (M+H)$^+$ $^1$H-NMR (400 MHz, DMSO-d$_6$): δ=7.82-7.77 (m, 2 H), 7.57-7.52 (m, 2 H), 7.26 (t, 1 H), 7.16 (d, 1 H), 6.83 (d, 1 H), 4.45-4.41 (m, 2 H), 4.02-3.98 (m, 2 H), 1.03 (s, 9 H), −0.02 (s, 6 H).

Example 67A 4-(2-Chloroethoxy)-2-(4-chlorophenyl)benzofuran-3-one

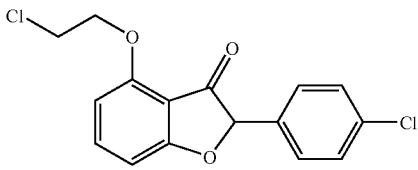

The title compound is prepared in analogy to the synthesis of Example 46A starting from Example 66A. The compound is employed in the next stage without further purification.

Example 68A (S*,R*)-3-[4-(2-Chloroethoxy)-2-(4-chlorophenyl)-3-oxo-2,3-dihydrobenzofuran-2-yl]-3-phenylpropanal

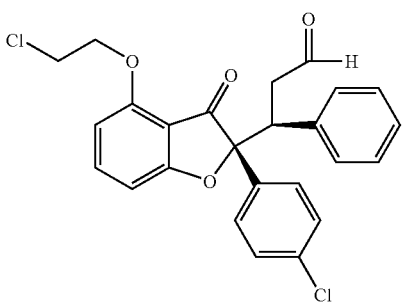

The title compound is prepared in analogy to the synthesis of Example 5A starting from Example 67A.

Yield: 28% of theory.

LC-MS (Method 9): $R_t$=2.68 min.

MS (ESIpos): m/z=455 (M+H)$^+$ $^1$H-NMR (300 MHz, DMSO-d$_6$): δ=9.33 (dd, 1 H), 7.70-7.65 (m, 2 H), 7.57 (t, 1 H), 7.55-7.49 (m, 2 H), 7.30-7.25 (m, 2 H), 7.17-7.06 (m, 3 H), 6.93 (d, 1 H), 6.51 (d, 1 H), 4.92 (dd, 1 H), 4.28-4.10 (m, 2 H), 3.83-3.77 (m, 2 H), 3.07 (ddd, 1 H), 2.53 (ddd, 1 H).

Example 69A (1S*,3S*,3aR*,8bS*)-8-(2-Chloroethoxy)-3a-(4-chlorophenyl)-3-phenyl-2,3,3a,8b-tetrahydrocyclopenta[b]benzofuran-1,8b-(1H)-diol

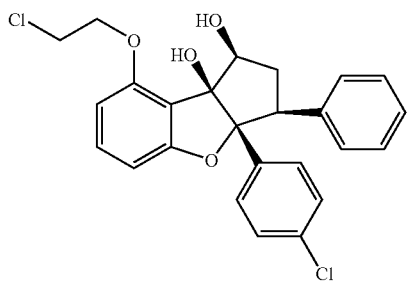

The title compound is prepared in analogy to the synthesis of Example 6A starting from Example 68A.

Yield: 55% of theory.

LC-MS (Method 2): $R_t$=3.47 min.

MS (ESIpos): m/z=457 (M+H)$^+$ $^1$H-NMR (300 MHz, DMSO-d$_6$): δ=7.28 (t, 1 H), 7.25-7.20 (m, 2 H), 7.20-7.15 (m, 2 H), 7.12-7.03 (m, 3 H), 6.91-6.86 (m, 2 H), 6.72 (d, 1 H), 6.64 (d, 1 H), 5.72 (d, 1 H), 4.91 (s, 1 H), 4.80 (ddd, 1 H), 4.36-4.31 (m, 2 H), 4.03-3.97 (m, 2 H), 3.30-3.24 (m, 1 H), 2.54-2.42 (m, 1 H), 2.19 (ddd, 1 H).

Example 70A (3S*,3aR*,8bR*)-8-(2-Chloroethoxy)-3a-(4-chlorophenyl)-8b-hydroxy-3-phenyl-2,3,3a,8b-tetrahydrocyclopenta[b]benzofuran-1-one

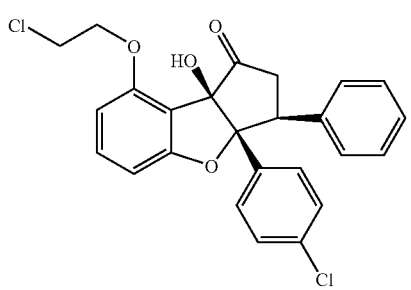

The title compound is prepared in analogy to the synthesis of Example 7A starting from Example 69A.

Yield: 63% of theory.

LC-MS (Method 9): $R_t$=2.70 min.

MS (ESIpos): m/z=455 (M+H)$^+$ $^1$H-NMR (400 MHz, DMSO-d$_6$): δ=7.40 (t, 1 H), 7.22-7.17 (m, 2 H), 7.14-7.05 (m, 3 H), 7.04-6.96 (m, 4 H), 6.87 (d, 1 H), 6.71 (d, 1 H), 6.03 (s, 1 H), 4.40-4.24 (m, 2 H), 3.93-3.86 (m, 2 H), 3.70 (dd, 1 H), 3.14 (dd, 1 H), 2.95 (dd, 1 H).

Example 71A (1R*,3S*,3aR*,8bS*)-8-(2-Chloroethoxy)-3a-(4-chlorophenyl)-3-phenyl-2,3,3a,8b-tetrahydrocyclopenta[b]benzofuran-1,8b-(1H)-diol

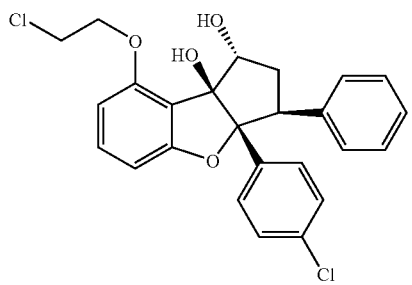

The title compound is prepared in analogy to the synthesis of Example 8A starting from Example 70A.

Yield: 70% of theory.

LC-MS (Method 8): $R_t$=3.67 min.

MS (ESIpos): m/z=457 (M+H)$^+$ $^1$H-NMR (200 MHz, DMSO-d$_6$): δ=7.24 (t, 1 H), 7.16-6.98 (m, 9 H), 6.68 (d, 1 H), 6.59 (d, 1 H), 5.11 (s, 1 H), 4.60-4.53 (m, 1 H), 4.50 (d, 1 H), 4.33-4.25 (m, 2 H), 4.03-3.90 (m, 3 H), 2.75 (dt, 1 H), 2.05 (dd, 1 H).

Example 72A

4-Hydroxybenzofuran-3-one

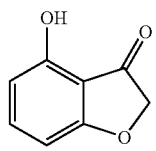

The title compound is prepared in analogy to the synthesis of Example 42A starting from 2,6-dihydroxyacetophenone.

Yield: 54% of theory.

LC-MS (Method 4): $R_t$=2.04 min.

MS (ESIpos): m/z=151 (M+H)$^+$ $^1$H-NMR (300 MHz, DMSO-$d_6$): δ=10.8 (s, 1 H), 7.43 (t, 1 H), 6.56 (dd, 1 H), 6.44 (dd, 1 H), 4.64 (s, 2 H).

Example 73A 4-(2-Methoxyethoxy)benzofuran-3-one

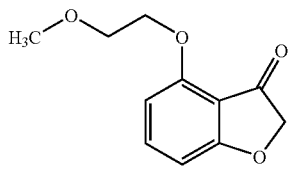

The title compound is prepared in analogy to the synthesis of Example 18A starting from Example 72A.
Yield: 68% of theory.
LC-MS (Method 4): $R_t$=2.23 min.
MS (ESIpos): m/z=209 (M+H)$^+$
$^1$H-NMR (300 MHz, DMSO-$d_6$): δ=7.59 (t, 1 H), 6.75 (d, 1 H), 6.65 (d, 1 H), 4.68 (s, 2 H), 4.25-4.20 (m, 2 H), 3.71-3.66 (m, 2 H), 3.34 (s, 3 H).

Example 74A

2-Bromo-4-(2-methoxyethoxy)benzofuran-3-one

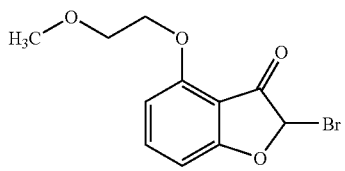

The title compound is prepared in analogy to the synthesis of Example 43A starting from Example 73A.
Yield: 84% of theory.
LC-MS (Method 4): $R_t$=2.63 min.
MS (ESIpos): m/z=287 (M+H)$^+$
$^1$H-NMR (300 MHz, DMSO-$d_6$): δ=8.24 (s, 2 H), 7.61 (t, 1 H), 6.65 (d, 1 H), 6.63 (d, 1 H), 5.45 (s, 1 H), 4.25-4.20 (m, 2 H), 3.71-3.65 (m, 2 H), 3.34 (s, 3 H).

Example 75A

2-Bromo-3-tert-butyldimethylsilyloxy-4-(2-methoxyethoxy)benzofuran

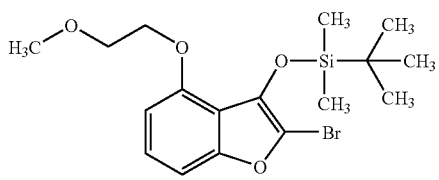

The title compound is prepared in analogy to the synthesis of Example 44A starting from Example 74A.
Yield: 99% of theory.
LC-MS (Method 14): $R_t$=2.43 min.
MS (ESIpos): m/z=401 (M+H)$^+$
$^1$H-NMR (300 MHz, DMSO-$d_6$): δ=7.21 (t, 1 H), 7.07 (dd, 1 H), 6.81 (dd, 1 H), 4.25-4.20 (m, 2 H), 3.72-3.66 (m, 2 H), 3.29 (s, 3 H), 1.02 (s, 9 H), 0.24 (s, 6 H).

Example 76A 3-tert-Butyldimethylsilyloxy-2-(4-chlorophenyl)-4-(2-methoxyethoxy)benzofuran

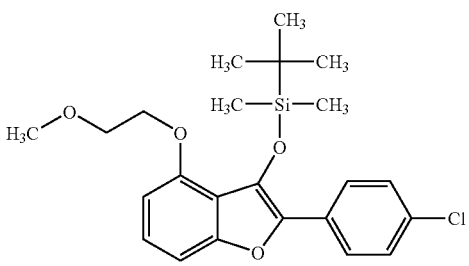

The title compound is prepared in analogy to the synthesis of Example 45A starting from Example 75A.
Yield: 68% of theory.
LC-MS (Method 9): $R_t$=3.58 min.
MS (ESIpos): m/z=433 (M+H)$^+$
$^1$H-NMR (300 MHz, DMSO-$d_6$): δ=7.85-7.79 (m, 2 H), 7.58-7.53 (m, 2 H), 7.26 (t, 1 H), 7.14 (dd, 1 H), 6.82 (dd, 1 H), 4.27-4.22 (m, 2 H), 3.75-3.70 (m, 2 H), 3.29 (s, 3 H), 1.02 (s, 9 H), −0.02 (s, 6 H).

Example 77A 2-(4-Chlorophenyl)-4-(2-methoxyethoxy)benzofuran-3-one

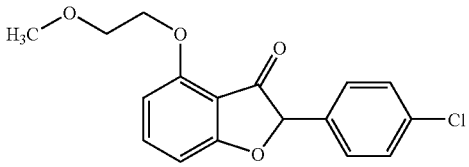

The title compound is prepared in analogy to the synthesis of Example 46A starting from Example 76A. The compound is employed in the next stage without further purification.

Example 78A (S*,R*)-3-[2-(4-Chlorophenyl)-4-(2-methoxyethoxy)-3-oxo-2,3-dihydrobenzofuran-2-yl]-3-phenylpropanal

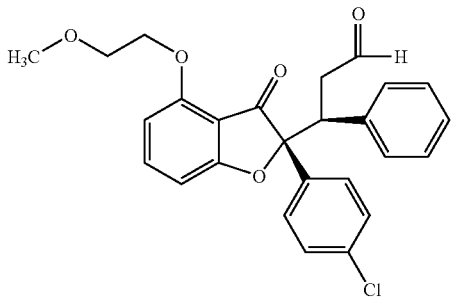

The title compound is prepared in analogy to the synthesis of Example 5A starting from Example 77A.
Yield: 8% of theory.
LC-MS (Method 9): $R_t$=2.58 min.
MS (ESIpos): m/z=451 (M+H)$^+$.

Example 79A (1S*,3S*,3aR*,8bS*)-6-(3-Chloropropoxy)-3a-(4-chlorophenyl)-3-phenyl-2,3,3a,8b-tetrahydrocyclopenta[b]benzofuran-1,8b-(1H)-diol

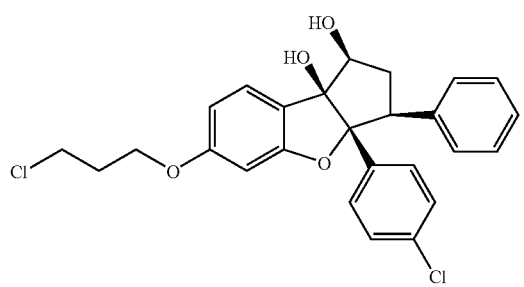

The title compound is prepared in analogy to the synthesis of Examples 41A-48A starting from 2,4-dihydroxyacetophenone and 3-chloropropanol.
LC-MS (Method 13): $R_t$=3.02 min.
MS (ESIneg): m/z=469 (M−H)$^−$
$^1$H-NMR (300 MHz, DMSO-d$_6$): δ=7.32-7.01 (m, 8 H), 6.94-6.92 (m, 2 H), 6.69 (d, 1 H), 6.60 (dd, 1 H), 5.81 (d, 1 H), 5.01 (s, 1 H), 4.48-4.42 (m, 1 H), 4.13 (t, 2 H), 3.80 (t, 2 H), 3.35-3.27 (m, 1 H), 2.47-2.41 (m, 1 H), 2.30-2.14 (m, 3 H).

Example 80A

N-(3-Oxo-2,3-dihydro-1-benzofuran-6-yl)acetamide

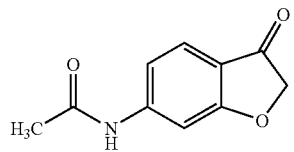

32.6 g (0.181 mol) of chloroacetyl chloride are added, followed within 15 minutes by 20 g (0.121 mol) of N-(3-methoxyphenyl)acetamide, to a solution of 64.6 g (0.484 mol) of aluminum chloride in 100 ml of 1,2-dichloroethane at 0° C. under argon. The temperature rises to 10° C. during this. The mixture is then slowly warmed to room temperature and stirred overnight. The brown mixture is added to ice-water, and ethyl acetate is added. After vigorous stirring, N-(3-methoxy-4-chloroacetylphenyl)acetamide precipitates and is filtered off with suction and dried under higher vacuum. The resulting solid is introduced into 140 ml of ethanol and, after addition of 13.2 g (0.154 mol) of sodium acetate, heated under reflux overnight. Cooling is followed by addition of water, and the ethanol is stripped off in a rotary evaporator. The precipitated solid is filtered off with suction on a frit and dried. 9.35 g (40% of theory) of the product result as a solid with a pale reddish color.

$^1$H-NMR (200 MHz, DMSO-d$_6$): δ=10.5 (s, 1 H), 7.7 (s, 1 H), 7.6 (s, 1 H), 7.1 (s, 1 H), 4.8 (s, 2 H),3.3 (s, 3 H).

Example 81A

6-Amino-1-benzofuran-3(2H)-one

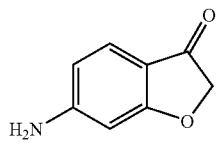

5 ml of 1 N hydrochloric acid are added to a solution of 500 mg (2.62 mmol) of N-(3-oxo-2,3-dihydro-1-benzofuran-6-yl)acetamide in 5 ml of methanol, and the mixture is heated under reflux for one hour. After cooling, the mixture is added to a mixture of ice-water, saturated sodium bicarbonate solution and ethyl acetate. The organic phase is separated off, washed with water and saturated sodium chloride solution, dried over magnesium sulfate, filtered and concentrated. 318 mg (61% of theory) of the target compound result as brown powder with a purity of 75%.
LC-MS (Method 4): $R_t$=1.71 min.
MS (ESIpos): m/z=150 (M+H)$^+$
$^1$H-NMR (300 MHz, DMSO-d$_6$): δ=7.24 (s, 1 H), 6.51 (br. s, 2 H), 6.32 (dd, 1 H), 6.12 (d, 1 H), 4.75 (s, 2 H).

Example 82A

Benzyl(3-oxo-2,3-dihydro-1-benzofuran-6-yl)carbamate

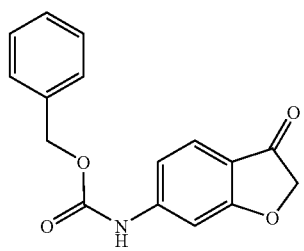

54.7 ml (314 mmol) of diisopropylethylamine and 28.3 ml (188 mmol) of benzyl chloroformate are added to a solution of 23.42 g (157 mmol) of 6-amino-1-benzofuran-3(2H)-one in 400 ml of THF at 0° C. and the mixture is stirred at room temperature for 3 hours. Then a further 4.7 ml (31 mmol) of benzyl chloroformate are added, and the mixture is stirred overnight. The mixture is added to ice-water and extracted twice with ethyl acetate. The combined organic phases are washed with water and saturated sodium chloride solution, dried over magnesium sulfate, filtered and concentrated. Chromatography on silica gel 60 (mobile phase: dichloromethane→dichloromethane/ethyl acetate 5:1) affords 30.80 g (64% of theory) of the product as colorless crystals.
LC-MS (Method 4): $R_t$=3.43 min.
MS (ESIpos): m/z=284 (M+H)$^+$ ¹H-NMR (300 MHz, DMSO-d₆): δ=10.38 (s, 1 H), 7.56-7.31 (m, 7 H), 7.12 (dd, 1 H), 5.20 (s, 2 H), 4.74 (s, 1 H).

Example 83A

Benzyl[(1S*,3S*,3aR*,8bS*)-3a-(4-chlorophenyl)-1,8b-dihydroxy-3-phenyl-2,3,3a,8b-tetrahydro-1H-benzo[b]cyclopenta[d]furan-6-yl]carbamate

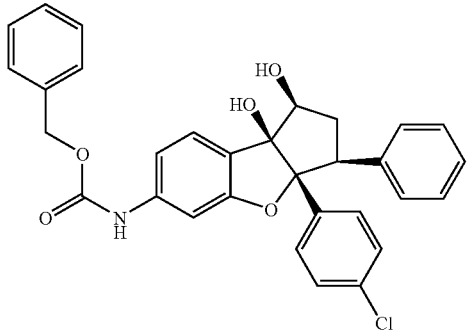

The title compound is prepared in analogy to the synthesis of Examples 43A (method a), 44A, 45A, 46A, 5A and 6A starting from Example 82A.
LC-MS (Method 7): $R_t$=2.90 min.
MS (ESIneg): m/z=526 (M−H)⁻
¹H-NMR (400 MHz, DMSO-d₆): δ=9.88 (s, 1 H), 7.46-6.91 (m, 17 H), 5.87 (d, 1 H), 5.18 (m, 2 H), 5.07 (s, 1 H), 4.45-4.44 (m, 1 H), 3.35-3.28 (m, 1 H), 2.48-2.43 (m, 1 H), 2.25-2.20 (m, 1 H).

Example 84A (1S*,3S*,3aR*,8bS*)-6-Amino-3a-(4-chlorophenyl)-3-phenyl-1,2,3,3a-tetrahydrocyclopena[b]-benzofuran-1,8b-(1H)-diol

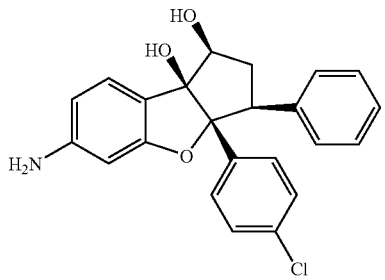

1 g of 10% palladium on activated carbon is added to a solution of 8.18 g (15.5 mmol) of benzyl [(1S*,3S*,3aR*,8bS*)-3a-(4-chlorophenyl)-1,8b-dihydroxy-3-phenyl-2,3,3a,8b-tetrahydro-1H-benzo[b]cyclopenta[d]furan-6-yl]carbamate in 100 ml of methanol, and the mixture is hydrogenated under 2 bar for 2 hours. After removal of the catalyst, the residue is concentrated to result in 6.06 g (92% of theory) of the title compound, which contains about 7% of the corresponding dehalogenated compound as impurity.
LC-MS (Method 13): $R_t$=2.34 min.
MS (ESIpos): m/z=394 (M+H)⁺

¹H-NMR (300 MHz, DMSO-d₆): δ=7.22-6.87 (m, 10 H), 6.24-6.21 (m, 2 H), 5.73 (d, 1 H), 5.19 (s, 2 H), 4.78 (s, 1 H), 4.44-4.37 (m, 1 H), 3.35-3.24 (m, 1 H), 2.48-2.40 (m, 1 H), 2.27-2.11 (m, 1 H).

Example 85A

Bromo-(4-chlorophenyl)acetic acid

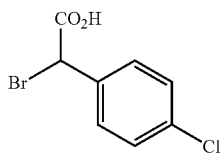

80.0 g (469 mmol) of 4-chlorophenylacetic acid are dissolved in 200 ml of tetrachloroethane under argon and heated under RF. While boiling, 100 g (563 mmol) of N-bromosuccinimide and 7.70 g (46.9 mmol) of 2,2'-azobis-2-methylpropanenitrile are added, and the mixture is heated under RF overnight. It is then cooled to 0° C. and filtered with suction, the precipitate is washed with cold tetrachloromethane, and the filtrate is concentrated. The residue is dissolved in diethyl ether and extracted three times with saturated aqueous bicarbonate solution. The combined aqueous phases are adjusted to a pH of 1 with concentrated hydrochloric acid and extracted four times with diethyl ether. The combined organic phases are dried over magnesium sulfate, filtered and concentrated to result in 83.0 g (71% of theory) of the product, which is reacted further without further purification.
LC-MS (Method 11): $R_t$=3.42 min.
MS (ESIneg): m/z=249 (M−H)⁻
¹H-NMR (300 MHz, DMSO-d₆): δ=13.5 (s, 1 H), 7.61-7.55 (m, 2 H), 7.49-7.43 (m, 2 H), 5.80 (s, 1 H).

Example 86A (4-Chlorophenyl)-(3,5-dipropoxyphenoxy)acetic acid

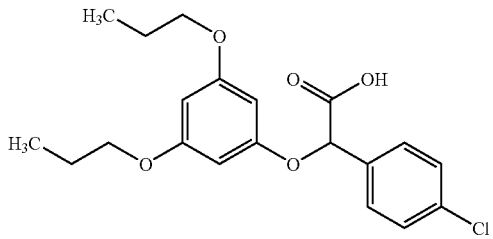

4.37 g (109 mmol) of sodium hydride as 60% dispersion in mineral oil are added in portions to a solution of 10.0 g (47.6 mmol) of 3,5-dipropoxyphenol and 11.9 g (47.6 mmol) of bromo-(4-chlorophenyl)acetic acid in 150 ml of THF under argon. The mixture is stirred at RT for 0.5 h and heated under RF overnight. Water is then added while cooling in ice, the mixture is extracted three times with chloroform, and the combined organic phases are washed with 1 N sodium hydroxide solution and saturated aqueous sodium chloride solution, dried over magnesium sulfate, filtered and concentrated (residue 1). The combined aqueous phases are adjusted to a pH of 1 with concentrated hydrochloric acid and extracted three times with diethyl ether. The combined organic phases are washed with saturated aqueous sodium chloride solution, dried over magnesium sulfate, filtered and concentrated (residue 2). Chromatography of combined residues 1 and 2 on silica gel 60 (1st mobile phase: toluene/ethyl acetate 9:1 to remove unreacted 3,5-dipropoxyphenol, 2nd mobile phase: dichloromethane/methanol 9:1) results in 12.1 g (67% of theory) of the product.

LC-MS (Method 1): $R_t$=4.21 min.
MS (ESIpos): m/z=379 (M+H)$^+$
$^1$H-NMR (400 MHz, DMSO-d$_6$): δ=7.54 (d, 2 H), 7.38 (d, 2 H), 6.09-6.01 (m, 3 H), 5.41 (s, 1 H), 3.84 (t, 4 H), 1.67 (sext, 4 H), 0.94 (t, 6 H).

Example 87A 2-(4-Chlorophenyl)-4,6-dipropoxybenzofuran-3(2H)-one

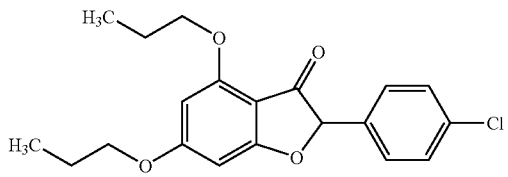

The title compound is prepared in analogy to the synthesis of Example 4A starting from Example 86A.
Yield: 44% of theory.
LC-MS (Method 12): $R_t$=4.75 min.
MS (ESIpos): m/z=361 (M+H)$^+$
$^1$H-NMR (300 MHz, DMSO-d$_6$): δ=7.50-7.44 (m, 2 H), 7.35-7.30 (m, 2 H), 6.46 (d, 1 H), 6.21 (d, 1 H), 5.74 (s, 1 H), 4.11-3.98 (m, 4 H), 1.82-1.64 (m, 4 H), 0.99 (t, 3 H), 0.96 (t, 3 H).

Example 88A (S*,R*)-3-[2-(4-Chlorophenyl)-4,6-dipropoxy-3-oxo-2,3-dihydrobenzofuran-2-yl]-3-phenylpropanal

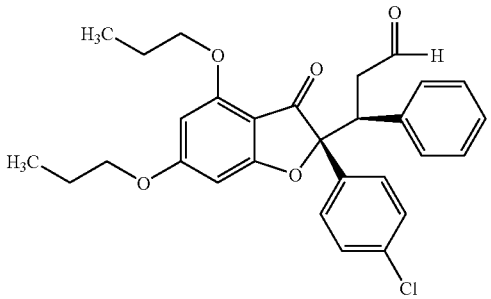

The title compound is prepared in analogy to the synthesis of Example 5A starting from Example 87A.
Yield: 49% of theory.
LC-MS (Method 12): $R_t$=4.93 min.
MS (ESIpos): m/z=493 (M+H)$^+$
$^1$H-NMR (200 MHz, DMSO-d$_6$): δ=9.32 (d, 1 H), 7.69-7.61 (m, 2 H), 7.55-7.47 (m, 2 H), 7.31-7.09 (m, 5 H), 6.47 (d, 1 H), 5.98 (d, 1 H), 4.24 (dd, 1 H), 4.02 (t, 2 H), 3.90-3.74 (m, 2 H), 3.02 (ddd, 1 H), 2.57-2.43 (m, 1 H), 1.73 (sext, 2 H), 1.57 (sext, 2 H), 0.97 (t, 3 H), 0.84 (t, 3 H).

Exemplary Embodiments

Example 1

(3S*,3aR*,8bR*)-3a-(4-Bromophenyl)-6,8-diethoxy-8b-hydroxy-3-phenyl-2,3,3a,8b-tetrahydrocyclopenta[b]benzofuran-1-oxime

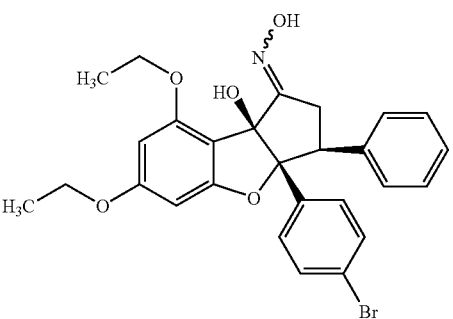

The title compound is prepared in analogy to the synthesis of Example 14 starting from Example 7A.
Yield: 51% of theory.
LC-MS (Method 4): $R_t$=3.66 min.
MS (ESIneg): m/z=522 (M–H)$^-$
$^1$H-NMR (300 MHz, DMSO-d$_6$): δ=11.0 (s, 1 H), 7.36-7.30 (m, 2 H), 7.14-7.05 (m, 3 H), 7.00-6.94 (m, 4 H), 6.35 (d, 1 H), 6.14 (d, 1 H), 5.25 (s, 1 H), 4.11-3.95 (m, 4 H), 3.52 (t, 1 H), 3.02-2.93 (m, 2 H).

Example 2

(1R*,3S*,3aR*,8bS*)-3a-(3'-Aminobiphenyl-4-yl)-6,8-diethoxy-3-phenyl-2,3,3a,8b-tetrahydrocyclopenta[b]benzofuran-1,8b-(1H)-diol

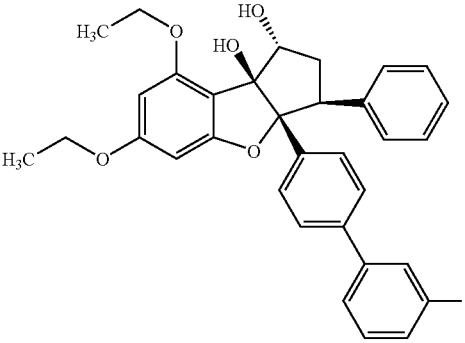

51.1 mg (0.10 mmol) of (1R*,3S*,3aR*,8bS*)-3a-(4-bromophenyl)-6,8-diethoxy-3-phenyl-2,3,3a,8b-tetrahydrocyclopenta[b]benzofuran-1,8b-(1H)-diol (Example 8A), 15.5 mg (0.10 mmol) of 3-aminophenyl boronic acid, 10.6 mg (0.10 mmol) of sodium carbonate and 5.8 mg (0.005 mmol) of tetrakis(triphenylphosphine)palladium(0) are heated in a mixture of 0.1 ml of water and 0.5 ml of dioxane at 80° C. under argon overnight. The mixture is then diluted with DMSO and filtered, and the filtrate is purified by preparative HPLC. 17.4 mg (25% of theory) of the product are obtained.

LC-MS (Method 10): $R_t$=2.07 min.
MS (ESIpos): m/z=524 (M+H)$^+$.

Example 3

(1R*,3S*,3aR*,8bS*)-6,8-Diethoxy-3-phenyl-2,3,3a,8b-tetrahydro-3a-(4-thiophen-3-ylphenyl)-cyclopenta[b]benzofuran-1,8b-(1H)-diol

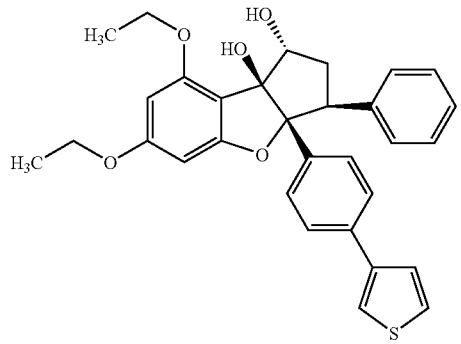

The title compound is prepared in analogy to the synthesis of Example 2.

LC-MS (Method 10): $R_t$=2.41 min.
MS (ESIpos): m/z=515 (M+H)$^+$.

Example 4

(1R*,3S*,3aR*,8bS*)-3a-(3'-Cyanobiphenyl-4-yl)-6,8-diethoxy-3-phenyl-2,3,3a,8b-tetrahydrocyclopenta[b]benzofuran-1,8b-(1H)-diol

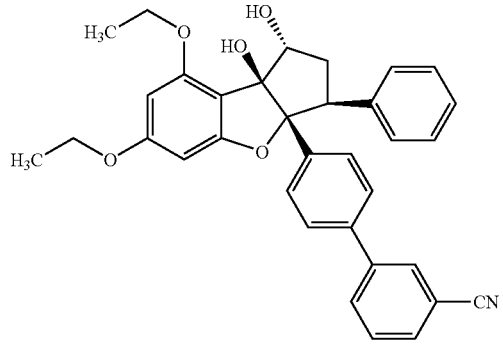

The title compound is prepared in analogy to the synthesis of Example 2.

LC-MS (Method 10): $R_t$=2.38 min.
MS (ESIpos): m/z=534 (M+H)$^+$.

Example 5

(1R*,3S*,3aR*,8bS*)-6,8-Diethoxy-3a-[4-(1H-indol-5-yl)-phenyl]-3-phenyl-2,3,3a,8b-tetrahydrocyclopenta[b]benzofuran-1,8b-(1H)-diol

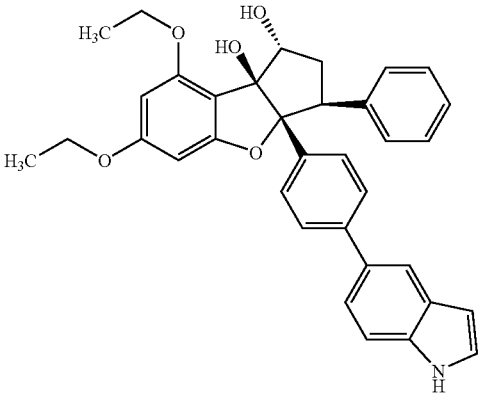

The title compound is prepared in analogy to the synthesis of Example 2.

LC-MS (Method 10): $R_t$=2.31 min.
MS (ESIpos): m/z=548 (M+H)$^+$.

Example 6

(1R*,3S*,3aR*,8bS*)-6,8-Diethoxy-3a-(3'-ethylsulfonylbiphenyl-4-yl)-3-phenyl-2,3,3a,8b-tetrahydrocyclopenta[b]benzofuran-1,8b-(1H)-diol

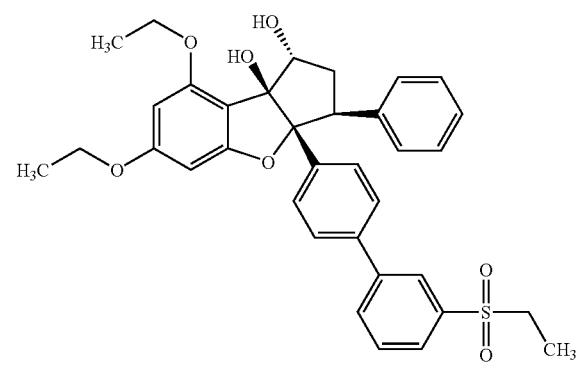

The title compound is prepared in analogy to the synthesis of Example 2.

LC-MS (Method 10): $R_t$=2.26 min.
MS (ESIpos): m/z=601 (M+H)$^+$.

Example 7

(1R*,3S*,3aR*,8bS*)-3a-(5'-Amino-2'-fluorobiphenyl-4-yl)-6,8-diethoxy-3-phenyl-2,3,3a,8b-tetrahydrocyclopenta[b]benzofuran-1,8b-(1H)-diol

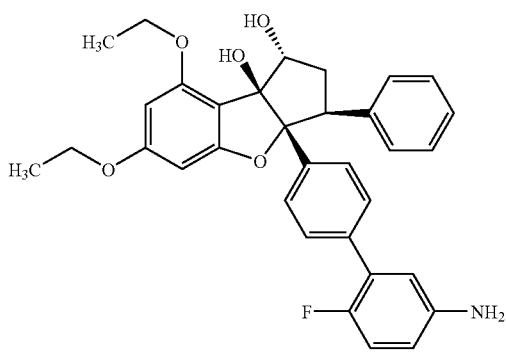

The title compound is prepared in analogy to the synthesis of Example 2.

LC-MS (Method 10): $R_t$=2.05 min.

MS (ESIpos): m/z=542 (M+H)$^+$.

Example 8

(1R*,3S*,3aR*,8bS*)-3a-(4-Quinoxalin-6-ylphenyl)-6,8-diethoxy-3-phenyl-2,3,3a,8b-tetrahydrocyclopenta[b]benzofuran-1,8b-(1H)-diol

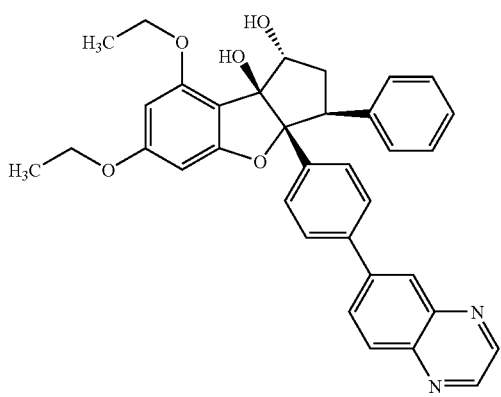

The title compound is prepared in analogy to the synthesis of Example 2.

LC-MS (Method 10): $R_t$=2.29 min.

MS (ESIpos): m/z=561 (M+H)$^+$.

Example 9

(1R*,3S*,3aR*,8bS*)-6,8-Diethoxy-3-phenyl-3a-(4-pyrrolidin-1-ylphenyl)-2,3,3a,8b-tetrahydrocyclopenta[b]benzofuran-1,8b-(1H)-diol

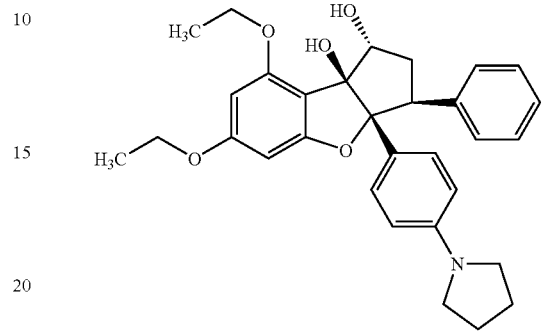

51.1 mg (0.10 mmol) of (1R*,3S*,3aR*,8bS*)-3a-(4-bromophenyl)-6,8-diethoxy-3-phenyl-2,3,3a,8b-tetrahydrocyclopenta[b]benzofuran-1,8b-(1H)-diol (Example 8A), 4.7 mg (0.07 mmol) of pyrrolidine, 7.1 mg (0.07 mmol) of sodium tert-butoxide, 1.2 mg (0.001 mmol) of tris(dibenzylideneacetone)dipalladium(0) and 1.7 mg (0.003 mmol) of rac-2,2'-bis(diphenylphosphino)-1,1'-binaphthyl are heated in 0.6 ml of toluene at 80° C. under argon overnight. The mixture is then concentrated, taken up in DMSO and filtered, and the filtrate is purified by preparative HPLC. 14.5 mg (43% of theory) of the product are obtained.

LC-MS (Method 10): $R_t$=2.38 min.

MS (ESIpos): m/z=502 (M+H)$^+$.

Example 10

(1R*,3S*,3aR*,8bS*)-3a-[4-(Benzyl-methylamino)phenyl]-6,8-diethoxy-3-phenyl-2,3,3a,8b-tetrahydrocyclopenta[b]benzofuran-1,8b-(1H)-diol

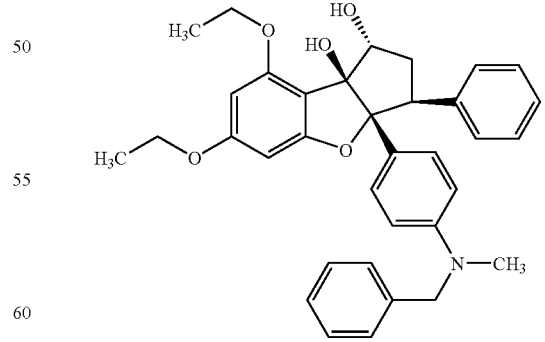

The title compound is prepared in analogy to the synthesis of Example 9.

LC-MS (Method 10): $R_t$=2.44 min.

MS (ESIpos): m/z=552 (M+H)$^+$.

Example 11

(1R*,3S*,3aR*,8bS*)-6,8-Diethoxy-3a-[4-(methyl-pyridin-4-ylmethylamino)phenyl]-3-phenyl-2,3,3a,8b-tetrahydrocyclopenta[b]benzofuran-1,8b-(1H)-diol

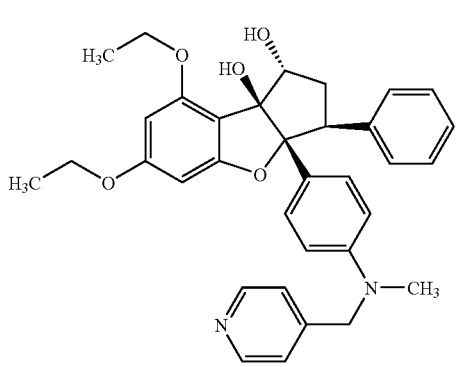

The title compound is prepared in analogy to the synthesis of Example 9.

LC-MS (Method 10): $R_t$=1.73 min.
MS (ESIpos): m/z=553 (M+H)⁺.

Example 12

(2R*,3S*,3aR*,8bR*)-3a-(4-Bromophenyl)-6,8-diethoxy-2-dimethylcarbamid-8b-hydroxy-3-phenyl-2,3,3a,8b-tetrahydrocyclopenta[b]benzofuran-1-one

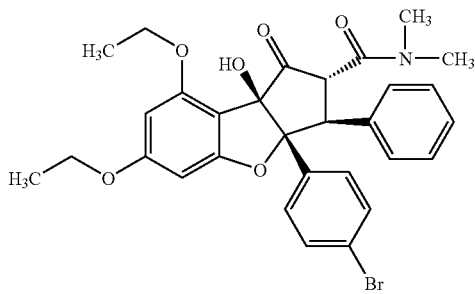

The title compound is prepared in analogy to the synthesis of Example 16 starting from Example 9A.

Yield: 29% of theory.
LC-MS (Method 4): $R_t$=3.53 min.
MS (ESIpos): m/z=581 (M+H)⁺
¹H-NMR (200 MHz, DMSO-d₆): δ=7.37-7.29 (m, 2 H), 7.15-6.90 (m, 7 H), 6.43 (d, 1 H), 6.16 (d, 1 H), 6.00 (s, 1 H), 4.64 (d, 1 H), 4.28 (d, 1 H), 4.15-3.91 (m, 4 H), 3.30 (s, 3 H), 2.77 (s, 3 H), 1.35 (t, 3 H), 1.22 (t, 3 H).

Example 13

(1R*,2R*,3S*,3aR*,8bS*)-3a-(4-Bromophenyl)-6,8-diethoxy-2-dimethylcarbamid-3-phenyl-2,3,3a,8b-tetrahydrocyclopenta[b]benzofuran-1,8b-(1H)-diol

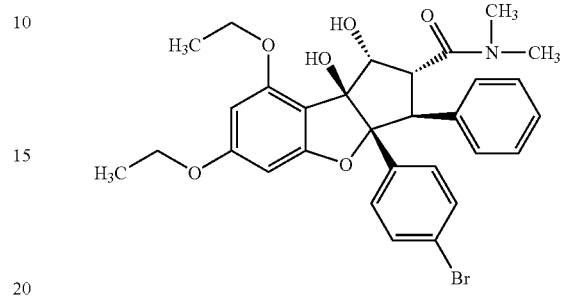

The title compound is prepared in analogy to the synthesis of Example 17 starting from Example 12.

Yield: 80% of theory.
LC-MS (Method 5): $R_t$=3.61 min.
MS (ESIpos): m/z=583 (M+H)⁺
¹H-NMR (200 MHz, DMSO-d₆): δ=7.27-7.19 (m, 2 H), 7.12-6.95 (m, 5 H), 6.88-6.80 (m, 2 H), 6.29 (d, 1 H), 6.12 (d, 1 H), 5.20 (s, 1 H), 4.84-4.76 (m, 1 H), 4.60 (d, 1 H), 4.29 (d, 1 H), 4.13-3.97 (m, 5 H), 3.26 (s, 3 H), 2.75 (s, 3 H), 1.34 (t, 3 H), 1.31 (t, 3 H).

Example 14

(3S*,3aR*,8bS*)-3a-(4-Chlorophenyl)-6,8-diethoxy-8b-hydroxy-3-phenyl-2,3,3a,8b-tetrahydrocyclopenta[b]benzofuran-1-oxime

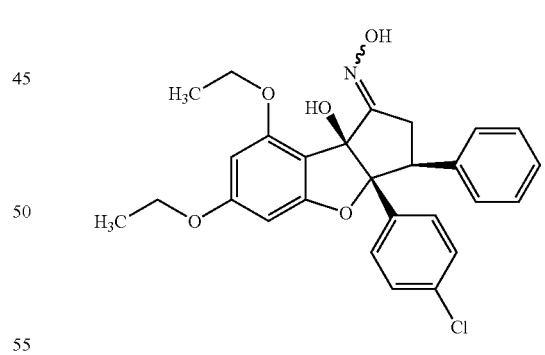

Firstly 20 ml of pyridine and then 90 mg (1.30 mmol) of hydroxylammonium chloride are added to 500 mg (1.08 mmol) of (3S*,3aR*,8bR*)-3a-(4-chlorophenyl)-6,8-diethoxy-8b-hydroxy-3-phenyl-2,3,3a,8b-tetrahydrocyclopenta[b]benzofuran-1-one (Example 15A) dissolved in 20 ml of ethanol at room temperature, and the solution is stirred for one day. After the volatile constituents have been stripped off in a rotary evaporator, the residue is dissolved in ethyl acetate. The organic phase is then washed with 1 N hydrochloric acid, saturated sodium bicarbonate solution and saturated sodium chloride solution, dried over magnesium sulfate, filtered and concentrated. 515 mg (100% of theory) of the racemic product result as colorless crystals.

LC-MS (Method 9): $R_t$=2.66 min.

MS (ESIneg): m/z=478 (M−H)⁻

$^1$H-NMR (300 MHz, DMSO-$d_6$): δ=11.01 (s, 1 H), 7.21-6.94 (m, 9 H), 6.35 (d, 1 H), 6.14 (d, 1 H), 5.25 (s, 1 H), 4.10-3.99 (m, 4 H), 3.55-3.49 (m, 1 H), 3.00-2.94 (m, 2 H), 1.36-1.30 (m, 6 H).

Example 15

(1R*,3S*,3aR*,8bS*)-1-Amino-3a-(4-chlorophenyl)-6,8-diethoxy-8b-hydroxy-3-phenyl-2,3,3a,8b-tetrahydrocyclopenta[b]benzofuran

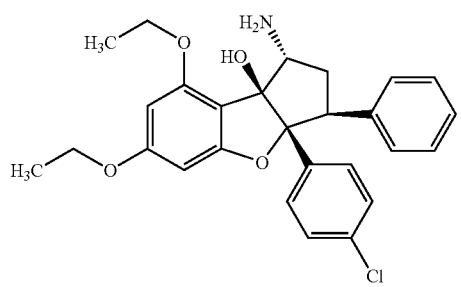

At 0° C., 115 mg (1.07 mmol) of (3S*,3aR*,8bR*)-3a-(4-chlorophenyl)-6,8-diethoxy-8b-hydroxy-3-phenyl-2,3,3a,8b-tetrahydrocyclopenta[b]benzofuran-1-oxime (Example 14) are added in portions to a stirred solution of 3.22 ml (3.22 mmol) of a 1 N solution of lithium aluminum hydride in diethyl ether in an additional 6 ml of diethyl ether. After gas evolution has ceased, the mixture is heated to reflux for 30 minutes. It is then diluted with ethyl acetate at 0° C., and 1 N sodium hydroxide solution is added dropwise. The mixture is stirred for 5 minutes and then the phases are separated. The aqueous phase is extracted twice with ethyl acetate. The combined organic phases are washed with saturated sodium chloride solution, dried over magnesium sulfate, filtered and concentrated. The residue crystallizes from a mixture of dichloromethane, diethyl ether and petroleum ether. The resulting crystals are filtered off with suction through a glass frit and dried. 155 mg (31% of theory) of the racemic product result as colorless crystals.

LC-MS (Method 8): $R_t$=2.62 min.

MS (ESIneg): m/z=464 (M−H)⁻

$^1$H-NMR (400 MHz, DMSO-$d_6$): δ=7.13-7.03 (m, 7 H), 6.91 (d, 2 H), 6.24 (d, 1 H), 6.11 (d, 1H), 4.06-4.00 (m, 4 H), 3.75 (dd, 1 H), 3.34 (dd, 1 H), 2.41-2.35 (m, 1 H), 2.15-2.05 (m, 1 H), 1.35-1.31 (m, 1 H).

Preparative separation of the racemate into the enantiomers is carried out by HPLC on a chiral phase by Method 29A.

Analytical data (Method 29B):

Enantiomer A: $R_t$=3.89 min., enantiomer B: $R_t$=6.09 min.

Example 16

(2R*,3S*,3aR*,8bR*)-3a-(4-Chlorophenyl)-6,8-diethoxy-2-diethylcarbamid-8-hydroxy-3-phenyl-2,3,3a,8b-tetrahydrocyclopenta[b]benzofuran-1-one

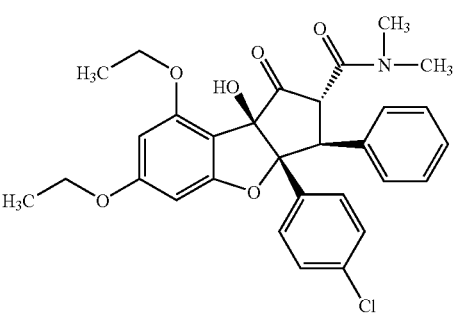

674 mg (1.30 mmol) of benzotriazol-1-yloxytripyrrolidinophosphonium hexafluorophosphate, 106 mg (1.30 mmol) of dimethylamine hydrochloride and 0.47 ml (2.70 mmol) of N,N-diisopropylethylamine are added to a solution of 550 mg (1.08 mmol) of (2R*,3S*,3aR*,8bR*)-3a-(4-chlorophenyl)-6,8-diethoxy-8-hydroxy-3-phenyl-2,3,3a,8b-tetrahydrocyclopenta[b]benzofuran-2-carboxylic acid (Example 17A) in THF at 0° C., and the mixture is then stirred at 0° C. for 4 h. The reaction mixture is then poured into a mixture of 50 ml of saturated ammonium chloride solution, ice-water and ethyl acetate. After removal of the organic phase, the aqueous phase is extracted twice with ethyl acetate. The combined organic phases are washed with water, saturated sodium bicarbonate solution and saturated sodium chloride solution, dried over magnesium sulfate, filtered and concentrated. The residue is purified on silica gel 60 (mobile phase: toluene/ethyl acetate 10:1, 6:1, 4:1). 159 mg (27% of theory) of racemic product result as colorless foam.

LC-MS (Method 2): $R_t$=3.41 min.

MS (ESIpos): m/z=536 (M+H)⁺

$^1$H-NMR (400 MHz, DMSO-$d_6$): δ=7.25-6.94 (m, 9 H), 6.43 (d, 1 H), 6.16 (d, 1 H), 6.00 (s, 1 H), 4.63 (d, 1 H), 4.29 (d, 1 H), 4.13-3.94 (m, 4 H), 3.30 (s, 3 H), 2.77 (s, 3 H), 1.35 (t, 3 H), 1.22 (t, 3 H).

Example 17

(1R*,2R*,3S*,3aR*,8bS*)-3a-(4-Chlorophenyl)-6,8-diethoxy-2-dimethylcarbamid-3-phenyl-2,3,3a,8b-tetrahydrocyclopenta[b]benzofuran-1,8b-(1H)-diol

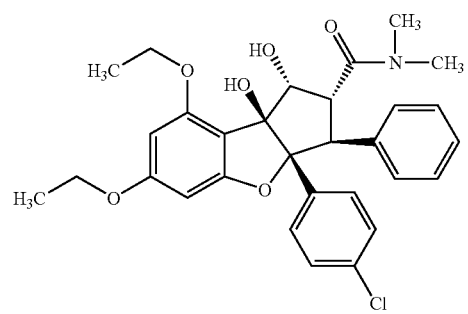

A solution of 1104 mg (4.20 mmol) of tetramethylammonium triacetoxyborohydride in 1.5 ml of acetonitrile and 1.5 ml of glacial acetic acid is stirred at room temperature for 30 minutes. 150 mg (0.28 mmol) of (2R*,3S*,3aR*,8bR*)-3a-(4-chlorophenyl)-6,8-diethoxy-2-dimethylcarbamid-8-hydroxy-3-phenyl-2,3,3a,8b-tetrahydrocyclopenta[b]benzofuran-1-one are added as solution in 13.5 ml of acetonitrile and stirred at room temperature for two hours. At 0° C., saturated sodium bicarbonate solution is added, and the mixture is extracted three times with ethyl acetate. The combined organic phases are dried over magnesium sulfate, filtered and concentrated. The crystals which separate out of diethyl ether are filtered off with suction, washed with diethyl ether/petroleum ether 1:1 and dried. 94 mg (62% of theory) of the product result as racemic mixture.

LC-MS (Method 8): $R_t$=3.23 min.

MS (ESIpos): m/z=538 (M+H)$^+$ $^1$H-NMR (300 MHz, DMSO-d$_6$): δ=7.15-6.94 (m, 7 H), 6.85-6.82 (m, 2 H), 6.29 (d, 1 H), 6.12 (d, 1 H), 5.16 (s, 1 H), 4.82-4.79 (m, 1 H), 4.56 (d, 1 H), 4.29 (d, 1 H), 4.08-3.99 (m, 4 H), 3.25 (s, 3 H), 2.76 (s, 1 H), 1.36-1.29 (m, 6 H).

Preparative separation of the racemate into the enantiomers is carried out by HPLC on a chiral phase by Method 26A.

Analytical data (Method 26B):

Enantiomer A: $R_t$=3.96 min., enantiomer B: $R_t$=15.29 min.

Example 18

(1R*,3S*,3aR*,8bS*)-6,8-Bis(2-methoxyethoxy)-3a-(4-bromophenyl)-3-phenyl-2,3,3a,8b-tetrahydrocyclopenta[b]benzofuran-1,8b-(1H)-diol

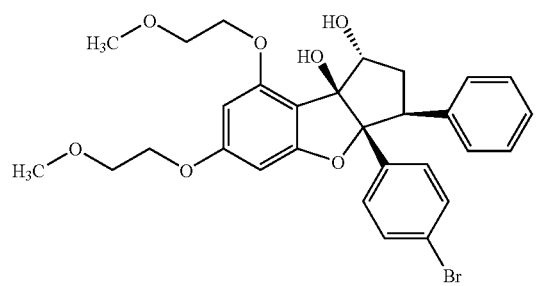

The title compound is prepared in analogy to the synthesis of Example 6A starting from Example 22A (unlike the other reactions of this type, the result in this case is the trans diol).

Yield: 72% of theory.

LC-MS (Method 2): $R_t$=4.38 min.

MS (ESIpos): m/z=572 (M+H)$^+$ $^1$H-NMR (400 MHz, DMSO-d$_6$): δ=7.27-7.22 (m, 2 H), 7.13-7.04 (m, 5 H), 7.00-6.95 (m, 2 H), 6.29 (d, 1 H), 6.18 (d, 1 H), 5.01 (s, 1 H), 4.56-4.51 (m, 1 H), 4.41 (d, 1 H), 4.22-4.09 (m, 4 H), 3.86 (dd, 1 H), 3.70-3.64 (m, 4 H), 3.34 (s, 6 H) 2.70 (ddd, 1 H), 1.96 (dd, 1 H).

Example 19

(3S*,3aR*,8bR*)-6,8-Bis(2-methoxyethoxy)-3a-(4-bromophenyl)-8b-hydroxy-3-phenyl-2,3,3a,8b-tetrahydrocyclopenta[b]benzofuran-1-one

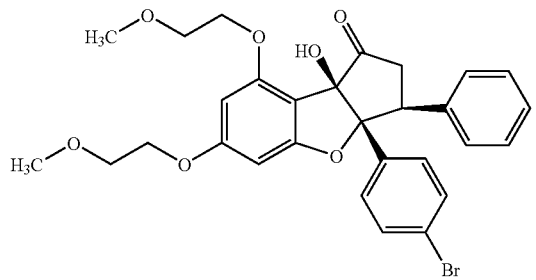

The title compound is prepared in analogy to the synthesis of Example 7A starting from Example 18.

Yield: 33% of theory.

LC-MS (Method 3): $R_t$=4.30 min.

MS (ESIpos): m/z=569 (M+H)$^+$.

Example 20

(1S*,3S*,3aR*,8bS*)-6,8-Bis(2-dimethylaminoethoxy)-3a-(4-chlorophenyl)-3-phenyl-2,3,3a,8b-tetrahydrocyclopenta[b]benzofuran-1,8b-(1H)-diol

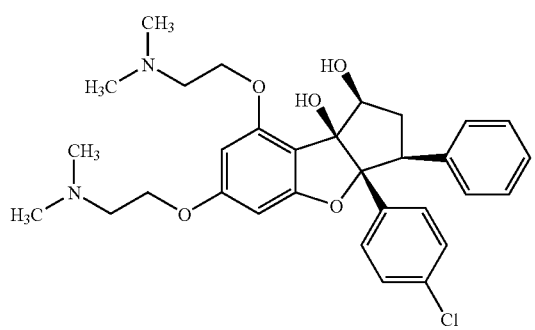

The title compound is prepared in analogy to the synthesis of Example 32 starting from Example 28A.

Yield: 87% of theory.

LC-MS (Method 5): $R_t$=2.12 min.

MS (ESIpos): m/z=553 (M+H)$^+$ $^1$H-NMR (300 MHz, DMSO-d$_6$): δ=7.23-7.03 (m, 7 H), 6.93-6.88 (m, 2 H), 6.44 (d, 1 H), 6.30 (d, 1 H), 4.98 (s, 1 H), 4.67 (t, 1 H), 4.38-4.30 (m, 4 H), 3.48-3.23 (m, 5 H), 2.76 (s, 6 H), 2.70 (s, 6 H), 2.53-2.42 (m, 1 H), 2.21 (ddd, 1 H).

Preparative separation of the racemate into the enantiomers is carried out by HPLC on a chiral phase by Method 15A.

Analytical data (Method 15B):

Enantiomer A: $R_t$=7.23 min., enantiomer B: $R_t$=9.41 min.

Example 21

(1R*,3S*,3aR*,8bS*)-6,8-Bis(2-dimethylaminoethoxy)-3a-(4-chlorophenyl)-3-phenyl-2,3,3a,8b-tetrahydrocyclopenta[b]benzofuran-1,8b-(1H)-diol

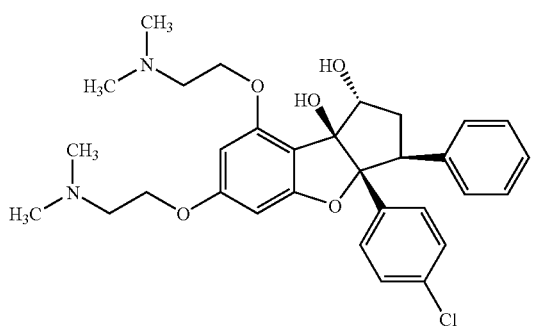

The title compound is prepared in analogy to the synthesis of Example 32 starting from Example 30A.
Yield: 82% of theory.
LC-MS (Method 2): $R_t$=2.03 min.
MS (ESIpos): m/z=553 (M+H)$^+$
$^1$H-NMR (200 MHz, DMSO-d$_6$): δ=7.20-6.95 (m, 9 H), 6.27 (d, 1 H), 6.20 (d, 1 H), 5.16 (s, 1 H), 4.49 (d, 1 H), 4.26-4.11 (m, 1 H), 4.11-4.02 (m, 4 H), 3.84 (dd, 1 H), 2.86-2.55 (m, 5 H), 2.24 (s, 6 H), 2.19 (s, 6 H), 1.95 (dd, 1 H).

Preparative separation of the racemate into the enantiomers is carried out by HPLC on a chiral phase by Method 15A.
Analytical data (Method 15B):
Enantiomer A: $R_t$=6.78 min., enantiomer B: $R_t$=8.18 min.

Example 22

(1S*,3S*,3aR*,8bS*)-6,8-Bis(2-dimethylaminoethoxy)-3a-(4-bromophenyl)-3-phenyl-2,3,3a,8b-tetrahydrocyclopenta[b]benzofuran-1,8b-(1H)-diol

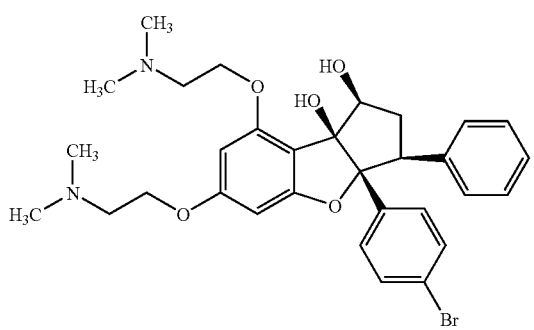

The title compound is prepared in analogy to the synthesis of Example 32 starting from Example 35A.
Yield: 59% of theory.
LC-MS (Method 4): $R_t$=2.19 min.
MS (ESIpos): m/z=597 (M+H)$^+$
$^1$H-NMR (400 MHz, DMSO-d$_6$): δ=7.34-7.29 (m, 2 H), 7.18-7.12 (m, 2 H), 7.11-7.04 (m, 3 H), 6.94-6.88 (m, 2 H), 6.48 (d, 1 H), 6.32 (d, 1 H), 6.10 (s, 1 H), 5.01 (s, 1 H), 4.68 (t, 1 H), 4.43-4.37 (m, 4 H), 3.66-3.45 (m, 5 H), 2.87 (s, 6 H), 2.85 (s, 6 H), 2.55-2.43 (m, 1 H), 2.31-2.15 (m, 1 H).

Example 23

(1S*,3S*,3aR*,8bS*)-3a-(4-Chlorophenyl)-6-ethoxy-3-phenyl-2,3,3a,8b-tetrahydrocyclopenta[b]-benzofuran-1,8b-(1H)-diol

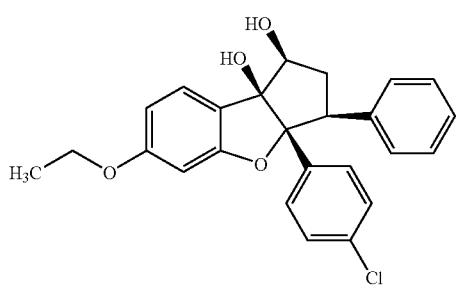

The title compound is prepared in analogy to the synthesis of Example 6A starting from Example 39A.
Yield: 73% of theory.
LC-MS (Method 3): $R_t$=3.57 min.
MS (ESIneg): m/z=421 (M)$^-$
$^1$H-NMR (200 MHz, DMSO-d$_6$): δ=7.28-6.90 (m, 10 H), 6.66 (d, 1 H), 6.57 (dd, 1 H), 5.84 (d, 1 H), 5.03 (s, 1 H), 4.49-4.39 (m, 1 H), 4.05 (q, 3 H), 3.31-3.25 (m, 1 H), 2.49-2.38 (m, 1 H), 2.24-2.15 (m, 1 H), 1.34 (t, 3 H).

Preparative separation of the racemate into the enantiomers is carried out by HPLC on a chiral phase by Method 30A.
Analytical data (Method 30B):
Enantiomer A: $R_t$=3.90 min., enantiomer B: $R_t$=5.46 min.

Example 24

(3S*,3aR*,8bR*)-3a-(4-Chlorophenyl)-6-ethoxy-8b-hydroxy-3-phenyl-2,3,3a,8b-tetrahydrocyclopenta[b]benzofuran-1-one

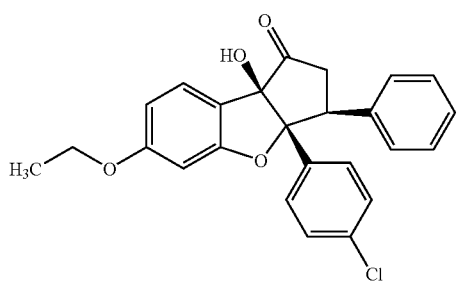

The title compound is prepared in analogy to the synthesis of Example 7A starting from Example 23.
Yield: 81% of theory.
LC-MS (Method 9): $R_t$=2.66 min.
MS (ESIpos): m/z=403 [M+H—H$_2$O]$^+$ $^1$H-NMR (200 MHz, DMSO-$d_6$): δ=7.25-7.01 (m, 10 H), 6.82 (d, 1 H), 6.62 (dd, 1 H), 6.28 (s, 1 H), 4.08 (q, 2 H), 3.69-3.58 (m, 1 H), 3.42-3.22 (m, 1 H), 2.93-2.79 (m, 1 H), 1.35 (t, 3 H).

Example 25

(3S*,3aR*,8bR*)-3a-(4-Chlorophenyl)-6-ethoxy-8b-hydroxy-3-phenyl-2,3,3a,8b-tetrahydrocyclopenta[b]benzofuran-1-oxime

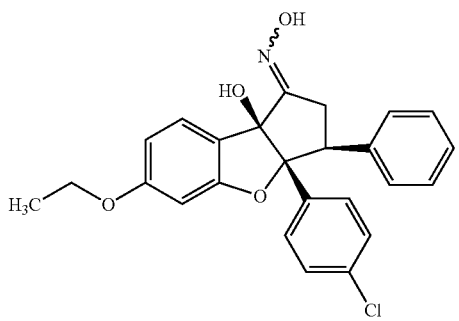

The title compound is prepared in analogy to the synthesis of Example 14 starting from Example 24.
Yield: 99% of theory.
LC-MS (Method 9): $R_t$=2.57 min.
MS (ESIneg): m/z=434 (M−H)$^-$
$^1$H-NMR (300 MHz, DMSO-$d_6$): δ=11.12 (s, 1 H), 7.32 (d, 1 H), 7.20.(d, 2 H), 7.11-7.09 (m, 5 H), 7.01-6.98 (m, 2 H), 6.73 (d, 1 H), 6.60 (dd, 1 H), 5.74 (s, 1 H), 4.07 (dq, 2 H), 3.40-3.38 (m, 1 H), 3.04-3.01 (m, 2 H), 1.34 (t, 3 H).

Example 26

(1R*,3S*,3aR*,8bR*)-1-Amino-3a-(4-chlorophenyl)-6ethoxy-8b-hydroxy-3-phenyl-2,3,3a,8b-tetrahydrocyclopenta[b]benzofuran

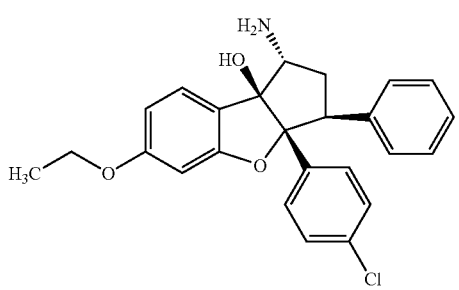

The title compound is prepared in analogy to the synthesis of Example 15 starting from Example 25.
Yield: 50% of theory.
LC-MS (Method 9): $R_t$=1.96 min.
MS (ESIpos): m/z=422 (M−H)$^+$
$^1$H-NMR (300 MHz, DMSO-$d_6$): δ=7.19 (d, 1 H), 7.12-6.94 (m, 9 H), 6.62 (d, 1 H), 6.52 (dd, 1 H), 5.90 (br. s, 1 H), 4.04 (q, 2 H), 3.61 (dd, 1 H), 3.42 (dd, 1 H), 2.43-2.35 (m, 1 H), 2.19-2.07 (m, 1 H), 1.33 (t, 3 H).

Preparative separation of the racemate into the enantiomers is carried out by HPLC on a chiral phase by Method 27A.
Analytical data (Method 27B):
Enantiomer A: $R_t$=4.22 min., enantiomer B: $R_t$=7.38 min.

Example 27

(2R*,3S*,3aR*,8bR*)-3a-(4-Chlorophenyl)-6-ethoxy-2-dimethylcarbamid-8-hydroxy-3-phenyl-2,3,3a,8b-tetrahydrocyclopenta[b]benzofuran-1-one

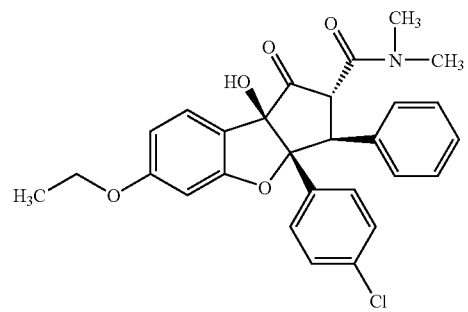

The title compound is prepared in analogy to the synthesis of Example 16 starting from Example 40A.
Yield: 26% of theory.
LC-MS (Method 9): $R_t$=2.49 min.
MS (ESIpos): m/z=492 (M+H)$^+$
$^1$H-NMR (400 MHz, DMSO-$d_6$): δ=7.25-6.96 (m, 10 H), 6.82 (d, 1 H), 6.59 (dd, 1 H), 6.40 (s, 1 H), 4.77 (d, J=13.41 Hz, 1 H), 4.19 (d, J=13.41 Hz, 1 H), 4.14-4.05 (m, 2 H), 3.27 (s, 3 H), 2.77 (s, 3 H), 1.38-1.33 (m, 3 H).

Example 28

(1R*,2R*,3S*,3aR*,8bS*)-3a-(4-Chlorophenyl)-6-ethoxy-2-dimethylcarbamid-3-phenyl-2,3,3a,8b-tetrahydrocyclopenta[b]benzofuran-1,8b-(1H)-diol

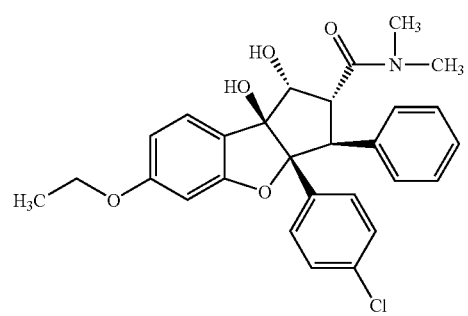

The title compound is prepared in analogy to the synthesis of Example 17 starting from Example 27.
Yield: 61% of theory.
LC-MS (Method 9): $R_t$=2.31 min.
MS (ESIpos): m/z=494 (M+H)$^+$
$^1$H-NMR (200 MHz, DMSO-$d_6$): δ=7.34 (d, 1 H), 7.22-6.80 (m, 9 H), 6.64 (d, 1 H), 6.50 (dd, 1 H), 5.48 (d, 1 H), 5.29 (s, 1 H), 4.91-4.84 (m, 1 H), 4.24-3.95 (m, 4 H), 3.20 (s, 3 H), 2.72 (s, 3 H), 1.34 (t, 3 H).

Preparative separation of the racemate into the enantiomers is carried out by HPLC on a chiral phase by Method 28A.
Analytical data (Method 28B):
Enantiomer A: $R_t$=4.48 min., enantiomer B: $R_t$=10.97 min.

Example 29

(1S*,3S*,3aR*,8bS*)-3a-(4-Bromophenyl)-6-ethoxy-3-phenyl-2,3,3a,8b-tetrahydrocylopenta[b]-benzofuran-1,8b-(1H)-diol

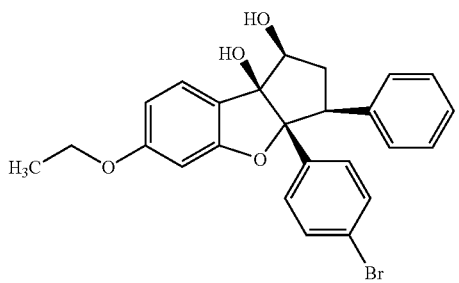

The title compound is prepared in analogy to the synthesis of Examples 2A-6A starting from 3-ethoxyphenol.

LC-MS (Method 12): $R_t$=4.39 min.

MS (ESIpos): m/z=489 (M+Na)$^+$ $^1$H-NMR (200 MHz, DMSO-d$_6$): δ=7.32-7.23 (m, 3 H), 7.16-7.06 (m, 5 H), 6.95-6.91 (m, 2 H), 6.66-6.54 (m, 2 H), 5.83 (d, 1 H), 5.03 (s, 1 H), 4.49-4.39 (m, 1 H), 4.05 (q, 2 H), 3.36-3.26 (m, 1 H), 2.51-2.09 (m, 2 H), 1.34 (t, 3 H).

Example 30

(3S*,3aR*,8bR*)-3a-(4-Bromophenyl)-6-ethoxy-8b-hydroxy-3-phenyl-2,3,3a,8b-tetrahydrocyclopenta[b]benzofuran-1-one

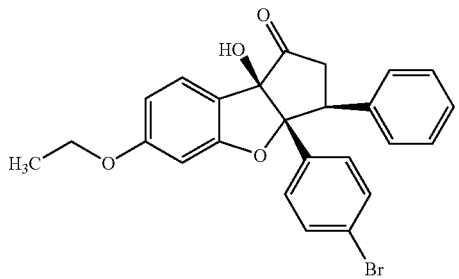

The title compound is prepared in analogy to the synthesis of Example 7A starting from Example 29.

Yield: 85% of theory.

LC-MS (Method 11): $R_t$=4.5 min.

MS (ESIneg): m/z=463 (M)$^-$ $^1$H-NMR (300 MHz, DMSO-d$_6$): δ=7.33-7.02 (m, 10 H), 6.81 (d, 1 H), 6.61 (dd, 1 H), 6.23 (s, 1 H), 4.12-4.05 (m, 2 H), 3.68-3.61 (m, 1 H), 3.40-3.23 (m, 1 H), 2.91-2.82 (m, 1 H), 1.35 (t, 3 H).

Example 31

(1R*,3S*,3aR*,8bS*)-3a-(4-Bromophenyl)-6-ethoxy-3-phenyl-2,3,3a,8b-tetrahydrocyclopenta[b]-benzofuran-1,8b-(1H)-diol

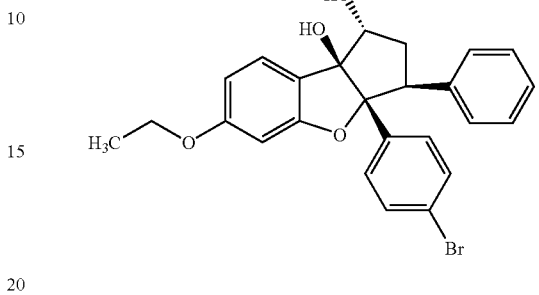

The title compound is prepared in analogy to the synthesis of Example 8A starting from Example 30.

Yield: 79% of theory.

LC-MS (Method 11): $R_t$=4.2 min.

MS (ESIneg): m/z=465 (M-H)$^-$ $^1$H-NMR (200 MHz, DMSO-d$_6$): δ=7.32-7.23 (m, 3 H), 7.11-6.94 (m, 7 H), 6.60 (d, 1 H), 6.50 (dd, 1 H), 5.22 (s, 1 H), 5.14 (d, 1 H), 4.56 (br. s, 1 H), 4.09-3.98 (m, 2 H), 3.89-3.79 (m, 1 H), 2.74-2.57 (m, 1 H), 1.96-1.84 (m, 1 H), 1.34 (t, 3 H).

Example 32

(1S*,3S*,3aR*,8bS*)-3a-(4-Chlorophenyl)-6-(2-dimethylaminoethoxy)-3-phenyl-2,3,3a,8b-tetrahydrocyclopenta[b]benzofuran-1,8b-(1H)-diol

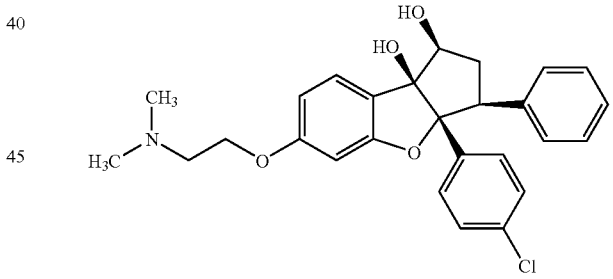

100 mg (0.22 mmol) of (1S*,3S*,3aR*,8bS*)-6-(2-chloroethoxy)-3a-(4-chlorophenyl)-3-phenyl-2,3,3a,8b-tetrahydrocyclopenta[b]benzofuran-1,8b-(1H)-diol (Example 48A) are heated in 10 ml of 33% strength ethanolic dimethylamine solution in a closed apparatus at 70° C. under argon overnight. Cooling is followed by concentration. Column chromatography on silica gel 60 (mobile phase: dichloromethane/methanol/triethylamine 95:5:1) results in 89 mg (87% of theory) of the product as racemic mixture.

LC-MS (Method 1): $R_t$=2.90 min.

MS (ESIpos): m/z=466 (M+H)$^+$ $^1$H-NMR (400 MHz, DMSO-d$_6$): δ=7.30-7.02 (m, 8 H), 6.96-6.88 (m, 2 H), 6.69 (d, 1 H), 6.59 (dd, 1 H), 5.85 (d, 1 H), 5.04 (s, 1 H), 4.51-4.38 (m, 1 H), 4.14-4.04 (m, 2 H), 3.38-3.23 (m, 1 H), 2.73-2.64 (m, 2 H), 2.50-2.37 (m, 1 H), 2.26 (s, 6 H), 2.24-2.10 (m, 1 H).

Example 33

(1S*,3S*,3aR*,8bS*)-3a-(4-Chlorophenyl)-6-(2-pyrrolidin-1-ylethoxy)-3-phenyl-2,3,3a,8b-tetrahydrocyclopenta[b]benzofuran-1,8b-(1H)-diol

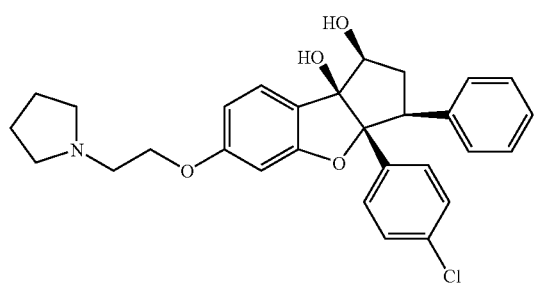

The title compound is prepared in analogy to the synthesis of Example 32 with pyrrolidine as amine component.
Yield: 99% of theory.
LC-MS (Method 2): $R_t$=2.29 min.
MS (ESIpos): m/z=492 (M+H)$^+$
$^1$H-NMR (200 MHz, DMSO-d$_6$): δ=7.30-7.02 (m, 8 H), 6.96-6.88 (m, 2 H), 6.68 (d, 1 H), 6.59 (dd, 1 H), 5.85 (d, 1 H), 5.04 (s, 1 H), 4.51-4.38 (m, 1 H), 4.09 (t, 2 H), 3.37-3.24 (m, 1 H), 2.79 (t, 2 H), 2.57-2.37 (m, 5 H), 2.20 (ddd, 1 H), 1.73-1.65 (m, 4 H).

Preparative separation of the racemate into the enantiomers is carried out by HPLC on a chiral phase by Method 18A.
Analytical data (Method 18B):
Enantiomer A: $R_t$=6.53 min., enantiomer B: $R_t$=8.48 min.

Example 34

(1S*,3S*,3aR*,8bS*)-3a-(4-Chlorophenyl)-6-(2-methylaminoethoxy)-3-phenyl-2,3,3a,8b-tetrahydrocyclopenta[b]benzofuran-1,8b-(1H)-diol

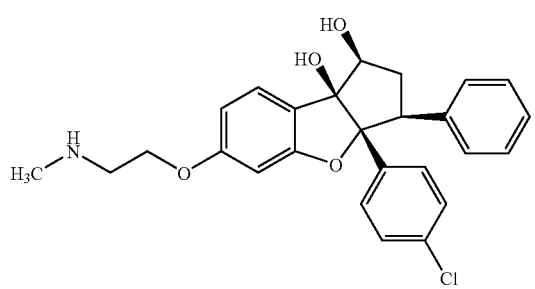

The title compound is prepared in analogy to the synthesis of Example 32 with methylamine as amine component.
Yield: 95% of theory.
LC-MS (Method 2): $R_t$=2.19 min.
MS (ESIpos): m/z=452 (M+H)$^+$
$^1$H-NMR (300 MHz, DMSO-d$_6$): δ=7.79 (s, 1 H), 7.31 (d, 1 H), 7.24-7.13 (m, 4 H), 7.12-7.01 (m, 3 H), 6.95-6.90 (m, 2 H), 6.73 (d, 1 H), 6.64 (dd, 1 H), 5.89 (d, 1 H), 5.03 (s, 1 H), 4.49-4.41 (m, 1 H), 4.22 (t, 2 H), 3.36-3.18 (m, 3 H), 2.57 (s, 3 H), 2.52-2.40 (m, 1 H), 2.22 (ddd, 1 H).

Preparative separation of the racemate into the enantiomers is carried out by HPLC on a chiral phase by Method 16A.
Analytical data (Method 16B):
Enantiomer A: $R_t$=9.31 min., enantiomer B: $R_t$=13.90 min.

Example 35

(1S*,3S*,3aR*,8bS*)-3a-(4-Chlorophenyl)-6-(2-diethylaminoethoxy)-3-phenyl-2,3,3a,8b-tetrahydrocyclopenta[b]benzofuran-1,8b-(1H)-diol

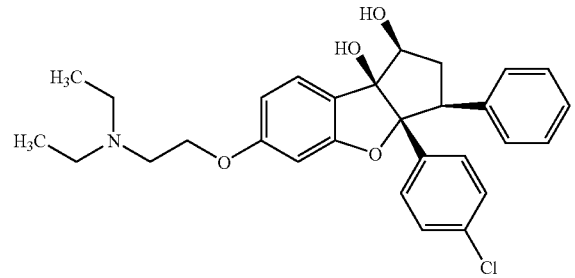

The title compound is prepared in analogy to the synthesis of Example 32 with diethylamine as amine component.
Yield: 56% of theory.
LC-MS (Method 4): $R_t$=2.34 min.
MS (ESIpos): m/z=494 (M+H)$^+$
$^1$H-NMR (400 MHz, DMSO-d$_6$): δ=7.26 (d, 1 H), 7.23-7.14 (m, 4 H), 7.11-7.01 (m, 3 H), 6.94-6.90 (m, 2 H), 6.67 (d, 1 H), 6.58 (dd, 1 H), 5.85 (d, 1 H), 5.02 (s, 1 H), 4.48-4.41 (m, 1 H), 4.06 (t, 2 H), 3.37-3.26 (m, 1 H), 2.86-2.73 (m, 2 H), 2.63-2.54 (m, 4 H), 2.49-2.40 (m, 1 H), 2.20 (ddd, 1 H), 1.00 (t, 6 H).

Example 36

(1S*,3S*,3aR*,8bS*)-3a-(4-Chlorophenyl)-6-(2-ethylaminoethoxy)-3-phenyl-2,3,3a,8b-tetrahydrocyclopenta[b]benzofuran-1,8b-(1H)-diol

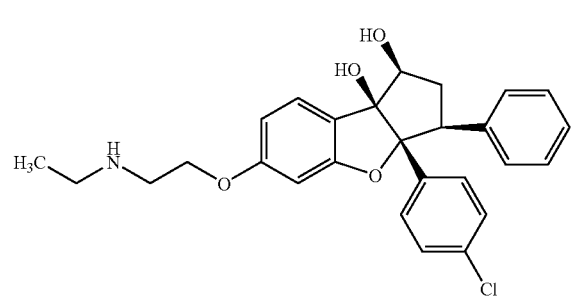

The title compound is prepared in analogy to the synthesis of Example 32 with ethylamine as amine component.
Yield: 31% of theory.
LC-MS (Method 13): $R_t$=1.97 min.
MS (ESIpos): m/z=466 (M+H)$^+$ $^1$H-NMR (300 MHz, DMSO-$d_6$): δ=7.27 (d, 1 H), 7.24-7.13 (m, 4 H), 7.12-7.03 (m, 3 H), 6.95-6.90 (m, 2 H), 6.69 (d, 1 H), 6.61 (dd, 1 H), 5.85 (s, 1 H), 5.02 (s, 1 H), 4.45 (t, 1H), 4.10 (t, 2 H), 3.31 (dd, 1 H), 3.00 (t, 2 H), 2.72 (q, 2 H), 2.48-2.40 (m, 1 H), 2.28-2.14 (m, 1 H), 1.08 (t, 3 H).

Example 37

(1S*,3S*,3aR*,8bS*)-3a-(4-Chlorophenyl)-6-(2-isopropylaminoethoxy)-3-phenyl-2,3,3a,8b-tetrahydrocyclopenta[b]benzofuran-1,8b -(1H)-diol

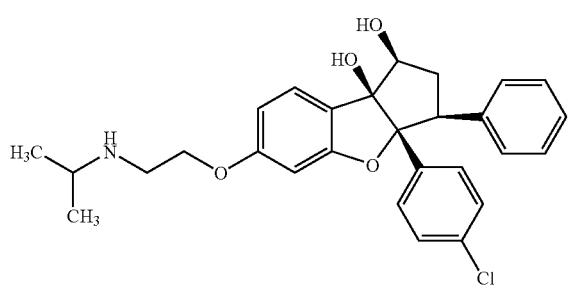

The title compound is prepared in analogy to the synthesis of Example 32 with isopropylamine as amine component.
Yield: 26% of theory.
LC-MS (Method 13): $R_t$=1.97 min.
MS (ESIpos): m/z=480 (M+H)$^+$
$^1$H-NMR (300 MHz, DMSO-$d_6$): δ=7.28 (d, 1 H), 7.24-7.13 (m, 4 H), 7.12-7.03 (m, 3 H), 6.95-6.90 (m, 2 H), 6.69 (d, 1 H), 6.61 (dd, 1 H), 5.85 (s, 1 H), 5.02 (s, 1 H), 4.45 (t, 1 H), 4.10 (t, 2 H), 3.36-3.27 (m, 1 H), 3.00 (t, 2 H), 2.95 (sept, 1 H), 2.48-2.40 (m, 1 H), 2.31-2.14 (m, 1 H), 1.08 (d, 6H).

Example 38

(1S*,3S*,3aR*,8bS*)-6-(2-Azetidin-1-ylethoxy)-3a-(4-chlorophenyl)-3-phenyl-2,3,3a,8b-tetrahydrocyclopenta[b]benzofuran-1,8b-(1H)-diol

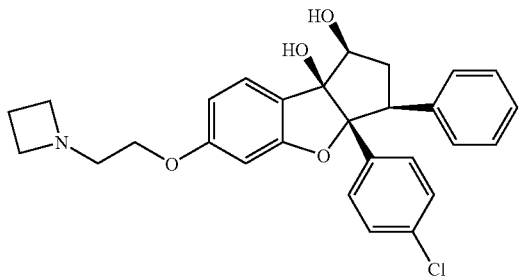

The title compound is prepared in analogy to the synthesis of Example 32 with azetidine as amine component.
Yield: 58% of theory.
LC-MS (Method 13): $R_t$=1.96 min.
MS (ESIpos): m/z=478 (M+H)$^+$
$^1$H-NMR (300 MHz, DMSO-$d_6$): δ=7.25 (d, 1 H), 7.23-7.13 (m, 4 H), 7.12-7.02 (m, 3 H), 6.95-6.90 (m, 2 H), 6.64 (d, 1 H), 6.56 (dd, 1 H), 5.82 (s, 1 H), 5.00 (s, 1 H), 4.44 (t, 1 H), 3.95 (t, 2 H), 3.36-3.27 (m, 1 H), 3.23 (t, 4 H), 2.74 (t, 2 H), 2.48-2.39 (m, 1 H), 2.28-2.14 (m, 1 H), 1.99 (quint, 2 H).

Example 39

(1S*,3S*,3aR*,8bS*)-3a-(4-Chlorophenyl)-6-(2-morpholin-4-ylethoxy)-3-phenyl-2,3,3a,8b-tetrahydrocyclopenta[b]benzofuran-1,8b-(1H)-diol

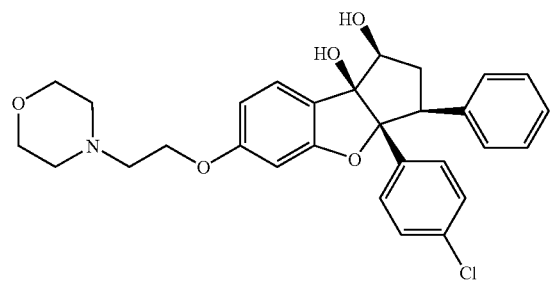

The title compound is prepared in analogy to the synthesis of Example 32 with morpholine as amine component.
Yield: 82% of theory.
LC-MS (Method 9): $R_t$=1.76 min.
MS (ESIpos): m/z=508 (M+H)$^+$
$^1$H-NMR (200 MHz, DMSO-$d_6$): δ=7.29-7.02 (m, 8 H), 6.96-6.87 (m, 2 H), 6.69 (d, 1 H), 6.59 (dd, 1 H), 5.85 (d, 1 H), 5.04 (s, 1 H), 4.50-4.38 (m, 1 H), 4.12 (t, 2 H), 3.63-3.54 (m, 4 H), 3.44-2.98 (m, 5 H), 2.70 (t, 2 H), 2.48-2.36 (m, 1 H), 2.32-2.07 (m, 1 H).

Example 40

(1S*,3S*,3aR*,8bS*)-3a-(4-Chlorophenyl)-6-(2-cyclopropylaminoethoxy)-3-phenyl-2,3,3a,8b-tetrahydrocyclopenta[b]benzofuran-1,8b-(1H)-diol hydroformate

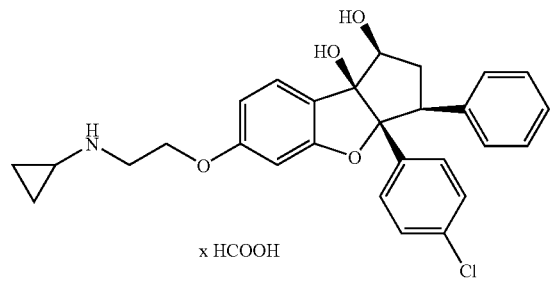

The title compound is prepared in analogy to the synthesis of Example 32 with cyclopropylamine as amine component. The crude product is purified by preparative HPLC (RP18 column, mobile phase: acetonitrile/water gradient 5:95→95:5 with 0.1% formic acid).
Yield: 48% of theory.
LC-MS (Method 13): $R_t$=1.94 min.
MS (ESIpos): m/z=478 (M+H)$^+$
$^1$H-NMR (200 MHz, DMSO-$d_6$): δ=8.17 (s, 1 H), 7.30-7.02 (m, 8 H), 6.96-6.88 (m, 2 H), 6.68 (d, 1 H), 6.59 (dd, 1 H), 5.76 (s, 1 H), 5.04 (s, 1 H), 4.50-4.38 (m, 1 H), 4.05 (t, 2 H), 3.48-3.25 (m, 1 H), 2.95 (t, 2 H), 2.47-2.35 (m, 1 H), 2.28-2.08 (m, 2 H), 0.45-0.32 (m, 2 H), 0.30-0.20 (m, 2 H).

Example 41

(1S*,3S*,3aR*,8bS*)-3a-(4-Chlorophenyl)-6-[2-(2-dimethylaminoethylamino)ethoxy]-3-phenyl-2,3,3a,8b-tetrahydrocyclopenta[b]benzofuran-1,8b-(1H)-diol dihydroformate

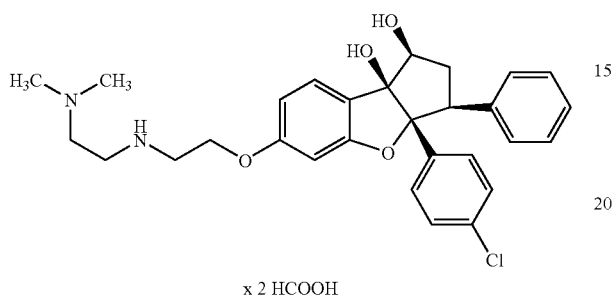

x 2 HCOOH

The title compound is prepared in analogy to the synthesis of Example 32 with 2-dimethylaminoethylamine as amine component. The crude product is purified by preparative HPLC (RP18 column, mobile phase: acetonitrile/water gradient 5:95→95:5 with 0.1% formic acid).
Yield: 85% of theory.
LC-MS (Method 6): $R_t$=1.37 min.
MS (ESIpos): m/z=509 (M+H)$^+$
$^1$H-NMR (300 MHz, DMSO-d$_6$): δ=8.22 (s, 2 H), 7.30-7.02 (m, 8 H), 6.95-6.90 (m, 2 H), 6.70 (d, 1 H), 6.60 (dd, 1 H), 4.45 (t, 1 H), 4.12 (t, 2 H), 3.31 (dd, 1 H), 3.02 (t, 2 H), 2.81 (t, 2 H), 2.47-2.36 (m, 1 H), 2.25 (s, 6 H), 2.24-2.14 (m, 3 H).

Example 42

(1S*,3S*,3aR*,8bS*)-6-(2-Aminoethoxy)-3a-(4-chlorophenyl)-3-phenyl-2,3,3a,8b-tetrahydrocyclopenta[b]benzofuran-1,8b-(1H)-diol

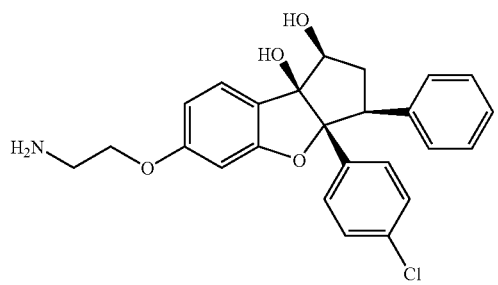

210 mg (0.45 mmol) of (1S*,3S*,3aR*,8bS*)-6-(2-azidoethoxy)-3a-(4-chlorophenyl)-3-phenyl-2,3,3a,8b-tetrahydrocyclopenta[b]benzofuran-1,8b-(1H)-diol (Example 49A) are dissolved in 34 ml of ethanol. Addition of 56 mg of 10% palladium on activated carbon is followed by stirring at RT under hydrogen at atmospheric pressure for 15 minutes. The residue from filtration and concentration is filtered through silica gel 60. Toluene is used for washing, and a 1:1 dichloromethane/ethanol mixture is used for elution. Concentration results in 179 mg (90% of theory) of the product, which is finally purified by Method 23A.
LC-MS (Method 9): $R_t$=1.74 min.
MS (ESIpos): m/z=438 (M+H)$^+$
$^1$H-NMR (200 MHz, DMSO-d$_6$): δ=7.33-6.84 (m, 10 H), 6.70 (d, 1 H), 6.61 (dd, 1 H), 5.89 (s, 1 H), 5.76 (s, 2 H), 5.05 (s, 1 H), 4.52-4.38 (m, 1 H), 4.02 (t, 2 H), 3.39-3.20 (m, 1 H), 2.98 (t, 2 H), 2.50-2.36(m, 1 H), 2.34-2.10 (m, 1 H).
HPLC (Method 23B): $R_t$=8.76 min.
Preparative separation of the racemate into the enantiomers is carried out by HPLC on a chiral phase by Method 24A (enantiomer A: $R_t$=11.0 min., enantiomer B: $R_t$=23.6 min.).

Example 43

(1R*,3S*,3aR*,8bS*)-3a-(4-Chlorophenyl)-6-(2-dimethylaminoethoxy)-3-phenyl-2,3,3a,8b-tetrahydrocyclopenta[b]benzofuran-1,8b-(1H)-diol

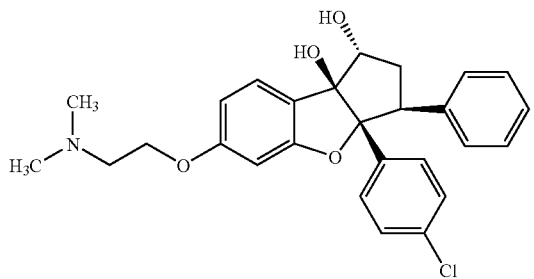

The title compound is prepared in analogy to the synthesis of Example 32 starting from Example 51A.
Yield: 94% of theory.
LC-MS (Method 5): $R_t$=2.41 min.
MS (ESIpos): m/z=466 (M+H)$^+$
$^1$H-NMR (200 MHz, DMSO-d$_6$): δ=7.32 (d, 1 H), 7.19-7.02 (m, 7 H), 6.99-6.91 (m, 2 H), 6.60 (d, 1 H), 6.54 (dd, 1 H), 5.26 (s, 1 H), 5.18 (d, 1 H), 4.62-4.52 (m, 1 H), 4.16 (t, 2 H), 3.83 (dd, 1 H), 3.02-2.88 (m, 2 H), 2.75-2.57 (m, 1 H), 2.54 (s, 3 H), 2.46 (s, 3 H), 1.98-1.82 (m, 1 H).

Example 44

(1R*,2R*,3S*,3aR*,8bS*)-3a-(4-Chlorophenyl)-6-(2-dimethylaminoethoxy)-2-dimethylcarbamid-3-phenyl-2,3,3a,8b-tetrahydrocyclopenta[b]benzofuran-1,8b-(1H)-diol

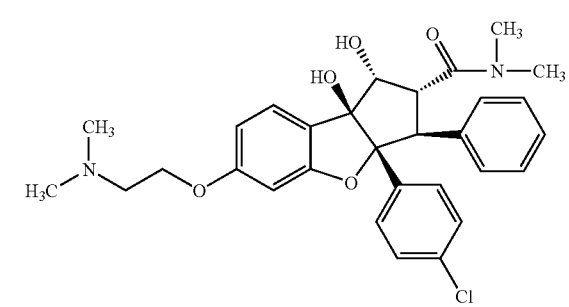

The title compound is prepared in analogy to the synthesis of Example 32 starting from Example 54A.

Yield: 64% of theory.
LC-MS (Method 2): $R_t$=2.10 min.
MS (ESIpos): m/z=537 (M+H)⁺
¹H-NMR (200 MHz, DMSO-d₆): δ=7.39 (d, 1 H), 7.25-6.98 (m, 7 H), 6.86-6.78 (m, 2 H), 6.75 (d, 1 H), 6.57 (dd, 1 H), 5.54 (d, 1 H), 5.33 (s, 1 H), 4.96-4.84 (m, 1 H), 4.34-4.12 (m, 3 H), 4.10-3.94 (m, 1 H), 3.48-3.28 (m, 2 H), 3.20 (s, 3 H), 2.72 (s, 3 H), 2.74-2.62 (m, 6 H).

Example 45

(1R*,3S*,3aR*,8bS*)-3a-(4-Chlorophenyl)-8b-hydroxy-3-phenyl-6-(2-pyrrolidin-1-ylethoxy)-2,3,3a,8b-tetrahydrocyclopenta[b]benzofuran-1-amine dihydroformate

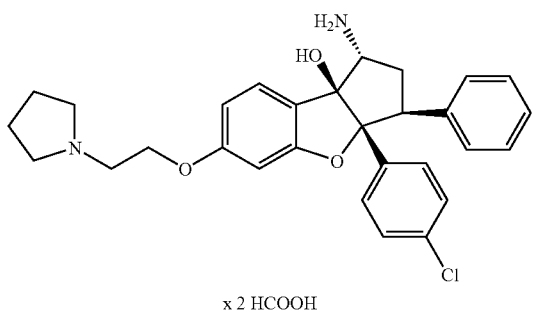

x 2 HCOOH

The title compound is prepared in analogy to the synthesis of Example 32 starting from Example 56A. The crude product is purified by preparative HPLC (RP18 column, mobile phase: acetonitrile/water gradient 5:95→95:5 with 0.1% formic acid).
Yield: 67% of theory.
LC-MS (Method 6): $R_t$=1.20 min.
MS (ESIpos): m/z=491 (M+H)⁺
¹H-NMR (300 MHz, DMSO-d₆): δ=8.21 (s, 2 H), 7.36 (d, 1 H), 7.21-7.04 (m, 7 H), 6.99-6.94 (m, 2 H), 6.67 (d, 1 H), 6.58 (dd, 1 H), 4.10 (t, 2 H), 3.80-3.70 (m, 1 H), 3.50 (dd, 1 H), 2.82 (t, 2 H), 2.59-2.53 (m, 4 H), 2.48-2.37 (m, 1 H), 2.35-2.18 (m, 1 H), 1.73-1.67 (m, 4 H).

Example 46

(1R*,3S*,3aR*,8bS*)-3a-(4-Chlorophenyl)-6-(2-dimethylaminoethoxy)-8b-hydroxy-3-phenyl-2,3,3a,8b-tetrahydrocyclopenta[b]benzofuran-1-amine dihydroformate

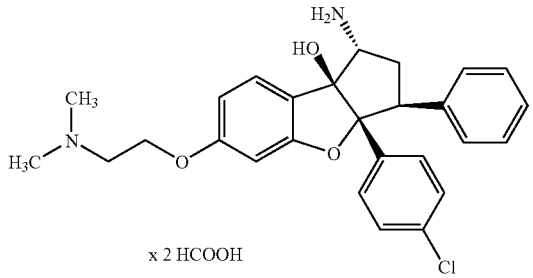

x 2 HCOOH

The title compound is prepared in analogy to the synthesis of Example 32 starting from Example 56A. The crude product is purified by preparative HPLC (RP18 column, mobile phase: acetonitrile/water gradient 5:95→95:5 with 0.1% formic acid).
Yield: 36% of theory.
LC-MS (Method 6): $R_t$=1.22 min.
MS (ESIpos): m/z=465 (M+H)⁺
¹H-NMR (400 MHz, DMSO-d₆): δ=8.23 (s, 2 H), 7.35 (d, 1 H), 7.21-7.02 (m, 7 H), 6.99-6.94 (m, 2 H), 6.68 (d, 1 H), 6.58 (dd, 1 H), 4.08 (t, 2 H), 3.75 (dd, 1 H), 3.50 (dd, 1 H), 2.64 (t, 2 H), 2.47-2.37 (m, 1 H), 2.34-2.23 (m, 1 H), 2.23 (s, 6 H).

Example 47

(1S*,3S*,3aR*,8bS*)-6-Benzyloxy-3a-(4-chlorophenyl)-3-phenyl-2,3,3a,8b-tetrahydrocyclopenta-[b]benzofuran-1,8b-(1H)-diol

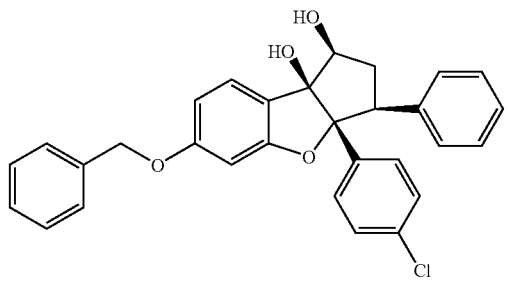

The title compound is prepared in analogy to the synthesis of Example 6A starting from Example 61A.
Yield: 54% of theory.
LC-MS (Method 3): $R_t$=4.85 min.
MS (ESIneg): m/z=483 (M−H)⁻
¹H-NMR (300 MHz, DMSO-d₆): δ=7.46-7.12 (m, 13 H), 6.88-6.85 (m, 2 H), 6.60-6.55 (m, 2 H), 5.64 (d, 1 H), 5.08-5.06 (m, 3 H), 4.16-4.15 (m, 1 H), 4.07-3.99 (m, 1 H), 1.94-1.91 (m, 2 H).

Example 48

(1S*,3S*,3aR*,8bS*)-3a-(4-Chlorophenyl)-3-phenyl-8-(2-pyrrolidin-1-ylethoxy)-2,3,3a,8b-tetrahydrocyclopenta[b]benzofuran-1,8b-(1H)-diol

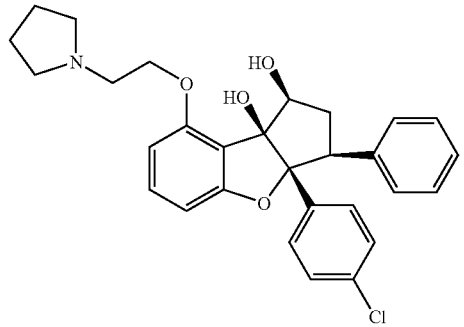

The title compound is prepared in analogy to the synthesis of Example 32 starting from Example 69A.

Yield: 70% of theory.
LC-MS (Method 7): $R_t$=2.10 min.
MS (ESIpos): m/z=492 (M+H)$^+$
$^1$H-NMR (300 MHz, DMSO-d$_6$): δ=7.26 (t, 1 H), 7.21-7.17 (m, 2 H), 7.16-7.11 (m, 2 H), 7.10-7.02 (m, 3 H), 6.99-6.94 (m, 2 H), 6.68 (d, 1 H), 6.64 (d, 1 H), 6.49 (br. s, 1 H), 4.95 (br. s, 1 H), 4.54 (dd, 1 H), 4.28-4.19 (m, 1 H), 4.16-4.06 (m, 1 H), 3.41-3.25 (m, 1 H), 3.10-2.95 (m, 1 H), 2.75-2.51 (m, 5 H), 2.47-2.37 (m, 1 H), 2.32-2.18 (m, 1 H), 1.79-1.71 (m, 4 H).

Preparative separation of the racemate into the enantiomers is carried out by HPLC on a chiral phase by Method 17A.
Analytical data (Method 17B):
Enantiomer A: $R_t$=8.60 min., enantiomer B: $R_t$=9.55 min.

Example 49

(1S*,3S*,3aR*,8bS*)-3a-(4-Chlorophenyl)-8-(2-dimethylaminoethoxy)-3-phenyl-2,3,3a,8b-tetrahydrocyclopenta[b]benzofuran-1,8b-(1H)-diol

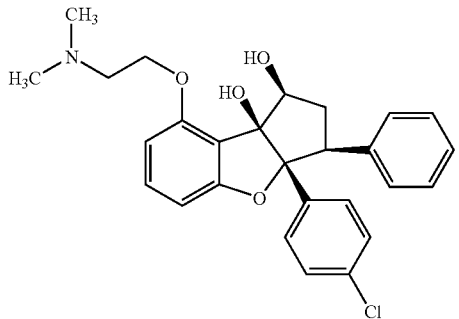

The title compound is prepared in analogy to the synthesis of Example 32 starting from Example 69A.
Yield: 81% of theory.
LC-MS (Method 9): $R_t$=1.88 min.
MS (ESIpos): m/z=466 (M+H)$^+$
$^1$H-NMR (300 MHz, DMSO-d$_6$): δ=7.26 (t, 1 H), 7.22-7.17 (m, 2 H), 7.16-7.11 (m, 2 H), 7.10-7.02 (m, 3 H), 6.99-6.93 (m, 2 H), 6.68 (d, 1 H), 6.64 (d, 1 H), 6.52 (br. s, 1 H), 4.92 (br. s, 1 H), 4.55 (dd, 1 H), 4.23-4.15 (m, 1 H), 4.14-4.05 (m, 1 H), 3.38-3.26 (m, 1 H), 2.87-2.76 (m, 1 H), 2.60-2.38 (m, 2 H), 2.32-2.17 (m, 1 H), 2.25 (s, 6 H).

Example 50

(1S*,3S*,3aR*,8bS*)-3a-(4-Chlorophenyl)-8-(2-methylaminoethoxy)-3-phenyl-2,3,3a,8b-tetrahydrocyclopenta[b]benzofuran-1,8b-(1H)-diol

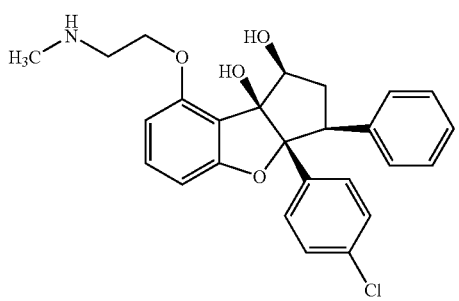

The title compound is prepared in analogy to the synthesis of Example 32 starting from Example 69A.
Yield: 17% of theory.
LC-MS (Method 9): $R_t$=1.88 min.
MS (ESIpos): m/z=452 (M+H)$^+$
$^1$H-NMR (300 MHz, DMSO-d$_6$): δ=7.30 (t, 1 H), 7.26-7.14 (m, 4 H), 7.13-7.04 (m, 3 H), 6.95-6.89 (m, 2 H), 6.74 (d, 1 H), 6.66 (d, 1 H), 4.64 (dd, 1 H), 4.36-4.19 (m, 2 H), 3.41-3.25 (m, 1 H), 2.62 (s, 3 H), 2.48-2.39 (m, 1 H), 2.33-2.21 (m, 1 H).

Example 51

(1R*,3S*,3aR*,8bS*)-3a-(4-Chlorophenyl)-8-(2-dimethylaminoethoxy)-3-phenyl-2,3,3a,8b-tetrahydrocyclopenta[b]benzofuran-1,8b-(1H)-diol

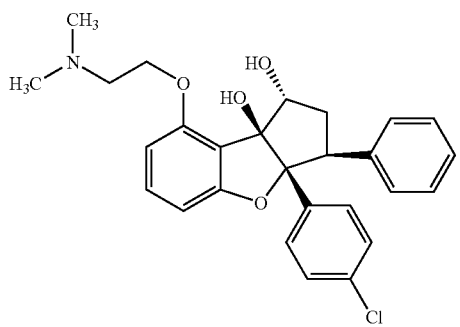

The title compound is prepared in analogy to the synthesis of Example 32 starting from Example 71A.
Yield: 65% of theory.
LC-MS (Method 4): $R_t$=2.24 min.
MS (ESIpos): m/z=466 (M+H)$^+$
$^1$H-NMR (300 MHz, DMSO-d$_6$): δ=7.23 (t, 1 H), 7.19-7.14 (m, 2 H), 7.13-6.98 (m, 7 H), 6.63 (d, 1 H), 6.61 (d, 1 H), 5.30 (br. s, 1 H), 4.54 (d, 1 H), 4.29-4.12 (m, 3 H), 3.88 (dd, 1 H), 2.74 (dt, 1 H), 2.72-2.58 (m, 2 H), 2.23 (s, 6 H), 1.99 (dd, 1 H).

Example 52

(1R*,3S*,3aR*,8bS*)-3a-(4-Chlorophenyl)-3-phenyl-8-(2-pyrrolidin-1-yl-ethoxy)-2,3,3a,8b-tetrahydrocyclopenta[b]benzofuran-1,8b-(1H)-diol

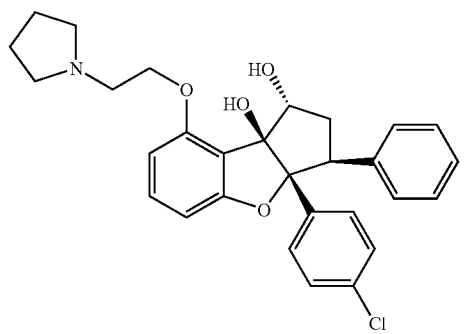

The title compound is prepared in analogy to the synthesis of Example 32 starting from Example 71A.
Yield: 47% of theory.
LC-MS (Method 4): $R_t$=2.29 min.
MS (ESIpos): m/z=492 (M+H)$^+$ ¹H-NMR (300 MHz, DMSO-d₆): δ=7.22 (t, 1 H), 7.18-7.12 (m, 2 H), 7.11-6.99 (m, 7 H), 6.63 (d, 1 H), 6.61 (d, 1 H), 5.42 (br. s, 1 H), 4.51 (d, 1 H), 4.31-4.13 (m, 3 H), 3.91 (dd, 1 H), 2.90-2.65 (m, 2 H), 2.75 (dt, 1 H), 2.63-2.45 (m, 4 H), 1.99 (dd, 1 H), 1.71-1.60 (m, 4 H).

Example 53

(1R*,3S*,3aR*,8bS*)-3a-(4-Chlorophenyl)-8-(2-methoxyethoxy)-3-phenyl-2,3,3a,8b-tetrahydrocyclopenta[b]benzofuran-1,8b-(1H)-diol

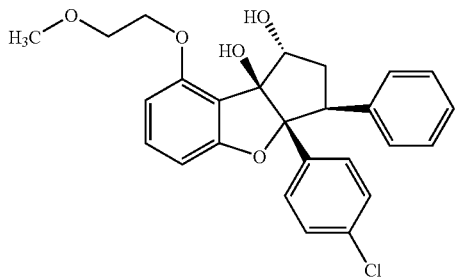

The title compound is prepared in analogy to the synthesis of Example 6A starting from Example 78A.

Yield: 12% of theory.

LC-MS (Method 4): $R_t$=3.50 min.

MS (ESIpos): m/z=453 (M+H)⁺

¹H-NMR (200 MHz, DMSO-d₆): δ=7.24 (t, 1 H), 7.15-6.94 (m, 9 H), 6.66 (d, 1 H), 6.59 (d, 1 H), 5.14 (s, 1 H), 4.62-4.51 (m, 2 H), 4.22-4.14 (m, 2 H), 3.89 (dd, 1 H), 3.73-3.66 (m, 2 H), 3.35 (s, 3 H) 2.74 (ddd, 1 H), 1.98 (dd, 1 H).

Example 54

(1S*,3S*,3aR*,8bS*)-3a-(4-Chlorophenyl)-6-(3-methylaminopropoxy)-3-phenyl-2,3,3a,8b-tetrahydrocyclopenta[b]benzofuran-1,8b-(1H)-diol

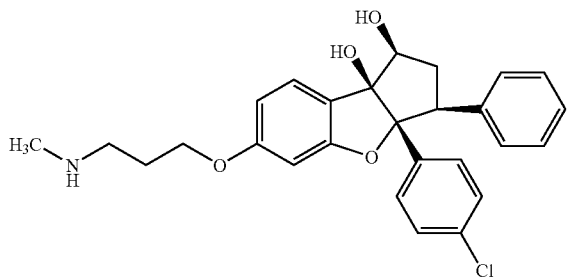

The title compound is prepared in analogy to the synthesis of Example 32 starting from Example 79A.

Yield: 94% of theory.

LC-MS (Method 7): $R_t$=1.83 min.

MS (ESIpos): m/z=466 (M+H)⁺

¹H-NMR (200 MHz, DMSO-d₆): δ=8.63 (br. s, 1 H), 7.32-6.90 (m, 10 H), 6.70 (d, 1 H), 6.60 (dd, 1 H), 5.92 (d, 1 H), 5.04 (s, 1 H), 4.49-4.40 (m, 1 H), 4.13-4.07 (m, 2 H), 3.35-3.20 (m, 1 H), 3.08-3.00 (m, 2 H), 2.58 (s, 3 H), 2.55-2.03 (m, 4 H).

Example 55

(1S*,3S*,3aR*,8bS*)-3a-(4-Chlorophenyl)-6-(3-dimethylaminopropoxy)-3-phenyl-2,3,3a,8b-tetrahydrocyclopenta[b]benzofuran-1,8b-(1H)-diol

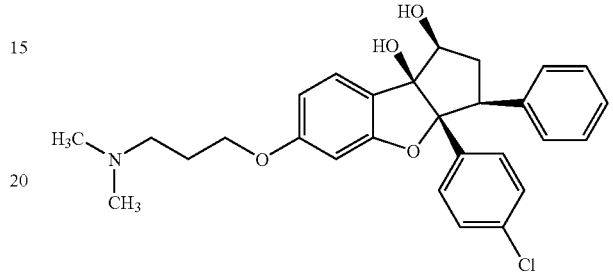

The title compound is prepared in analogy to the synthesis of Example 32 starting from Example 79A.

Yield: 99% of theory.

LC-MS (Method 7): $R_t$=1.86 min.

MS (ESIpos): m/z=480 (M+H)⁺

¹H-NMR (200 MHz, DMSO-d₆): δ=7.30-6.90 (m, 10 H), 6.68 (d, 1 H), 6.58 (dd, 1 H), 5.89 (d, 1 H), 5.04 (s, 1 H), 4.50-4.44 (m, 1 H), 4.08-4.01 (m, 2 H), 3.35-3.25 (m, 1 H), 2.71-2.64 (m, 2 H), 2.39 (s, 6 H), 2.29-2.11 (m, 2 H), 2.02-1.91 (m, 2 H).

Example 56

(1S*,3S*,3aR*,8bS*)-3a-(4-Chlorophenyl)-3-phenyl-6-(3-pyrrolidin-1-ylpropoxy)-2,3,3a,8b-tetrahydrocyclopenta[b]benzofuran-1,8b-(1H)-diol

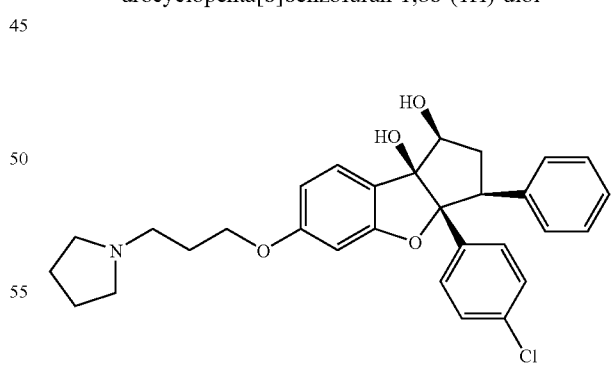

The title compound is prepared in analogy to the synthesis of Example 32 starting from Example 79A.

Yield: 99% of theory.

LC-MS (Method 7): $R_t$=1.91 min.

MS (ESIpos): m/z=506 (M+H)⁺

$^1$H-NMR (200 MHz, DMSO-d$_6$): δ=7.32-6.90 (m, 10 H), 6.70 (d, 1 H), 6.60 (dd, 1 H), 5.91 (d, 1 H), 5.05 (s, 1 H), 4.50-4.40 (m, 1 H), 4.13-4.07 (m, 2 H), 3.35-3.19 (m, 7 H), 2.50-1.92 (m, 8 H).

Example 57

(1S*,3S*,3aR*,8bS*)-6-(3-Azetidin-1-ylpropoxy)-3a-(4-chlorophenyl)-3-phenyl-2,3,3a,8b-tetrahydro-cyclopenta[b]benzofuran-1,8b-(1H)-diol

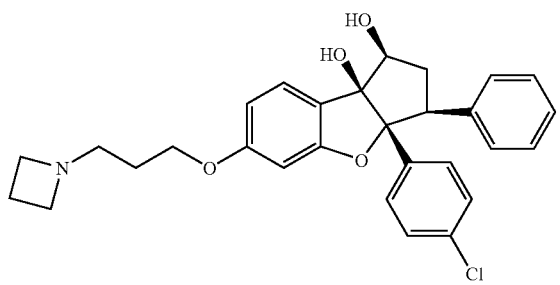

The title compound is prepared in analogy to the synthesis of Example 32 starting from Example 79A.
Yield: 69% of theory.
LC-MS (Method 13): R$_t$=1.97 min.
MS (ESIpos): m/z=492 (M+H)$^+$
$^1$H-NMR (300 MHz, DMSO-d$_6$): δ=7.27-7.03 (m, 8 H), 6.94-6.91 (m, 2 H), 6.64 (d, 1 H), 6.57 (dd, 1 H), 5.82 (d, 1 H), 4.99 (s, 1 H), 4.48-4.41 (m, 1 H), 4.02-3.98 (m, 2 H), 3.12 (m, 4 H), 2.49-2.40 (m, 2 H), 2.26-2.14 (m, 1 H), 1.96 (t, 2 H), 1.70 (t, 2 H), 0.86-0.81 (m, 2 H).

Example 58

N-[(1S*,3S*,3aR*,8bS*)-3a-(4-Chlorophenyl)-1,8b-dihydroxy-3-phenyl-2,3,3a,8b-tetrahydro-1H-benzo[b]cyclopenta[d]furan-6-yl]-2-fluoronicotinamide

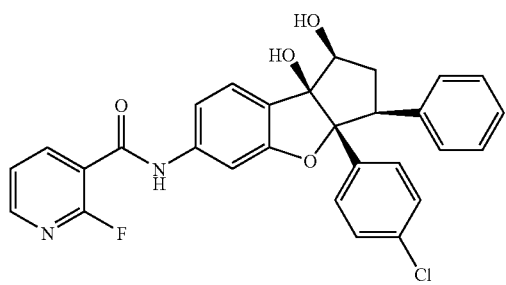

39.4 mg (0.1 mmol) of (1S*,3S*,3aR*,8bS*)-6-amino-3a-(4-chlorophenyl)-3-phenyl-1,2,3,3a-tetrahydrocyclopenta[b]benzofuran-1,8b-(1H)-diol (Example 84A), 14.1 mg (0.1 mmol) of 2-fluoropicoline, 41.7 mg (0.13 nmol) of O-(benzotriazol-1-yl)-N,N,N',N'-tetramethyluronium tetrafluoroborate and 25.8 mg (0.2 mmol) of diisopropylethylamine are mixed in 0.5 ml of DMSO and stirred at room temperature overnight. The solid is then filtered off and the filtrate is purified by preparative HPLC.
Yield: 19.7 mg (38% of theory.)
LC-MS (Method 10): R$_t$=2.21 min.
MS (ESIpos): m/z=517 (M+H)$^+$.

Example 59

N-[(1S*,3S*,3aR*,8bS*)-3a-(4-Chlorophenyl)-1,8b-dihydroxy-3-phenyl-2,3,3a,8b-tetrahydro-1H-benzo[b]cyclopenta[d]furan-6-yl]-6-fluoropyridine-2-carboxamide

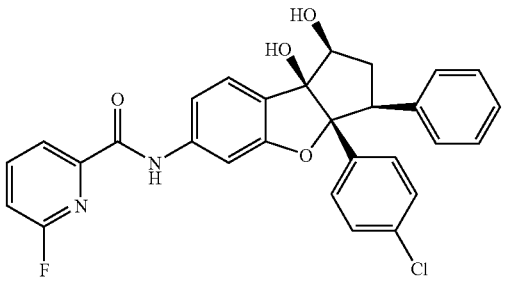

The title compound is prepared in analogy to the synthesis of Example 58 starting from Example 84A.
LC-MS (Method 10): R$_t$=2.35 min.
MS (ESIneg): m/z=515 (M−H)$^−$.

Example 60

N-[(1S*,3S*,3aR*,8bS*)-3a-(4-Chlorophenyl)-1,8b dihydroxy-3-phenyl-2,3,3a,8b-tetrahydro-1H-benzo[b]cyclopenta[d]furan-6-yl]-1-ethyl-1H-pyrazole-3-carboxamide

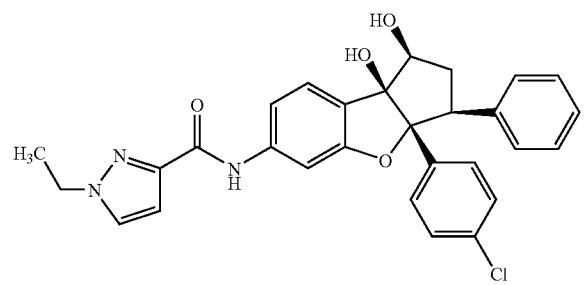

The title compound is prepared in analogy to the synthesis of Example 58 starting from Example 84A.
LC-MS (Method 10): R$_t$=2.25 min.
MS (ESIpos): m/z=516 (M+H)$^+$.

Example 61

N-[(1S*,3S*,3aR*,8bS*)-3a-(4-Chlorophenyl)-1,8b-dihydroxy-3-phenyl-2,3,3a,8b-tetrahydro-1H-benzo[b]cyclopenta[d]furan-6-yl]-1,2,3-thiadiazole-4-carboxamide

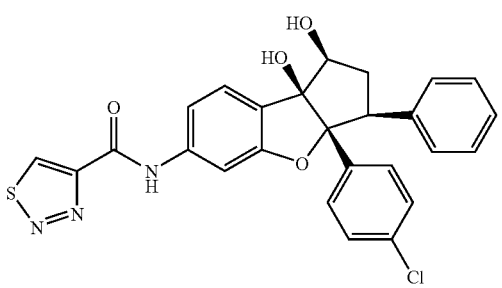

The title compound is prepared in analogy to the synthesis of Example 58 starting from Example 84A.
LC-MS (Method 10): $R_t$=2.23 min.
MS (ESIneg): m/z=504 (M−H)⁻.

Example 62

N-[(1S*,3S*,3aR*,8bS*)-3a-(4-Chlorophenyl)-1,8b-dihydroxy-3-phenyl-2,3,3a,8b-tetrahydro-1H-benzo[b]cyclopenta[d]furan-6-yl]pyridine-2-carboxamide

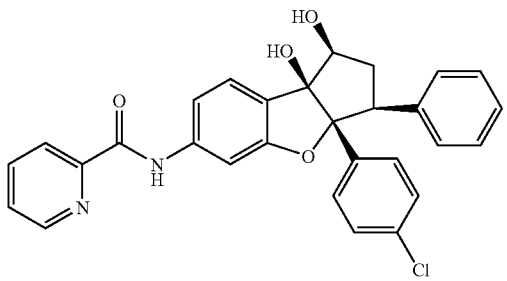

The title compound is prepared in analogy to the synthesis of Example 58 starting from Example 84A.
LC-MS (Method 10): $R_t$=2.38 min.
MS (ESIpos): m/z=499 (M+H)⁺.

Example 63

N-[(1S*,3S*,3aR*,8bS*)-3a-(4-Chlorophenyl)-1,8b-dihydroxy-3-phenyl-2,3,3a,8b-tetrahydro-1H-benzo[b]cyclopenta[d]furan-6-yl]-1H-1,2,4-triazole-5-carboxamide

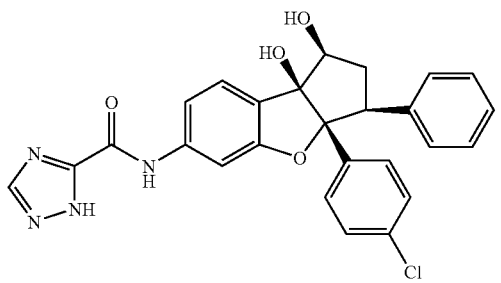

The title compound is prepared in analogy to the synthesis of Example 58 starting from Example 84A.
LC-MS (Method 10): $R_t$=2.00 min.
MS (ESIpos): m/z=489 (M+H)⁺.

B. Assessment of the Pharmacological Activity

The pharmacological effect of the compounds according to the invention can be shown in the following assays:

1. In Vitro Determination of the NF-κB- and AP-1-Inhibitory Effect 1.a) Inhibition of Interleukin-8 (IL-8) Release from Human Endothelial Cells The expression of the human IL-8 gene is controlled by a diversity of regulatory and enhancer elements which are located above the promoter region of the gene. These elements comprise binding sites for transcription factors, and efficient transcription of the IL-8 gene is possible only through the interaction thereof with their DNA binding sites. The activity of the corresponding transcription factors can be induced by various stimuli (e.g. interleukin-1β, tumor necrosis factor-α) and can be modulated by various signal transduction pathways [H. Holtmann et al., Mol. Cell. Biol. 19, 6742-6753 (1999)].

For maximum expression of IL-8, the activity of two different transcription factors is essential: NF-κB and AP-1 [Y.-H. Chang et al., Exp. Cell Res. 278, 166-174 (2000)]. Cytokine-induced IL-8 synthesis can therefore be employed as test system for identifying and characterizing test substances which inhibit directly or indirectly the binding of NF-κB and AP-1 to their DNA binding sites.

Experimental Procedure:

Human umbilical cord endothelial cells (HUVEC) were purchased from CellSystems (St. Katharinen, Germany) and cultured in accordance with the supplier's recommendation in EGM-2 medium including growth additions (CellSystems, St. Katharinen, Germany) in 165 cm² tissue culture bottles. After the cell lawn has reached 60-80% confluence, the cells are detached from the base of the bottle by trypsin treatment, mechanically dissociated and seeded in a cell density of 5000 cells/well in 96-well microtiter plates (Corning, Wiesbaden, Germany). After 3 days, the culture medium is completely replaced by 170 µl of fresh medium per well. The cells are employed for the experiments on the following day.

To determine the inhibitory effect of the substances according to the invention on IL-8 release, they are firstly dissolved in a concentration ten times higher than the desired final concentration in the test in medium which comprises 1% DMSO. Subsequently, 20 µl of the substance solution are added per well. The formation and release of IL-8 is then induced by adding interleukin-1β (IL-1β, final concentration 10 ng/ml; Biosource GmbH, Solingen, Germany), and the cells are incubated in a CO₂ incubator at 37° C. for 6 h. Thereafter, 150 µl of the cell supernatant are removed and frozen at −20° C. until the IL-8 content is measured by ELISA (Biosource GmbH, Solingen, Germany). To carry out the ELISA, the samples are thawed and are diluted 1:10, and the test is carried out in accordance with the manufacturer's instructions. The inhibitory effect of the compounds according to the invention on IL-8 release is ascertained by comparison with vehicle-treated cells.

Representative data on the effect of the compounds according to the invention are listed in table 1 below:

TABLE 1

| Example No. | IC₅₀ [nM] |
| --- | --- |
| 3 | 170 |
| 12 | 466 |
| 15 | 166 |
| 18 | 20 |
| 22 | 90 |
| 23 | 202 |
| 32 | 112 |
| 48 | 214 |

[IC₅₀ = concentration of active substance which brings about a 50% inhibition of IL-8 release relative to the maximum effect thereof].

1.b) Inhibition of AP-1 Activity in Astrocyte Cultures

AP-1 is a transcription factor which is formed from homo- or heterodimers of the Jun, Fos and ATF family and is localized in the cell nucleus. Activating signals lead on the one hand to an increased synthesis of the individual components, and on the other hand to a specific phosphorylation of the Jun or ATF subunits. Both processes lead to an enhanced interaction of the protein complex with its target genes and thus enables expression thereof. Stimulus-induced phosphorylation of, for example, c-Jun can thus serve as indicator of AP-1 activation. The influence of the compounds according to the invention on AP-1 activation can be investigated with the aid of the immunocytochemical detection, described below, of C-Jun phosphorylation.

Experimental Procedure:

Mixed glia cell cultures were prepared from brains of 1-day old rats (Wistar). For this purpose, the animals were sacrificed by decapitation, and the brains were removed and collected in cold Hank's salt solution (HBSS, Gibco, Karlsruhe, Germany). Brainstem and cerebellum are removed, the cerebral hemispheres are freed of meninges, and the pieces of tissue are dissociated mechanically in the presence of papain (Papain dissociation kit, CellSystems, St. Katharinen, Germany). The cells are collected by centrifugation at 450×g and plated out in 175 cm² tissue culture bottles. The cells are cultured in DMEM/Ham's F12 medium, 10% fetal calf serum, 100 µg/ml penicillin/streptomycin (Sigma, Taufkirchen, Germany) for 12-14 days. Cell fragments and microglial and oligodendroglial cells growing on the surface of the cell lawn are then shaken off with the aid of a shaker for 2 h, and the remaining astrocytes are detached from the base of the bottle by trypsinization. The cells are mechanically dissociated, collected by centrifugation at 450×g, again mechanically dissociated and distributed in a density of 100 000 cells/well in poly-D-lysine-coated 8-chamber slides (NUNC, Denmark). The astrocytes concentrated in this way are cultured in phenol red-free DMEM/Ham's F12 medium, 10% fetal calf serum, 100 µg/ml penicillin/streptomycin (Sigma, Taufkirchen, Germany). One day before they are used in the experiment, the fetal calf serum content in the medium is reduced to 1%.

To investigate the effect of the compounds according to the invention on AP-1 activation, they are added in the desired concentration to the culture medium (final concentration in the test usually 1 µM). Subsequently, the AP-1 signaling pathway (c-Jun phosphorylation) is stimulated by adding lipopolysaccharide (LPS, Sigma, Taufkirchen, Germany) in a final concentration of 100 ng/ml or by adding interleukin-1β (IL-1β, Biosource GmbH, Solingen, Germany) in a final concentration of 30 ng/ml. After 90 min, the cells are briefly washed with phosphate-buffered saline (PBS) and then fixed in 4% paraformaldehyde solution in PBS for 10 min. The cells are subsequently permeabilized with methanol at −20° C. for 5 min, washed in PBS, 5% sucrose, 0.3% TritonX-100, and incubated in blocking buffer (PBS, 1% goat serum, 2% BSA) at room temperature for 30 min. Incubation with primary antibodies which are directed against the astrocyte-specific protein GFAP (glial fibrillary acidic protein; mouse monoclonal antibody, Sigma, Taufkirchen, Germany) and against the serine-63-phosphorylated form of c-Jun (rabbit polyclonal antibody, Calbiochem, Bad Soden, Germany) takes place in the same mixture at 4° C. overnight. The antibodies against GFAP are diluted 1:400, and those against phospho-c-Jun 1:50, in blocking buffer. Excess antibody is subsequently removed by washing three times in PBS, 5% sucrose, 0.3% TritonX-100, and the cells are incubated at room temperature successively, for 1 h each time, with the respective secondary, species-specific antibodies (anti-mouse Cy2-conjugated antibodies, 1:500, Amersham Biosciences, Freiburg, Germany; anti-rabbit Cy3-conjugated antibodies, 1:800, Sigma, Taufkirchen, Germany) which have been diluted in blocking buffer. Excess antibody is then removed by washing three times in PBS, 5% sucrose, 0.3% TritonX-100, and the cell nuclei are stained by incubating the cells with Hoechst 33258 (4 µg/ml in PBS) for 10 min. Finally, the cells are again washed twice with PBS for 5 min, the sealing ring of the 8-chamber slide is removed, and the cells are embedded in embedding medium (Sigma, Taufkirchen, Germany) with the aid of a cover slip. The result of the experiment can be assessed with the aid of a fluorescence microscope (objective magnification 25×).

Phosphorylated c-Jun protein is identifiable by a red fluorescence located in the cell nucleus owing to the binding of the Cy3-conjugated secondary antibody to the detecting primary antibody directed against phospho-c-Jun. The cell nucleus has a blue fluorescent appearance. Astrocytes are identifiable by a Cy-2-mediated, green fluorescent GFAP staining.

Under basal conditions, only few cell nuclei contain phosphorylated c-Jun. Addition of LPS induces the AP-1-mediated signal transduction so that more than 80% of the cell nuclei show reddish fluorescence, i.e. contain phospho-c-Jun. The red coloration is distinctly reduced by addition of the compounds according to the invention, being expressed firstly by a reduction in the color intensity and secondly by a diminution in the colored nuclei. Colocalization of the processes in astrocytes is made possible by superimposing the green, red and blue fluorescence images.

2. Determination of the Metabolic Stability

In Vitro Incubation with Liver Microsomes:

The hepatic microsomal stability is determined by incubating the substances according to the invention with liver microsomes from various species. The incubation concentration of the substances is kept as low as possible (preferably <1 µM), as is the concentration of the microsomal proteins in the test mixture (preferably 0.2 mg of microsomal protein per ml of incubation mixture). This procedure makes it possible to operate in the linear region of the Michaelis-Menten kinetics for most compounds. A sample is taken from the incubation mixture at various times (seven times in total) to determine the remaining substance concentration. The clearance (CL) and the maximum bioavailability (Fmax) of the test substance is calculated for the respective species from the half-life of the substance in the incubation mixture. The content of organic solubilizers does not exceed 1% acetonitrile or 0.2% DMSO, in order to minimize the effect on the microsomal enzymes.

Experimental Procedure:

The experiments are carried out as described in detail in J. B. Houston and D. J. Carlile [*Drug Metab. Rev.* 29, 891-922 (1997)].

As shown by way of example for the compounds listed in table 2, the substances according to the invention display an increased stability, compared with the compounds described in WO 00/08007, in liver microsome preparations:

TABLE 2

| Example No. | Mouse liver microsomes | |
|---|---|---|
| | CL [l/(kg × h)] | Fmax [%] |
| 3 | <2.7 | >50 |
| 12 | 2.97 | 45.1 |
| 15 | <2.7 | >50 |
| 18 | <2.7 | >50 |
| 22 | <2.7 | >50 |

TABLE 2-continued

| | Mouse liver microsomes | |
|---|---|---|
| Example No. | CL [l/(kg × h)] | Fmax [%] |
| 32 | <2.7 | >50 |
| 48 | <2.7 | >50 |
| Comparative: I-41 from WO 00/08007 | 5.0 | 6.8 |

3. In Vitro Proliferation of Tumor Cells

Various types of cancer are characterized by uncontrolled, excessive proliferation of various cell types, leading to the development of metastases and tumors. The possible use of the substances according to the invention for the treatment of hyperproliferative disorders can be investigated by their activity on the cell division rate of tumor cells in vitro. The indicator between antiproliferative effect in vitro and clinical antitumor effect is well established. The therapeutic utilizability of, for example, Taxol [Silvestrini et al., *Stem Cells* 11, 528-535 (1993)], Taxotere [Bissery et al., *Anti Cancer Drugs* 6, 339 (1995)] or topoisomerase inhibitors [Edelman et al., *Cancer Chemother. Pharmacol.* 37, 385-393 (1996)] was demonstrated through their activity in in vitro tumor cell proliferation assays.

Experimental Procedure:

The tumor cell lines such as, for example, MDA-MB-231 cells (human breast adenocarcinoma cells), H460 cells (human lung carcinoma cells) or HCT-15 cells (human colon adenocarcinoma cells) are expanded in appropriate growth media (Sigma, Taufkirchen, Germany) recommended by the supplier (e.g. LGC Promochem, Wesel, Germany). One day before adding the compounds according to the invention, the cells are distributed in a density of 3000 cells/well in 100 μl of growth medium on black 96-well microtiter plates with clear base. On the day of addition of test substance, one microtiter plate for each tumor cell line is used to determine the initial cell count present in the wells. The substances according to the invention, diluted in growth medium and DMSO, are added to the related plates. The test substances are usually added in various concentrations starting with 10 μM final concentration in the assay. The DMSO concentration in the assay is 0.1%. Twenty-four hours after addition of the substance, the cell counts in each well are determined using the CellTiter-Glo® Luminescent Cell Viability-Tests (Promega GmbH, Mannheim, Germany). The test is carried out in accordance with the manufacturer's instructions and evaluated using a luminometer. To ascertain the antiproliferative activity of the compounds according to the invention, the cell counts determined before addition of substance in related plates are subtracted, and the percentage difference of the changes in the cell counts between substance-treated and vehicle-treated cells is determined. The relative activity of the different test substances is determined by a comparison of the concentrations which bring about 50% of their maximum effect ($IC_{50}$).

Representative data on the effect of the compounds according to the invention are listed in table 3 below:

TABLE 3

| Example No. | $IC_{50}$ [nM] (H460 cells) |
|---|---|
| 21 | 1.5 |
| 23 | 99.7 |
| 32 | 0.5 |

TABLE 3-continued

| Example No. | $IC_{50}$ [nM] (H460 cells) |
|---|---|
| 48 | 47.9 |
| 49 | 29.7 |

[$IC_{50}$ = concentration of active substance which brings about a 50% inhibition of tumor cell proliferation relative to their maximum effect].

4. Mouse MPTP Animal Model of Parkinson's Disease

Parkinson's disease is characterized histopathologically by selective loss of a group of nerve cells of the substantia nigra which synthesize the neurotransmitter dopamine. 1-Methyl-4-phenyl-1,2,3,6-tetrahydropyridine (MPTP) is an impurity of synthetic drugs which was identified in the early 1980s and which induces symptoms of parkinsonism and the characteristic degeneration of dopaminergic neurons in humans. Administration of MPTP in various species such as, for example, mouse or monkey leads to behavioral and histopathological changes which are comparable to those of the human disorder. The mouse MPTP animal model is therefore regarded as a valid model of Parkinson's disease and as suitable for investigating the neuroprotective effect properties of test substances.

Experimental Procedure:

The experiments are essentially carried out as described by E. Bezard et al. [*Neurosci. Lett.* 234, 47-50 (1997)]. Male 8-week old C57/BL6 mice each receive i.p. administration of 4 mg/kg MPTP on three consecutive days. The substances according to the invention are administered orally each day or twice a day starting immediately before the first MPTP administration. On day 11 after the first MPTP dose, the animals are anesthetized and undergo intracardiac profision firstly with 25 ml of 0.9% saline and then with 75 ml of 4% paraformaldehyde solution, and the brains are removed for histological processing. As described by E. Bezard et al. [*Neurosci. Lett.* 234, 47-50 (1997)], for this purpose the dopaminergic neurons are visualized immunohistochemically as cells which contain the enzyme tyrosine hydroxylase which is essential in dopamine metabolism. The number of remaining dopaminergic neurons is ascertained quantitatively with the aid of a computer program in three different sections for each animal, which are representative of a plane of section through the middle of the substantia nigra [Nelson et al., *J. Comp. Neurol.* 369, 361-371 (1996)]. The neuroprotective activity of the test substances is determined by comparing with vehicle-treated MPTP animals and completely untreated animals.

5. Subdural Hematoma in Rats as Animal Model of Traumatic Craniocerebral Injuries Severe traumatic cranial injuries are often accompanied by accummulations of blood underneath the meninges. The subdural accummulation of blood leads to a local reduction in cerebral blood flow in the adjacent cortical region of the brain with a simultaneous rise in glucose consumption and in extracellular excitatory amino acids (e.g. glutamate). The region of the brain adjacent to the hematoma becomes ischemic, leading to damage and death of nerve cells. Subdural injection of autologous blood in cortical regions of the rat brain serves as animal model to simulate traumatic craniocerebral injuries in humans. The animal model is suitable for investigating the neuroprotective activity of the substances according to the invention.

Experimental Procedure:

The surgical procedure on male Wistar rats and the unilateral administration of autologous blood is carried out as described in detail by M. Eijkenboom et al. [*Neuropharm.* 39, 817-834 (2000)]. The substances according to the invention are injected intravenously in the desired doses immediately after closure of the wound and after 2 h and 4 h. Seven days after the operation, the animals are sacrificed, the brains are removed and the infarct volume is determined as described by M. Eijkenboom et al. [*Neuropharm.* 39, 817-834 (2000)]. The neuroprotective activity of the substances according to the invention is determined by comparing with vehicle-treated animals.

C. Exemplary Embodiments of Pharmaceutical Compositions

The compounds according to the invention can be converted into pharmaceutical preparations in the following ways:

Tablet:
Composition:

100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:

A mixture of compound according to the invention, lactose and starch is granulated with a 5% strength solution (m/m) of the PVP in water. The granules are dried and mixed with the magnesium stearate for 5 minutes. This mixture is compressed in a conventional tablet press (see above for format of the tablet). A guideline compressive force for the compression is 15 kN.

Suspension which can be Administered Orally:
Composition:

1000 mg of the compound according to the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound according to the invention.

Production:

The Rhodigel is suspended in ethanol, and the compound according to the invention is added to the suspension. The water is added while stirring. The mixture is stirred for about 6 h until the swelling of the Rhodigel is complete.

Solution which can be Administered Orally:
Composition:

500 mg of the compound according to the invention, 2.5 g of polysorbate and 97 g of polyethylene glycol 400. 20 g of oral solution correspond to a single dose of 100 mg of the compound according to the invention.

Production:

The compound according to the invention is suspended in the mixture of polyethylene glycol and polysorbate with stirring. The stirring process is continued until the compound according to the invention has completely dissolved.

i.v. Solution:

The compound according to the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:
1. A compound of the formula (I)

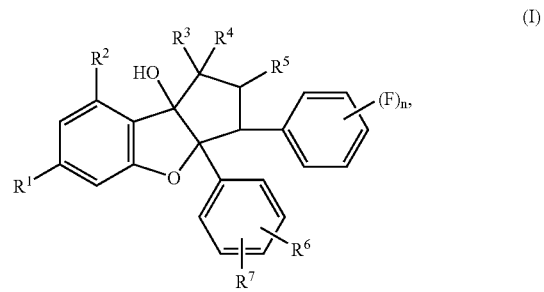

in which
R$^1$ is hydrogen, benzyloxy, ethoxy, n-propoxy or a group of the formula R$^8$—C(=O)—NH—, where ethoxy may be substituted in position 2, and n-propoxy in position 2 or 3, by (C$_1$-C$_6$)-alkoxy, amino, mono- or di-(C$_1$-C$_6$)-alkylamino, (C$_3$-C$_8$)-cycloalkylamino, N-(C$_3$-C$_8$)-cycloalkyl-N-(C$_1$-C$_6$)-alkylamino or by a 4- to 7-membered heterocycle which is bonded via an N atom,
where mono- and di-(C$_1$-C$_4$)-alkylamino in turn may be substituted by hydroxy, (C$_1$-C$_4$)-alkoxy, amino, mono- or di-(C$_1$-C$_4$)-alkylamino,
and in which
R$^8$ is 5- or 6-membered heteroaryl which may be substituted by (C$_1$-C$_4$)-alkyl or halogen,
R$^2$ is hydrogen, ethoxy or n-propoxy, where ethoxy may be substituted in position 2, and n-propoxy in position 2 or 3, by (C$_1$-C$_6$)-alkoxy, amino, mono- or di-(C$_1$-C$_6$)-alkylamino, (C$_3$-C$_8$)-cycloalkylamino, N-(C$_3$-C$_8$)-cycloalkyl-N-(C$_1$-C$_6$)-alkylamino or by a 4- to 7-membered heterocycle which is bonded via an N atom,
where mono- and di-(C$_1$-C$_6$)-alkylamino in turn may be substituted by hydroxy, (C$_1$-C$_4$)-alkoxy, amino, mono- or di-(C$_1$-C$_4$)-alkylamino,
but where R$^1$ and R$^2$ are not simultaneously hydrogen,
R$^3$ is hydroxy or amino
and
R$^4$ is hydrogen,
or
R$^3$ and R$^4$ together with the carbon atom to which they are bonded form a group of the formula >C=O or >C=N—OH,
R$^5$ is hydrogen,
n is the number 0, 1, 2 or 3,
R$^6$ is located in the meta or para position relative to the point of linkage of the phenyl ring to the tricycle, and is (C$_6$-C$_{10}$)-aryl, 5- to 10-membered heteroaryl or a group of the formula —NR$^9$R$^{10}$,
where aryl and heteroaryl in turn may each be substituted once to twice, identically or differently, by halogen, cyano, (C$_1$-C$_4$)-alkylsulfonyl or a group of the formula —NR$^9$R$^{10}$,
and in which
R$^9$ and R$^{10}$ are independently of one another hydrogen, (C$_1$-C$_6$)-alkyl, phenyl, benzyl or pyridylmethyl, or together with the nitrogen atom to which they are bonded form a 4- to 7-membered heterocycle, and R⁷ is located in the meta or para position relative to the point of linkage of the phenyl ring to the tricycle, and in the ortho position relative to R⁶, and is hydrogen, halogen, $(C_1-C_6)$-alkyl, $(C_1-C_6)$-alkoxy or a group of the formula —NR¹¹R¹², in which R¹¹ and R¹² are independently of one another hydrogen, $(C_1-C_6)$-alkyl, phenyl, benzyl or pyridylmethyl, or together with the nitrogen atom to which they are bonded form a 4- to 7-membered heterocycle, or R⁶ and R⁷ together with the phenyl ring to which they are bonded form a group of the formula

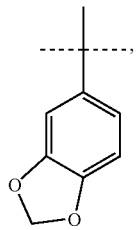

or a salt, solvate or solvate of the salt thereof.

2. A compound of the formula (I) as claimed in claim 1, in which

R¹ is hydrogen, benzyloxy, ethoxy, n-propoxy or a group of the formula R⁸—C(═O)—NH—, where ethoxy may be substituted in position 2, and n-propoxy in position 2 or 3, by $(C_1-C_4)$-alkoxy, amino, mono- or di-$(C_1-C_4)$-alkylamino, $(C_3-C_6)$-cycloalkylamino, N-$(C_3-C_6)$-cycloalkyl-N-$(C_1-C_4)$-alkylamino or by a 4- to 7-membered heterocycle which is bonded via an N atom, where mono- and di-$(C_1-C_4)$-alkylamino in turn may be substituted by hydroxy, $(C_1-C_4)$-alkoxy, amino, mono- or di-$(C_1-C_4)$-alkylamino, and in which R⁸ is 5- or 6-membered heteroaryl which may be substituted by $(C_1-C_4)$-alkyl or halogen, R² is hydrogen, ethoxy or n-propoxy, where ethoxy may be substituted in position 2, and n-propoxy in position 2 or 3, by $(C_1-C_4)$-alkoxy, amino, mono- or di-$(C_1-C_4)$-alkylamino, $(C_3-C_6)$-cycloalkylamino, N-$(C_3-C_6)$-cycloalkyl-N-$(C_1-C_4)$-alkylamino or by a 4- to 7-membered heterocycle which is bonded via an N atom, where mono- and di-$(C_1-C_4)$-alkylamino in turn may be substituted by hydroxy, $(C_1-C_4)$-alkoxy, amino, mono- or di-$(C_1-C_4)$-alkylamino, but where R¹ and R² are not simultaneously hydrogen, R³ is hydroxy or amino and R⁴ is hydrogen, or R³ and R⁴ together with the carbon atom to which they are bonded form a group of the formula >C═O or >C═N—OH, R⁵ is hydrogen, n is the number 0, 1, 2 or 3, R⁶ is located in the meta or para position relative to the point of linkage of the phenyl ring to the tricycle, and is $(C_6-C_{10})$-aryl, 5- to 6-membered heteroaryl or a group of the formula —NR⁹R¹⁰, where aryl and heteroaryl in turn may each be substituted once to twice, identically or differently, by halogen, cyano, $(C_1-C_4)$-alkylsulfonyl or a group of the formula —NR⁹R¹⁰, and in which R⁹ and R¹⁰ are independently of one another hydrogen, $(C_1-C_4)$-alkyl, phenyl, benzyl or pyridylmethyl, or together with the nitrogen atom to which they are bonded form a 4- to 7-membered heterocycle, and R⁷ is located in the meta or para position relative to the point of linkage of the phenyl ring to the tricycle, and in the ortho position relative to R⁶, and is hydrogen, halogen, $(C_1-C_4)$-alkyl, $(C_1-C_4)$-alkoxy or a group of the formula —NR¹¹R¹² in which R¹¹ and R¹² are independently of one another hydrogen, $(C_1-C_4)$-alkyl, phenyl, benzyl or pyridylmethyl, or together with the nitrogen atom to which they are bonded form a 4- to 7-membered heterocycle, or R⁶ and R⁷, together with the phenyl ring to which they are bonded form a group of the formula

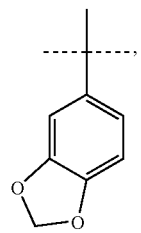

or a salt, solvate or solvate of the salt thereof.

3. A compound of the formula (I) as claimed in claim 1, in which

R¹ is hydrogen, ethoxy, n-propoxy or a group of the formula R⁸—C(═O)—NH—, where ethoxy may be substituted in position 2, and n-propoxy in position 3, by methoxy, ethoxy, amino, methylamino, ethylamino, isopropylamino, dimethylamino, diethylamino, cyclopropylamino, N-cyclopropyl-N-methylamino, azetidino or pyrrolidino, in which R⁸ is pridyl, pyrrolyl, imidazolyl, pyrazolyl, triazolyl or thiadiazolyl, each of which may be substituted by methyl, ethyl, fluorine or chlorine, R² is hydrogen, ethoxy or n-propoxy, where ethoxy may be substituted in position 2, and n-propoxy in position 3, by methoxy, ethoxy, amino, methylamino, ethylamino, isopropylamino, dimethylamino, diethylamino, cyclopropylamino, N-cyclopropyl-N-methylamino, azetidino or pyrrolidino, but where R¹ and R² are not simultaneously hydrogen, R³ is hydroxy or amino, R⁴ is hydrogen, R⁵ is hydrogen, n is the number 0 or 1, R⁶ is located in the meta or para position relative to the point of linkage of the phenyl ring to the tricycle, and is phenyl, thienyl, indolyl, quinoxalinyl or a group of the formula —NR⁹R¹⁰, where phenyl, thienyl and indolyl in turn may each be substituted once to twice, identically or differently, by fluorine, chlorine, bromine, cyano or amino, and in which
R[9] and R[10] are independently of one another hydrogen, methyl, ethyl, benzyl or pyridylmethyl, or together with the nitrogen atom to which they are bonded form a pyrrolidino ring,
and
R[7] is hydrogen,
or a salt, solvate or solvate of the salt thereof.

4. A compound of the formula (I)

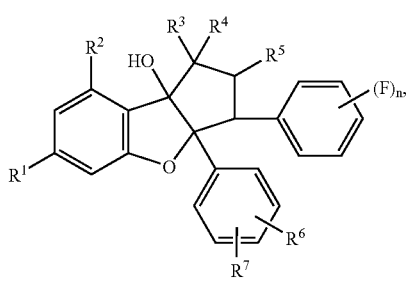

in which
R[1] is hydrogen, benzyloxy, ethoxy, n-propoxy or a group of the formula R[8]—C(=O)—NH—, where ethoxy may be substituted in position 2, and n-propoxy in position 2 or 3, by $(C_1-C_6)$-alkoxy, amino, mono- or di-$(C_1-C_6)$-alkylamino, $(C_3-C_8)$-cycloalkylamino, N-$(C_3-C_8)$-cycloalkyl-N-$(C_1-C_6)$-alkylamino or by a 4- to 7-membered heterocycle which is bonded via an N atom,
where mono- and di-$(C_1-C_6)$-alkylamino in turn may be substituted by hydroxy, $(C_1-C_4)$-alkoxy, amino, mono- or di-$(C_1-C_4)$-alkylamino,
and in which
R[8] is 5- or 6-membered heteroaryl which may be substituted by $(C_1-C_4)$-alkyl or halogen,
R[2] is hydrogen, ethoxy or n-propoxy, where ethoxy may be substituted in position 2, and n-propoxy in position 2 or 3, by $(C_1-C_6)$-alkoxy, amino, mono- or di-$(C_1-C_6)$-alkylamino, $(C_3-C_8)$-cycloalkylamino, N-$(C_3-C_8)$-cycloalkyl-N-$(C_1-C_6)$-alkylamino or by a 4- to 7-membered heterocycle which is bonded via an N atom,
where mono- and di-$(C_1-C_6)$-alkylamino in turn may be substituted by hydroxy, $(C_1-C_4)$-alkoxy, amino, mono- or di-$(C_1-C_4)$-alkylamino,
but where R[1] and R[2] are not simultaneously hydrogen,
R[3] is amino
and
R[4] is hydrogen,
or
R[3] and R[4] together with the carbon atom to which they are bonded form a group of the formula >C=N—OH,
R[5] is hydrogen,
n is the number 0, 1, 2 or 3,
R[6] is located in the meta or para position relative to the point of linkage of the phenyl ring to the tricycle, and is halogen, $(C_1-C_6)$-alkyl or $(C_1-C_6)$-alkoxy,
and
R[7] is located in the meta or para position relative to the point of linkage of the phenyl ring to the tricycle, and in ortho position relative to R[6], and is hydrogen, halogen, $(C_1-C_6)$-alkyl, $(C_1-C_6)$-alkoxy or a group of the formula —NR[11]R[12], in which
R[11] and R[12] are independently of one another hydrogen, $(C_1-C_6)$-alkyl, phenyl, benzyl or pyridylmethyl, or together with the nitrogen atom to which they are bonded form a 4- to 7-membered heterocycle,
or
R[6] and R[7] together with the phenyl ring to which they are bonded form a group of the formula

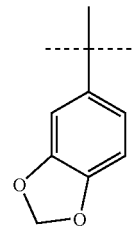

or a salt, solvate or solvate of the salt thereof.

5. A compound of the formula (I) as claimed in claim 4, in which
R[1] is hydrogen, benzyloxy, ethoxy, n-propoxy or a group of the formula R[8]—C(=O)—NH—, where ethoxy may be substituted in position 2, and n-propoxy in position 2 or 3, by $(C_1-C_4)$-alkoxy, amino, mono- or di-$(C_1-C_4)$-alkylamino, $(C_3-C_6)$-cycloalkylamino, N-$(C_3-C_6)$-cycloalkyl-N-$(C_1-C_4)$-alkylamino or by a 4- to 7-membered heterocycle which is bonded via an N atom,
where mono- and di-$(C_1-C_4)$-alkylamino in turn may be substituted by hydroxy, $(C_1-C_4)$-alkoxy, amino, mono- or di-$(C_1-C_4)$-alkylamino,
and in which
R[8] is 5- or 6-membered heteroaryl which may be substituted by $(C_1-C_4)$-alkyl or halogen,
R[2] is hydrogen, ethoxy or n-propoxy, where ethoxy may be substituted in position 2, and n-propoxy in position 2 or 3, by $(C_1-C_4)$-alkoxy, amino, mono- or di-$(C_1-C_4)$-alkylamino, $(C_3-C_6)$-cycloalkylamino, N-$(C_3-C_6)$-cycloalkyl-N-$(C_1-C_4)$-alkylamino or by a 4- to 7-membered heterocycle which is bonded via an N atom,
where mono- and di-$(C_1-C_4)$-alkylamino in turn may be substituted by hydroxy, $(C_1-C_4)$-alkoxy, amino, mono- or di-$(C_1-C_4)$-alkylamino,
but where R[1] and R[2] are not simultaneously hydrogen,
R[3] is amino
and
R[4] is hydrogen
or
R[3] and R[4] together with the carbon atom to which they are bonded form a group of the formula >C=N—OH,
R[5] is hydrogen,
n is the number 0, 1, 2 or 3,
R[6] is located in the meta or para position relative to the point of linkage of the phenyl ring to the tricycle, and is halogen, $(C_1-C_4)$-alkyl or $(C_1-C_4)$-alkoxy,
and
R[7] is located in the meta or para position relative to the point of linkage of the phenyl ring to the tricycle, and in the ortho position relative to R[6], and is hydrogen, halogen, $(C_1-C_4)$-alkyl, $(C_1-C_4)$-alkoxy or a group of the formula —NR[11]R[12], in which
R[11] and R[12] are independently of one another hydrogen, $(C_1-C_6)$-alkyl, phenyl, benzyl or pyridylmethyl, or together with the nitrogen atom to which they are bonded form a 4- to 7-membered heterocycle,
or R⁶ and R⁷ together with the phenyl ring to which they are bonded form a group of the formula

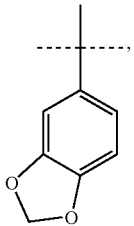

or a salt, solvate or solvate of the salt thereof.

6. A compound of the formula (I) as claimed in claim 4, in which
R¹ is hydrogen, ethoxy, n-propoxy or a group of the formula R⁸—C(=O)—NH—, where ethoxy may be substituted in position 2, and n-propoxy in position 3, by methoxy, ethoxy, amino, methylamino, ethylamino, isopropylamino, dimethylamino, diethylamino, cyclopropylamino, N-cyclopropyl-N-methylamino, azetidino or pyrrolidino, in which
R⁸ is pyridyl, pyrrolyl, imidazolyl, pyrazolyl, triazolyl or thiadiazolyl, each of which may be substituted by methyl, ethyl, fluorine or chlorine,
R² is hydrogen, ethoxy or n-propoxy, where ethoxy may be substituted in position 2, and n-propoxy in position 3, by methoxy, ethoxy, amino, methylamino, ethylamino, isopropylamino, dimethylamino, diethylamino, cyclopropylamino, N-cyclopropyl-N-methylamino, azetidino or pyrrolidino,
but where R¹ and R² are not simultaneously hydrogen,
R³ is amino,
R⁴ is hydrogen
R⁵ is hydrogen,
n is the number 0 or 1,
R⁶ is located in the meta or para position relative to the point of linkage of the phenyl ring to the tricycle, and is fluorine, chlorine, bromine, methyl, ethyl, methoxy or ethoxy,
and
R⁷ is located in the meta or para position relative to the point of linkage of the phenyl ring to the tricycle, and in the ortho position relative to R⁶, and is hydrogen, fluorine, chlorine, bromine, methyl, ethyl, methoxy, ethoxy or a group of the formula —NR¹¹R¹² in which
R¹¹ and R¹² are independently of one another hydrogen, methyl, ethyl, benzyl or pyridylmethyl, or together with the nitrogen atom to which they are bonded form a pyrrolidino or piperidino ring,
or
R⁶ and R⁷ together with the phenyl ring to which they are bonded form a group of the formula

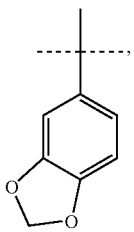

or a salt, solvate or solvate of the salt thereof.

7. A compound of the formula (I)

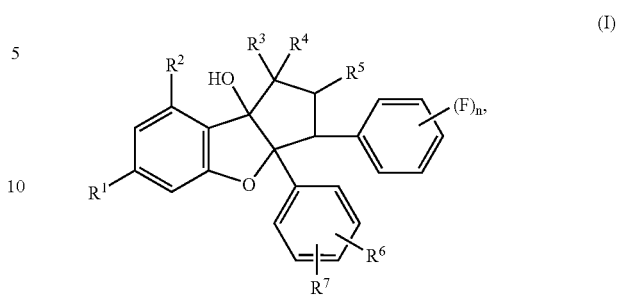

in which
R¹ is hydrogen, benzyloxy, ethoxy, n-propoxy or a group of the formula R⁸—C(=O)—NH—, where ethoxy may be substituted in position 2, and n-propoxy in position 2 or 3, by $(C_1-C_6)$-alkoxy, amino, mono- or di-$(C_1-C_6)$-alkylamino, $(C_3-C_8)$-cycloalkylamino, N-$(C_3-C_8)$-cycloalkyl-N-$(C_1-C_6)$-alkylamino or by a 4- to 7-membered heterocycle which is bonded via an N atom,
where mono- and di-$(C_1-C_6)$-alkylamino in turn may be substituted by hydroxy, $(C_1-C_4)$-alkoxy, amino, mono- or di-$(C_1-C_4)$-alkylamino,
and in which
R⁸ is 5- or 6-membered heteroaryl which may be substituted by $(C_1-C_4)$-alkyl or halogen,
R² is hydrogen, ethoxy or n-propoxy, where ethoxy may be substituted in position 2, and n-propoxy in position 2 or 3, by $(C_1-C_6)$-alkoxy, amino, mono- or di-$(C_1-C_6)$-alkylamino, $(C_3-C_8)$-cycloalkylamino, N-$(C_3-C_8)$-cycloalkyl-N-$(C_1-C_6)$-alkylamino or by a 4- to 7-membered heterocycle which is bonded via an N atom,
where mono- and di-$(C_1-C_6)$-alkylamino in turn may be substituted by hydroxy, $(C_1-C_4)$-alkoxy, amino, mono- or di-$(C_1-C_4)$-alkylamino,
but where one of R¹ and R² represents hydrogen, but R¹ and R² are not simultaneously hydrogen,
R³ is hydroxy
and
R⁴ is hydrogen,
or
R³ and R⁴ together with the carbon atom to which they are bonded form a group of the formula >C=O,
R⁵ is hydrogen,
n is the number 0, 1, 2 or 3,
R⁶ is located in the meta or para position relative to the point of linkage of the phenyl ring to the tricycle, and is halogen, $(C_1-C_6)$-alkyl or $(C_1-C_6)$-alkoxy,
and
R⁷ is located in the meta or para position relative to the point of linkage of the phenyl ring to the tricycle, and in the ortho position relative to R⁶, and is hydrogen, halogen, $(C_1-C_6)$-alkyl, $(C_1-C_6)$-alkoxy or a group of the formula —NR¹¹R¹², in which
R¹¹ and R¹² are independently of one another hydrogen, $(C_1-C_6)$-alkyl, phenyl, benzyl or pyridylmethyl, or together with the nitrogen atom to which they are bonded form a 4- to 7-membered heterocycle, or R$^6$ and R$^7$ together with the phenyl ring to which they are bonded form a group of the formula

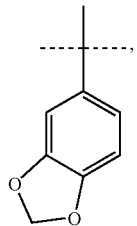

or a salt, solvate or solvate of the salt thereof.

8. A compound of the formula (I) as claimed in claim 7, in which

R$^1$ is hydrogen, benzyloxy, ethoxy, n-propoxy or a group of the formula R$^8$—C(=O)—NH—, where ethoxy may be substituted in position 2, and n-propoxy in position 2 or 3, by (C$_1$-C$_4$)-alkoxy, amino, mono- or di-(C$_1$-C$_4$)-alkylamino, (C$_3$-C$_6$)-cycloalkylamino, N-(C$_3$-C$_6$)-cycloalkyl-N-(C$_1$-C$_4$)-alkylamino or by a 4- to 7-membered heterocycle which is bonded via an N atom, where mono- and di-(C$_1$-C$_4$)-alkylamino in turn may be substituted by hydroxy, (C$_1$-C$_4$)-alkoxy, amino, mono- or di-(C$_1$-C$_4$)-alkylamino, and in which R$^8$ is 5- or 6-membered heteroaryl which may be substituted by (C$_1$-C$_4$)-alkyl or halogen, R$^2$ is hydrogen, ethoxy or n-propoxy, where ethoxy may be substituted in position 2, and n-propoxy in position 2 or 3, by (C$_1$-C$_4$)-alkoxy, amino, mono- or di-(C$_1$-C$_4$)-alkylamino, (C$_3$-C$_6$)-cycloalkylamino, N-(C$_3$-C$_6$)-cycloalkyl-N-(C$_1$-C$_4$)-alkylamino or by a 4- to 7-membered heterocycle which is bonded via an N atom, where mono- and di-(C$_1$-C$_4$)-alkylamino in turn may be substituted by hydroxy, (C$_1$-C$_4$)-alkoxy, amino, mono- or di-(C$_1$-C$_4$)-alkylamino, but where one of R$^1$ and R$^2$ represents hydrogen, but R$^1$ and R$^2$ are not simultaneously hydrogen, R$^3$ is hydroxy and R$^4$ is hydrogen, or R$^3$ and R$^4$ together with the carbon atom to which they are bonded form a group of the formula >C=O, R$^5$ is hydrogen, n is the number 0, 1, 2 or 3, R$^6$ is located in the meta or para position relative to the point of linkage of the phenyl ring to the tricycle, and is halogen, (C$_1$-C$_4$)-alkyl or (C$_1$-C$_4$)-alkoxy, and R$^7$ is located in the meta or para position relative to the point of linkage of the phenyl ring to the tricycle, and in the ortho position relative to R$^6$, and is hydrogen, halogen, (C$_1$-C$_4$)-alkyl, (C$_1$-C$_4$)-alkoxy or a group of the formula —NR$^{11}$R$^{12}$ in which R$^{11}$ and R$^{12}$ are independently of one another hydrogen, (C$_1$-C$_4$)-alkyl, phenyl, benzyl or pyridylmethyl or together with the nitrogen atom to which they are bonded form a 4- to 7-membered heterocycle, or R$^6$ and R$^7$ together with the phenyl ring to which they are bonded form a group of the formula

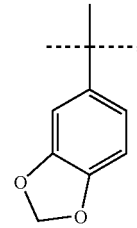

or a salt, solvate or solvate of the salt thereof.

9. A compound of the formula (I) as claimed in claim 7, in which

R$^1$ is hydrogen, ethoxy, n-propoxy or a grouop of the formula R$^8$—C(=O)—NH—, where ethoxy may be substituted in position 2, and n-propoxy in position 3, by methoxy, ethoxy, amino, methylamino, ethylamino, isopropylamino, dimethylamino, diethylamino, cyclopropylamino, N-cyclopropyl-N-methylamino, azetidino or pyrrolidino, in which R$^8$ is pyridyl, pyrrolyl, imidazolyl, pyrazolyl, triazolyl or thiadiazolyl, each of which may be substituted by methyl, ethyl, fluorine or chlorine, R$^2$ is hydrogen, ethoxy or n-propoxy, where ethoxy may be substituted in position 2, and n-propoxy in position 3, by methoxy, ethoxy, amino, methylamino, ethylamino, isopropylamino, dimethylamino, diethylamino, cyclopropylamino, N-cyclopropyl-N-methylamino, azetidino or pyrrolidino, where R$^1$ or R$^2$ is hydrogen, but both are not simultaneously hydrogen, R$^3$ is hydroxy and R$^4$ is hydrogen, or R$^3$ and R$^4$ together with the carbon atom to which they are bonded form a group of the formula >C=O, R$^5$ is hydrogen, n is the number 0 or 1, R$^6$ is located in the meta or para position relative to the point of linkage of the phenyl ring to the tricycle, and is fluorine, chlorine, bromine, methyl, ethyl, methoxy or ethoxy, and R$^7$ is located in the meta or para position relative to the point of linkage of the phenyl ring to the tricycle, and in the ortho position relative to R$^6$, and is hydrogen, fluorine, chlorine, bromine, methyl, ethyl, methoxy, ethoxy or a group of the formula —NR$^{11}$R$^{12}$ in which R$^{11}$ and R$^{12}$ are independently of one another hydrogen, methyl, ethyl, benzyl or pyridylmethyl, or together with the nitrogen atom to which they are bonded form a pyrrolidino or piperidino ring, or R⁶ and R⁷ together with the phenyl ring to which they are bonded form a group of the formula

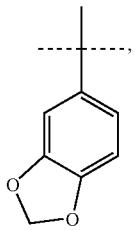

or a salt, solvate or solvate of the salt thereof.

10. A compound of the formula (I)

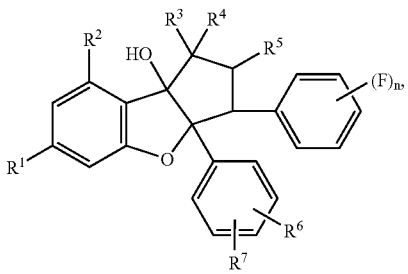

in which

R¹ is ethoxy, n-propoxy or a group of the formula R⁸—C(=O)—NH—, where ethoxy is substituted in position 2, and n-propoxy in position 2 or 3, by $(C_1-C_6)$-alkoxy, amino, mono- or di-$(C_1-C_6)$-alkylamino, $(C_3-C_8)$-cycloalkylamino, N-$(C_3-C_8)$-cycloalkyl-N-$(C_1-C_6)$-alkylamino or by a 4- to 7-membered heterocycle which is bonded via an N atom, where mono- and di-$(C_1-C_6)$-alkylamino in turn may be substituted by hydroxy, $(C_1-C_4)$-alkoxy, amino, mono- or di-$(C_1-C_4)$-alkylamino, and in which R⁸ is 5- or 6-membered heteroaryl which may be substituted by $(C_1-C_4)$-alkyl or halogen, R² is ethoxy or n-propoxy, where ethoxy is substituted in position 2, and n-propoxy in position 2 or 3, by $(C_1-C_6)$-alkoxy, amino, mono- or di-$(C_1-C_6)$-alkylamino, $(C_3-C_8)$-cycloalkylamino, N-$(C_3-C_8)$-cycloalkyl-N-$(C_1-C_6)$-alkylamino or by a 4- to 7-membered heterocycle which is bonded via an N atom, where mono- and di-$(C_1-C_6)$-alkylamino in turn may be substituted by hydroxy, $(C_1-C_4)$-alkoxy, amino, mono- or di-$(C_1-C_4)$-alkylamino, R³ is hydroxy and R⁴ is hydrogen, or R³ and R⁴ together with the carbon atom to which they are bonded form a group of the formula >C=O, R⁵ is hydrogen, n is the number 0, 1, 2 or 3, R⁶ is located in the meta or para position relative to the point of linkage of the phenyl ring to the tricycle, and is halogen, $(C_1-C_6)$-alkyl or $(C_1-C_6)$-alkoxy, and R⁷ is located in the meta or para position relative to the point of linkage of the phenyl ring to the tricycle, and in the ortho position relative to R⁶, and is hydrogen, halogen, $(C_1-C_6)$-alkyl, $(C_1-C_6)$-alkoxy or a group of the formula —NR¹¹R¹², in which R¹¹ and R¹² are independently of one another hydrogen, $(C_1-C_6)$-alkyl, phenyl, benzyl or pyridylmethyl, or together with the nitrogen atom to which they are bonded form a 4- to 7-membered heterocycle, or R⁶ and R⁷ together with the phenyl ring to which they are bonded form a group of the formula

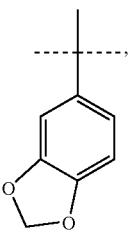

or a salt, solvate or solvate of the salt thereof.

11. A compound of the formula (I) as claimed in claim 10, in which

R¹ is ethoxy, n-propoxy or a group of the formula R⁸—C(=O)—NH—, where ethoxy is substituted in position 2, and n-propoxy in position 2 or 3, by $(C_1-C_4)$-alkoxy, amino, mono- or di-$(C_1-C_4)$-alkylamino, $(C_3-C_6)$-cycloalkylamino, N-$(C_3-C_6)$-cycloalkyl-N-$(C_1-C_4)$-alkylamino or by a 4- to 7-membered heterocycle which is bonded via an N atom, where mono- and di-$(C_1-C_4)$-alkylamino in turn may be substituted by hydroxy, $(C_1-C_4)$-alkoxy, amino, mono- or di-$(C_1-C_4)$-alkylamino, and in which R⁸ is a 5- or 6-membered heteroaryl which may be substituted by $(C_1-C_4)$-alkyl or halogen, R² is ethoxy or n-propoxy, where ethoxy is substituted in position 2, and n-propoxy in position 2 or 3, by $(C_1-C_4)$-alkoxy, amino, mono- or di-$(C_1-C_4)$-alkylamino, $(C_3-C_6)$-cycloalkylamino, N-$(C_3-C_6)$-cycloalkyl-N-$(C_1-C_4)$-alkylamino or by a 4- to 7-membered heterocycle which is bonded via an N atom, where mono- and di-$(C_1-C_4)$-alkylamino in turn may be substituted by hydroxy, $(C_1-C_4)$-alkoxy, amino, mono- or di-$(C_1-C_4)$-alkylamino, R³ is hydroxy and R⁴ is hydrogen, or R³ and R⁴ together with the carbon atom to which they are bonded form a group of the formula >C=O, R⁵ is hydrogen, n is the number 0, 1, 2 or 3, R⁶ is located in the meta or para position relative to the point of linkage of the phenyl ring to the tricycle, and is halogen, $(C_1-C_4)$-alkyl or $(C_1-C_4)$-alkoxy, and R⁷ is located in the meta or para position relative to the point of linkage of the phenyl ring to the tricycle, and in the ortho position relative to R⁶, and is hydrogen, halogen, $(C_1-C_4)$-alkyl, $(C_1-C_4)$-alkoxy or a group of the formula —NR¹¹R¹² in which $R^{11}$ and $R^{12}$ are independently of one another hydrogen, $(C_1-C_4)$-alkyl, phenyl, benzyl or pyridylmethyl, or together with the nitrogen atom to which they are bonded form a 4- to 7-membered heterocycle, or $R^6$ and $R^7$ together with the phenyl ring to which they are bonded form a group of the formula

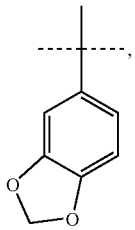

or a salt, solvate or solvate of the salt thereof.

12. A compound of the formula (I) as claimed in claim 10, in which $R^1$ is ethoxy, n-propoxy or a group of the formula $R^8$—C(=O)—NH—, where ethoxy is substituted in position 2, and n-propoxy in position 3, by methoxy, ethoxy, amino, methylamino, ethylamino, isopropylamino, dimethylamino, diethylamino, cyclopropylamino, N-cyclopropyl-N-methylamino, azetidino or pyrrolidino, in which $R^8$ is pyridyl, pyrrolyl, imidazolyl, pyrazolyl, triazolyl or thiadiazolyl, each of which may be substituted by methyl, ethyl, fluorine or chlorine, $R^2$ is ethoxy or n-propoxy, where ethoxy is substituted in position 2, and n-propoxy in position 3, by methoxy, ethoxy, amino, methylamino, ethylamino, isopropylamino, dimethylamino, diethylamino, cyclopropylamino, N-cyclopropyl-N-methylamino, azetidino or pyrrolidino, $R^3$ is hydroxy and $R^4$ is hydrogen, or $R^3$ and $R^4$ together with the carbon atom to which they are bonded form a group of the formula >C=O, $R^5$ is hydrogen, n is the number 0 or 1, $R^6$ is located in the meta or para position relative to the point of linkage of the phenyl ring to the tricycle, and is fluorine, chlorine, bromine, methyl, ethyl, methoxy or ethoxy, and $R^7$ is located in the meta or para position relative to the point of linkage of the phenyl ring to the tricycle, and in the ortho position relative to $R^6$, and is hydrogen, fluorine, chlorine, bromine, methyl, ethyl, methoxy, ethoxy or a group of the formula —$NR^{11}R^{12}$ in which $R^{11}$ and $R^{12}$ are independently of one another hydrogen, methyl, ethyl, benzyl or pyridylmethyl, or together with the nitrogen atom to which they are bonded form a pyrrolidino or piperidino ring, or $R^6$ and $R^7$ together with the phenyl ring to which they are bonded form a group of the formula

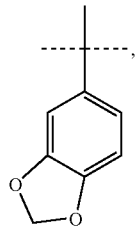

or a salt, solvate or solvate of the salt thereof.

13. A pharmaceutical composition comprising a compound or a salt, solvate or solvate of the salt thereof as defined in any one of claims 1 to 12 in combination with an inert, non-toxic, pharmaceutically suitable excipient.

14. The medicament as claimed in claim 13 which is adapted for the prophylaxis and/or treatment of a condition selected from the group consisting of inflammatory and autoimmune diseases, neurodegenerative disorders and hyperproliferative disorders.

15. A method for the prophylaxis and/or treatment of a condition in a patient in need thereof, said condition being selected from the group consisting of inflammatory and autoimmune diseases, neurodegenerative disorders and hyperproliferative disorders, said method comprising administering to said patient an effective amount therefor of at least one compound or salt, solvate or solvate of the salt thereof as defined in any one of claims 1 to 12.

* * * * *

UNITED STATES PATENT AND TRADEMARK OFFICE
CERTIFICATE OF CORRECTION

PATENT NO.      : 8,030,347 B2
APPLICATION NO. : 11/596907
DATED           : October 4, 2011
INVENTOR(S)     : Nicole Diedrichs et al.

It is certified that error appears in the above-identified patent and that said Letters Patent is hereby corrected as shown below:

In the Specifications

Column 32, line 29, "HNR'R'"" -- should read -- HNR"R'" --.

Column 39, line 66, "diethylarnine" -- should read -- diethylamine --.

Column 43, line 30, "ethoxy" -- should read -- diethoxy --.

Column 75, line 1, "DMSO-6" -- should read -- DMSO-d6 --.

Column 95, line 41, "6ethoxy" -- should read -- 6-ethoxy --.

Column 118, line 36, "profision" -- should read -- profusion --.

In the Claims

Column 128, line 21, "grouop" -- should read -- group --.

Signed and Sealed this
Twenty-fifth Day of March, 2014

Michelle K. Lee
*Deputy Director of the United States Patent and Trademark Office*